(12) United States Patent
Mahurkar

(10) Patent No.: US 7,481,797 B2
(45) Date of Patent: Jan. 27, 2009

(54) RETRACTABLE NEEDLE SINGLE USE SAFETY SYRINGE

(76) Inventor: Sakharam D. Mahurkar, 6171 N. Sheridan Rd., Suite 112, Chicago, IL (US) 60660

( * ) Notice: Subject to any disclaimer, the term of this patent is extended or adjusted under 35 U.S.C. 154(b) by 27 days.

(21) Appl. No.: 11/592,952

(22) Filed: Nov. 3, 2006

(65) Prior Publication Data
US 2007/0060893 A1 Mar. 15, 2007

Related U.S. Application Data

(63) Continuation of application No. 10/051,140, filed on Jan. 22, 2002, now abandoned.

(60) Provisional application No. 60/333,721, filed on Nov. 28, 2001.

(51) Int. Cl.
A61M 5/32 (2006.01)

(52) U.S. Cl. .................. 604/195; 604/195; 604/198; 604/218

(58) Field of Classification Search ............ 604/187, 604/110, 192, 194, 195, 164.01; 128/919
See application file for complete search history.

(56) References Cited

U.S. PATENT DOCUMENTS

| | | | | |
|---|---|---|---|---|
| 2,888,923 | A | 6/1959 | Da Cunha Reis | 128/218 |
| 2,925,083 | A | 2/1960 | Craig | 128/218 |
| 3,610,240 | A | 10/1971 | Harautunelan | 128/214 |
| 3,658,061 | A | 4/1972 | Hall | 128/214 |
| 4,068,659 | A | 1/1978 | Moorehead | 128/214 |
| 4,134,402 | A | 1/1979 | Mahurkar | 128/214 |
| 4,233,982 | A | 11/1980 | Bauer et al. | 128/347 |
| 4,245,635 | A | 1/1981 | Kontos | 128/214 |

(Continued)

FOREIGN PATENT DOCUMENTS

CA 2229550 2/1997

(Continued)

OTHER PUBLICATIONS

"Health Care" by Helene Cooper, Wall Street Journal (Nov. 25, 1992).

(Continued)

*Primary Examiner*—Nicholas D Lucchesi
*Assistant Examiner*—Quynh-Nhu H Vu
(74) *Attorney, Agent, or Firm*—Nixon Peabody LLP

(57) ABSTRACT

A safety syringe assembly includes an elongated, generally cylindrical barrel having a hollow interior forming a hollow nozzle located at a distal end of the barrel and opening into the interior of the barrel. A plunger is slidably mounted in the barrel and has a longitudinal open channel. A needle holder mounts a needle at a distal end thereof and is slidably mounted in the longitudinal open channel of the plunger for movement between an advanced position in which the needle on the distal end of the needle holder projects from a distal end of the nozzle, and a retracted position in which the needle is retracted within the barrel. A compression spring is mounted inside of the barrel, and a spring retainer element has a spring support portion extending from the interiorly of the barrel to a portion for mounted within the barrel and supporting a distal end portion of the spring against expansion. The spring urges the needle holder toward its retracted position. A latch has a closed position in which the needle holder is latched relative to the barrel to hold the needle holder in its advanced position against the urging of the spring, and an open position in which the needle holder is unlatched relative to the barrel to allow the spring to expand in a proximal direction to move the needle holder to its retracted position.

24 Claims, 45 Drawing Sheets

U.S. PATENT DOCUMENTS

| | | | |
|---|---|---|---|
| 4,261,357 A | 4/1981 | Kontos | 128/214 |
| 4,274,408 A | 6/1981 | Nimrod | 128/214 |
| 4,274,836 A | 6/1981 | Ban et al. | 44/6 |
| 4,417,886 A | 11/1983 | Frankhouser et al. | 604/53 |
| 4,424,833 A | 1/1984 | Spector et al. | 137/849 |
| 4,425,120 A | 1/1984 | Sampson et al. | 604/198 |
| D272,651 S | 2/1984 | Mahurkar | D24/54 |
| 4,443,333 A | 4/1984 | Mahurkar | 210/87 |
| 4,468,224 A | 8/1984 | Enzmann et al. | 604/247 |
| 4,529,399 A | 7/1985 | Groshong et al. | 604/53 |
| 4,568,329 A | 2/1986 | Mahurkar | 604/43 |
| 4,583,968 A | 4/1986 | Mahurkar | 604/43 |
| 4,623,327 A | 11/1986 | Mahurkar | 604/4 |
| 4,631,057 A | 12/1986 | Mitchell | 604/198 |
| 4,659,330 A | 4/1987 | Nelson et al. | 604/192 |
| 4,664,654 A | 5/1987 | Strauss | 604/198 |
| 4,666,435 A | 5/1987 | Braginetz | 604/198 |
| 4,692,141 A | 9/1987 | Mahurkar | 604/43 |
| 4,693,708 A | 9/1987 | Wanderer et al. | 604/198 |
| 4,702,738 A | 10/1987 | Spencer | 604/198 |
| 4,710,170 A | 12/1987 | Haber et al. | 604/110 |
| 4,731,059 A | 3/1988 | Wanderer et al. | 604/192 |
| 4,731,068 A | 3/1988 | Hesse | 604/110 |
| 4,732,162 A | 3/1988 | Martell | 128/765 |
| 4,735,617 A | 4/1988 | Nelson et al. | 604/192 |
| 4,735,618 A | 4/1988 | Hagen | 604/192 |
| 4,742,910 A | 5/1988 | Staebler | 206/365 |
| 4,746,017 A | 5/1988 | Howard et al. | 206/438 |
| 4,747,831 A | 5/1988 | Kulli | 604/110 |
| 4,747,835 A | 5/1988 | Sandhaus | 604/192 |
| 4,747,836 A | 5/1988 | Luther | 604/198 |
| 4,752,290 A | 6/1988 | Schramm | 604/198 |
| 4,762,516 A | 8/1988 | Luther et al. | 604/164 |
| 4,767,412 A | 8/1988 | Hymanson | 604/192 |
| 4,767,413 A | 8/1988 | Haber et al. | 604/198 |
| 4,770,652 A | 9/1988 | Mahurkar | 604/4 |
| 4,778,453 A | 10/1988 | Lopez | 604/110 |
| D298,352 S | 11/1988 | Raines | D24/25 |
| 4,782,841 A | 11/1988 | Lopez | 128/164 |
| 4,790,822 A | 12/1988 | Haining | 604/110 |
| 4,799,926 A | 1/1989 | Haber | 604/187 |
| 4,801,295 A | 1/1989 | Spencer | 604/198 |
| 4,808,155 A | 2/1989 | Mahurkar | 604/43 |
| 4,808,169 A | 2/1989 | Mahurkar | 604/43 |
| 4,813,426 A | 3/1989 | Haber et al. | 128/763 |
| 4,813,938 A | 3/1989 | Raulerson | 604/167 |
| 4,816,811 A | 3/1989 | Bogatin et al. | 340/712 |
| 4,819,659 A | 4/1989 | Sitar | 128/764 |
| 4,826,488 A | 5/1989 | Nelson et al. | 604/192 |
| 4,826,489 A | 5/1989 | Haber et al. | 604/195 |
| 4,826,491 A | 5/1989 | Schramm | 604/198 |
| 4,828,107 A | 5/1989 | Spencer | 209/366 |
| 4,828,548 A | 5/1989 | Walter | 604/164 |
| 4,832,696 A | 5/1989 | Luther et al. | 604/164 |
| 4,834,717 A | 5/1989 | Haber et al. | 604/193 |
| 4,838,863 A | 6/1989 | Allard et al. | 604/110 |
| 4,838,871 A | 6/1989 | Luther | 604/192 |
| 4,842,582 A | 6/1989 | Mahurkar | 604/43 |
| 4,842,591 A | 6/1989 | Luther | 604/283 |
| 4,850,961 A | 7/1989 | Wanderer et al. | 604/53 |
| 4,850,976 A | 7/1989 | Heinrich et al. | 604/192 |
| 4,852,584 A | 8/1989 | Selby | 128/760 |
| 4,860,742 A | 8/1989 | Park et al. | 128/303 |
| 4,863,435 A | 9/1989 | Sturman et al. | 604/198 |
| 4,863,436 A | 9/1989 | Glick | 604/198 |
| 4,872,552 A | 10/1989 | Unger | 206/365 |
| 4,874,382 A | 10/1989 | Lindemann et al. | 604/195 |
| 4,874,384 A | 10/1989 | Nunez | 604/198 |
| 4,883,469 A | 11/1989 | Glazier | 604/192 |
| 4,887,998 A | 12/1989 | Martin et al. | 604/110 |
| 4,892,525 A | 1/1990 | Hermann, Jr. et al. | 604/263 |
| 4,894,055 A | 1/1990 | Sudnak | 604/198 |
| 4,895,561 A | 1/1990 | Mahurkar | 604/43 |
| 4,897,083 A | 1/1990 | Martell | 604/192 |
| 4,898,588 A | 2/1990 | Roberts | 604/187 |
| 4,900,307 A | 2/1990 | Kulli | 604/110 |
| 4,900,311 A | 2/1990 | Stern et al. | 604/198 |
| 4,903,832 A | 2/1990 | Stewart | 206/366 |
| 4,906,235 A | 3/1990 | Roberts | 604/192 |
| 4,909,794 A | 3/1990 | Haber et al. | 604/195 |
| 4,911,693 A * | 3/1990 | Paris | 604/192 |
| 4,915,697 A | 4/1990 | DuPont | 604/192 |
| 4,927,019 A | 5/1990 | Haber et al. | 206/365 |
| 4,927,414 A | 5/1990 | Kulli | 604/110 |
| 4,927,417 A | 5/1990 | Moncada et al. | 604/198 |
| 4,928,824 A | 5/1990 | Barasch | 206/365 |
| 4,929,237 A | 5/1990 | Medway | 604/198 |
| 4,929,241 A | 5/1990 | Kulli | 604/263 |
| 4,931,040 A | 6/1990 | Haber et al. | 604/110 |
| 4,931,048 A | 6/1990 | Lopez | 604/110 |
| 4,932,940 A | 6/1990 | Walker et al. | 604/110 |
| 4,932,946 A | 6/1990 | Shields | 604/198 |
| 4,935,015 A | 6/1990 | Hall | 604/195 |
| 4,944,723 A | 7/1990 | Haber et al. | 604/110 |
| 4,944,728 A | 7/1990 | Carrell et al. | 604/164 |
| 4,944,731 A | 7/1990 | Cole | 604/192 |
| 4,946,447 A | 8/1990 | Hardcastle et al. | 604/198 |
| 4,950,241 A | 8/1990 | Ranford | 604/110 |
| 4,950,252 A | 8/1990 | Luther et al. | 604/198 |
| 4,958,622 A | 9/1990 | Selenke | 128/765 |
| 4,964,854 A | 10/1990 | Luther | 604/166 |
| 4,973,316 A | 11/1990 | Dysarz | 604/195 |
| 4,976,702 A | 12/1990 | Andrews et al. | 604/198 |
| 4,978,343 A | 12/1990 | Dysarz et al. | 604/195 |
| 4,986,813 A | 1/1991 | Blake, III et al. | 604/110 |
| 4,986,819 A | 1/1991 | Sobel | 604/198 |
| 4,988,339 A | 1/1991 | Vadher | 604/197 |
| 4,994,042 A | 2/1991 | Vadher | 604/165 |
| 4,994,044 A | 2/1991 | Lo Duca | 604/192 |
| 4,997,422 A | 3/1991 | Chow et al. | 604/198 |
| 5,000,167 A | 3/1991 | Sunderland | 128/763 |
| 5,002,536 A | 3/1991 | Thompson et al. | 604/192 |
| 5,013,304 A | 5/1991 | Russell et al. | 604/167 |
| 5,015,241 A | 5/1991 | Feimer | 604/198 |
| 5,019,044 A | 5/1991 | Tsao | 604/110 |
| 5,019,045 A | 5/1991 | Lee | 604/110 |
| 5,019,051 A | 5/1991 | Hake | 604/198 |
| 5,024,326 A | 6/1991 | Sandel | 206/366 |
| 5,024,660 A | 6/1991 | McNaughton | 604/110 |
| 5,026,345 A | 6/1991 | Teringo | 604/110 |
| 5,026,354 A | 6/1991 | Kocses | 604/195 |
| 5,030,209 A | 7/1991 | Wanderer et al. | 604/198 |
| 5,030,212 A | 7/1991 | Rose | 604/263 |
| 5,037,400 A | 8/1991 | Curry | 604/192 |
| 5,037,401 A | 8/1991 | DeCamp | 604/192 |
| 5,045,062 A | 9/1991 | Henson | 604/110 |
| 5,046,508 A | 9/1991 | Weissler | 128/763 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,057,088 A | 10/1991 | Narayanan | 604/198 |
| 5,057,089 A | 10/1991 | Greco | 604/198 |
| 5,059,180 A | 10/1991 | McLees | 604/110 |
| 5,061,249 A | 10/1991 | Campbell | 604/195 |
| 5,066,279 A | 11/1991 | Russell | 604/110 |
| 5,066,281 A | 11/1991 | Stevenson-Michener | 604/110 |
| 5,067,942 A | 11/1991 | Jaffe et al. | 604/110 |
| 5,067,944 A | 11/1991 | Nichols | 604/192 |
| 5,067,946 A | 11/1991 | Zhadanov | 604/198 |
| 5,067,949 A | 11/1991 | Freundlich et al. | 604/263 |
| 5,069,669 A | 12/1991 | Kole | 604/198 |
| 5,078,693 A | 1/1992 | Shine | 604/192 |
| 5,084,019 A | 1/1992 | Gartz | 604/110 |

| | | | |
|---|---|---|---|
| 5,084,029 A | 1/1992 | Nacci nee Tagliaferri et al. | 604/195 |
| 5,086,780 A | 2/1992 | Schmitt | 128/763 |
| 5,088,987 A | 2/1992 | Noonan, Jr. | 604/195 |
| 5,088,988 A | 2/1992 | Talonn et al. | 604/198 |
| 5,092,853 A | 3/1992 | Couvertier, II | 604/195 |
| 5,098,394 A | 3/1992 | Luther | 604/167 |
| 5,098,402 A | 3/1992 | Davis | 604/195 |
| 5,098,405 A | 3/1992 | Peterson et al. | 604/247 |
| 5,106,379 A | 4/1992 | Leap | 604/198 |
| 5,106,380 A | 4/1992 | Lobello | 604/198 |
| 5,108,378 A | 4/1992 | Firth | 604/192 |
| 5,112,307 A | 5/1992 | Haber et al. | 604/110 |
| 5,112,315 A | 5/1992 | Gloyer et al. | 604/195 |
| 5,112,316 A | 5/1992 | Venturini | 604/195 |
| 5,114,404 A | 5/1992 | Paxton et al. | 604/110 |
| 5,116,319 A | 5/1992 | van den Haak | 604/110 |
| 5,116,325 A | 5/1992 | Paterson | 604/192 |
| 5,120,309 A | 6/1992 | Watts | 604/110 |
| 5,122,118 A | 6/1992 | Haber et al. | 604/110 |
| 5,125,898 A | 6/1992 | Kaufhold, Jr. et al. | 604/110 |
| 5,127,910 A | 7/1992 | Talonn et al. | 604/198 |
| 5,135,504 A | 8/1992 | McLees | 604/164 |
| 5,135,505 A | 8/1992 | Kaufman | 604/165 |
| 5,135,510 A | 8/1992 | Maszkiewicz et al. | 604/195 |
| 5,147,303 A | 9/1992 | Martin | 604/110 |
| 5,147,326 A | 9/1992 | Talonn et al. | 604/198 |
| 5,160,326 A | 11/1992 | Taolonn et al. | 604/198 |
| 5,163,908 A | 11/1992 | Lambert | 604/110 |
| 5,163,917 A | 11/1992 | Huefner et al. | 604/198 |
| 5,171,300 A | 12/1992 | Blake, III et al. | 604/110 |
| 5,171,303 A | 12/1992 | DeCamp | 604/192 |
| 5,176,640 A | 1/1993 | Nacci et al. | 604/110 |
| 5,176,655 A | 1/1993 | McCormick et al. | 604/198 |
| 5,181,524 A | 1/1993 | Wanderer et al. | 128/764 |
| 5,183,468 A | 2/1993 | McLees | 604/164 |
| 5,188,119 A | 2/1993 | Sunderland | 128/763 |
| 5,188,611 A | 2/1993 | Orgain | 604/192 |
| 5,188,613 A | 2/1993 | Shaw | 604/195 |
| 5,190,526 A | 3/1993 | Murray et al. | 604/110 |
| 5,190,532 A | 3/1993 | Yu | 604/192 |
| 5,195,973 A | 3/1993 | Novick | 604/110 |
| 5,195,975 A | 3/1993 | Castagna | 604/110 |
| 5,195,982 A | 3/1993 | Hoenig | 604/192 |
| 5,195,983 A | 3/1993 | Boese | 604/192 |
| 5,195,992 A | 3/1993 | Dudar et al. | 604/283 |
| 5,195,993 A | 3/1993 | Gianakos | 604/283 |
| 5,197,951 A | 3/1993 | Mahurkar | 604/283 |
| 5,197,953 A | 3/1993 | Colonna | 604/110 |
| 5,197,954 A | 3/1993 | Cameron | 604/110 |
| 5,201,718 A | 4/1993 | Whisson | 604/194 |
| 5,215,524 A | 6/1993 | Vallelunga et al. | 604/110 |
| 5,215,525 A | 6/1993 | Sturman | 604/164 |
| 5,215,528 A | 6/1993 | Purdy et al. | 604/164 |
| 5,215,529 A | 6/1993 | Fields et al. | 604/168 |
| 5,215,533 A | 6/1993 | Robb | 604/195 |
| 5,215,534 A | 6/1993 | De Harde et al. | 604/198 |
| 5,215,535 A | 6/1993 | Gettig et al. | 604/198 |
| 5,217,436 A | 6/1993 | Farkas | 604/187 |
| 5,217,437 A | 6/1993 | Talonn et al. | 604/198 |
| 5,218,965 A | 6/1993 | Ring | 128/673 |
| 5,219,333 A | 6/1993 | Sagstetter et al. | 604/110 |
| 5,219,338 A | 6/1993 | Haworth | 644/198 |
| 5,221,255 A | 6/1993 | Mahurkar et al. | 604/43 |
| 5,221,256 A | 6/1993 | Mahurkar | 604/43 |
| 5,221,262 A | 6/1993 | Kite | 604/110 |
| 5,222,942 A | 6/1993 | Bader | 604/110 |
| 5,222,943 A | 6/1993 | Mazzara | 604/110 |
| 5,222,944 A | 6/1993 | Harris | 604/110 |
| 5,222,945 A | 6/1993 | Basnight | 604/110 |
| 5,222,947 A | 6/1993 | D'Amico | 604/198 |
| 5,273,541 A | 12/1993 | Malenchek | 604/110 |
| 5,324,265 A | 6/1994 | Murray et al. | 604/110 |
| 5,330,440 A | 7/1994 | Stanners et al. | 604/195 |
| 5,338,311 A | 8/1994 | Mahurkar | 604/195 |
| 5,342,308 A | 8/1994 | Boschetti | 604/110 |
| 5,374,245 A | 12/1994 | Mahurkar | 604/43 |
| 5,378,230 A | 1/1995 | Mahurkar | 604/43 |
| 5,380,296 A | 1/1995 | Smedley et al. | 604/193 |
| 5,395,337 A | 3/1995 | Clemens et al. | 604/110 |
| 5,486,159 A | 1/1996 | Mahurkar | 604/4 |
| 5,514,100 A | 5/1996 | Mahurkar | 604/195 |
| 5,531,694 A * | 7/1996 | Clemens et al. | 604/110 |
| 5,562,624 A | 10/1996 | Righi et al. | 604/110 |
| 5,562,626 A | 10/1996 | Sanpietro | 604/110 |
| 5,613,952 A | 3/1997 | Pressly, Sr. et al. | 604/110 |
| 5,643,222 A | 7/1997 | Mahurkar | 604/195 |
| 5,685,862 A | 11/1997 | Mahurkar | 604/194 |
| 5,695,475 A | 12/1997 | Best, Jr. et al. | 604/198 |
| 5,836,921 A | 11/1998 | Mahurkar | 604/195 |
| 5,876,382 A * | 3/1999 | Erickson | 604/198 |
| 5,879,338 A | 3/1999 | Mahurkar | 604/195 |
| 5,885,257 A | 3/1999 | Badger | 604/195 |
| 5,891,105 A | 4/1999 | Mahurkar | 604/195 |
| 5,911,705 A * | 6/1999 | Howell | 604/110 |
| 6,106,500 A | 8/2000 | Mahurkar | 604/195 |
| 6,117,112 A | 9/2000 | Mahurkar | 604/194 |
| 6,156,013 A * | 12/2000 | Mahurkar | 604/195 |
| 6,206,856 B1 * | 3/2001 | Mahurkar | 604/195 |

FOREIGN PATENT DOCUMENTS

| | | |
|---|---|---|
| DE | 2415196 | 10/1975 |
| DE | 2507119 | 9/1976 |
| DE | 3042229 | 5/1982 |
| DE | 3833138 | 4/1990 |
| EP | 0824932 A2 | 8/1987 |
| EP | 0360313 | 3/1990 |
| EP | 0360313 B1 | 7/1993 |
| EP | 0566882 A1 | 10/1993 |
| EP | 0677298 A1 | 10/1995 |
| EP | 0754469 A2 | 6/1996 |
| EP | 1317938 B1 | 7/2006 |
| FR | 2004771 | 11/1969 |
| WO | WO 84/01510 | 4/1984 |
| WO | WO 90/15634 | 12/1990 |
| WO | WO 91/11212 | 8/1991 |
| WO | WO 93/00950 | 1/1993 |
| WO | WO 95/30445 | 11/1995 |
| WO | WO 96/05879 | 2/1996 |
| WO | WO 97/06841 | 2/1997 |

OTHER PUBLICATIONS

The GMP Letter (May 1992).
Devices & Diagnostics Letter, vol 19., No. 19 (May 8, 1992).
FDA Medical Bulletin, vol. 22, No. 2 (Sep. 22, 1992).
"Safer Syringes Boost Molder Opportunities" by Karl Kirkland, Plastic World, vol. 51, No. 8, pp. 20/24, (Aug. 1993).
"Ultrasonics Get Medical Seal of Approval," by Marcie Moskowitz, Plastic World, vol. 51, No. 8, pp. 26-28, (Aug. 1993).
Brochure for Arrow® Revlerson Syringe.
Brochure for Syringes by Becton Dickinson of Franklin Lakes, New Jersey (1992).
Devices & Diagnostics Letter, p. 2 (Aug. 21, 1992).
Chiarella, Linda A, "Reducing Needlestick Injuries amoung Health Care Workers" AIDS Clinical Care, Oct. 1993, V. 5, No. 10, Mass Medical Safety.

* cited by examiner

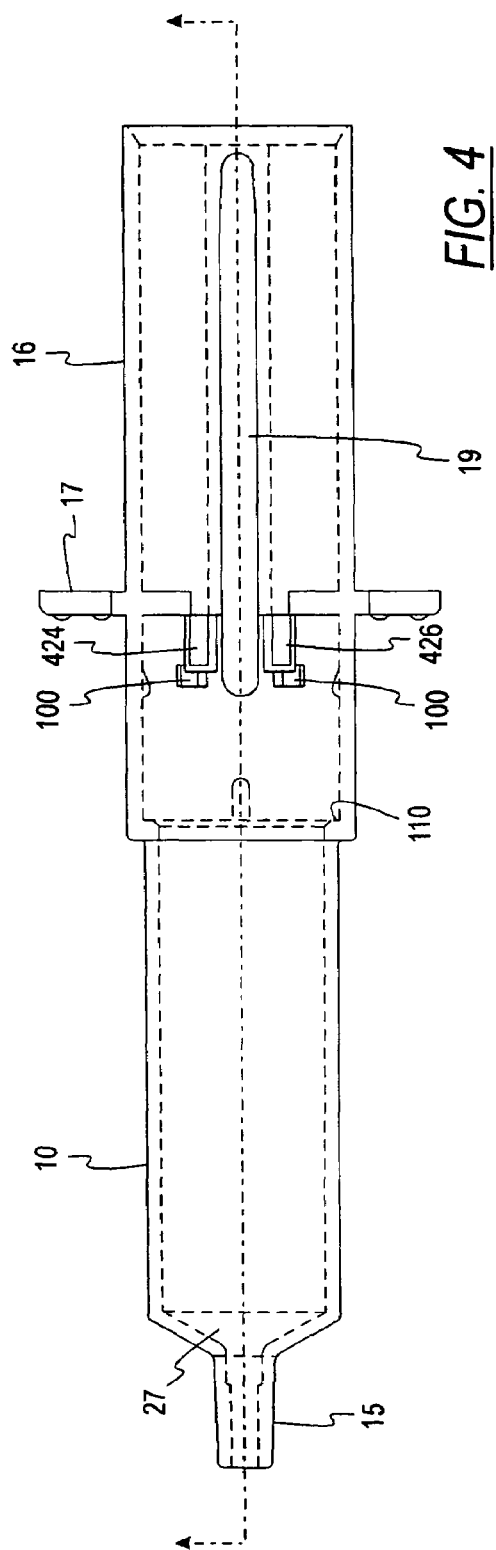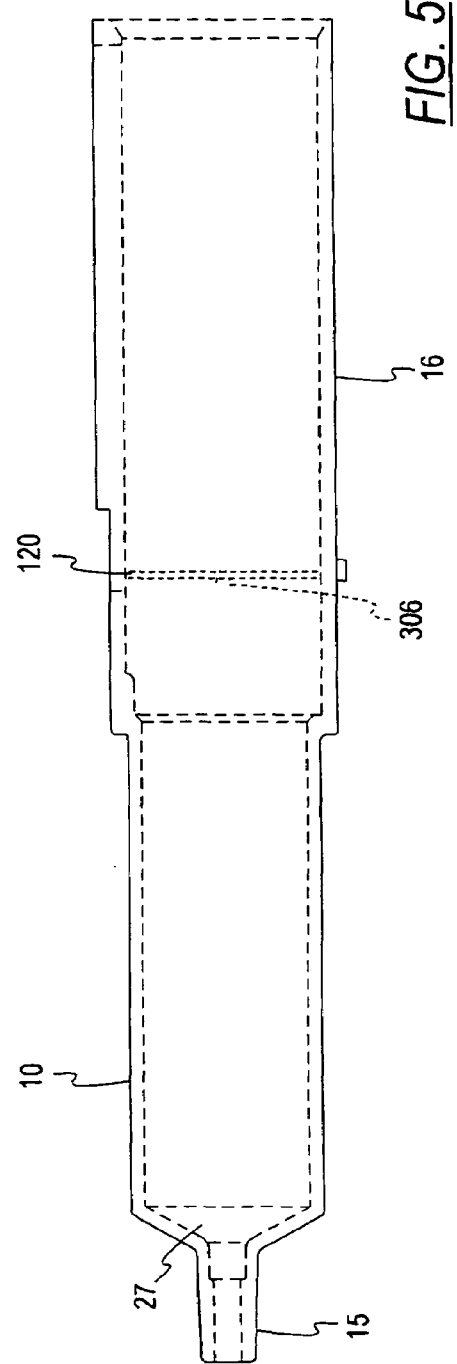

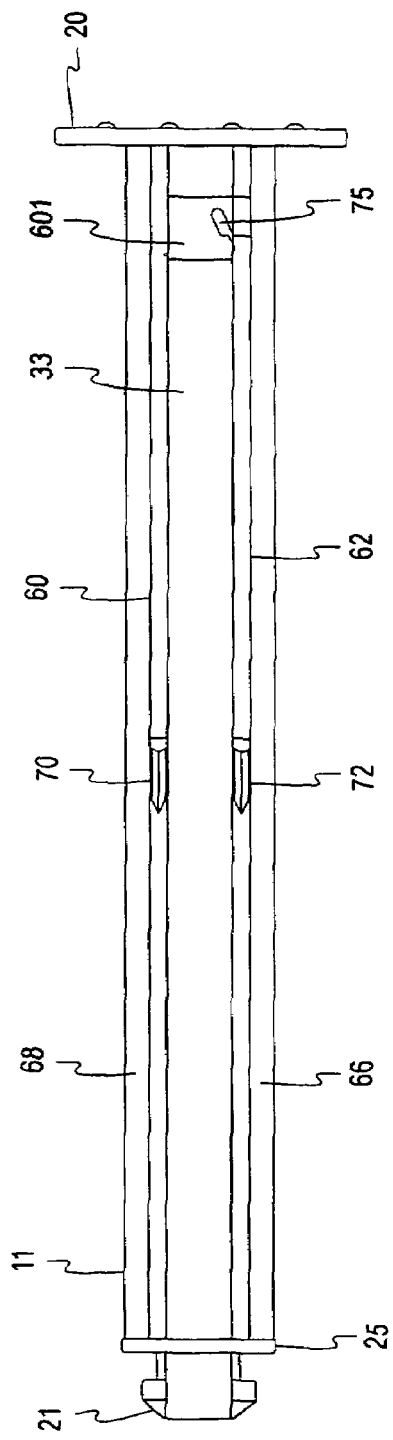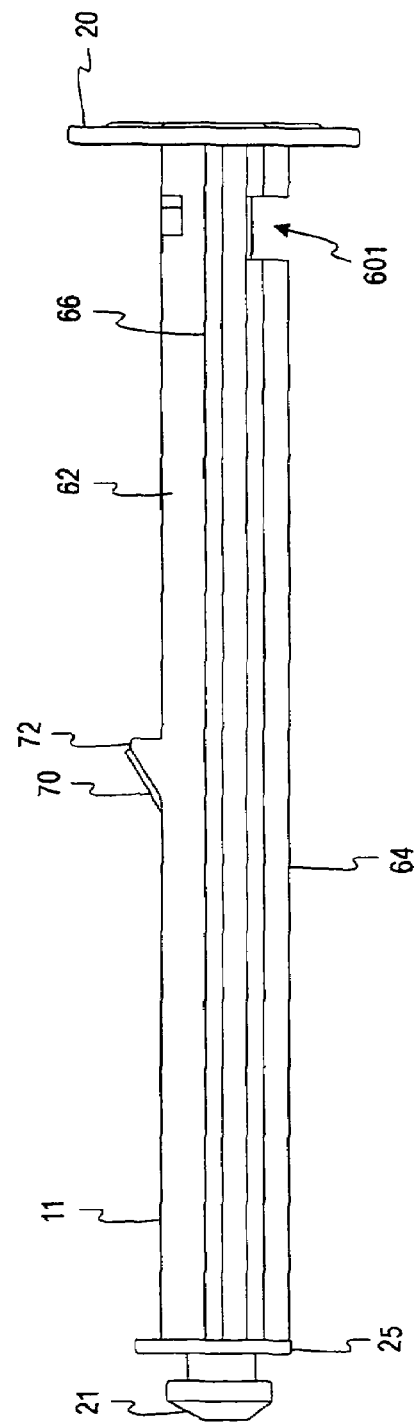

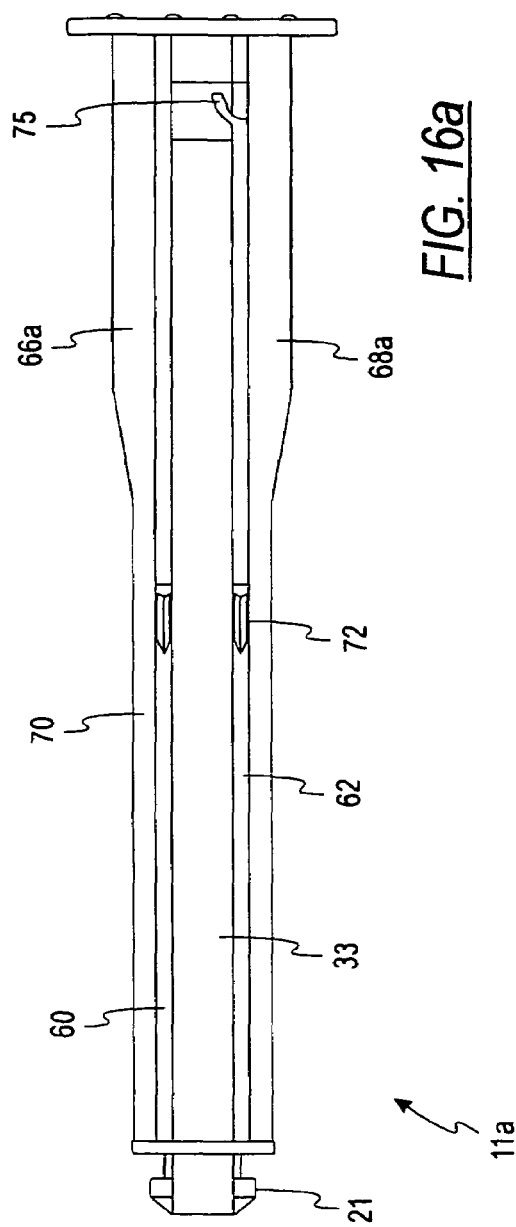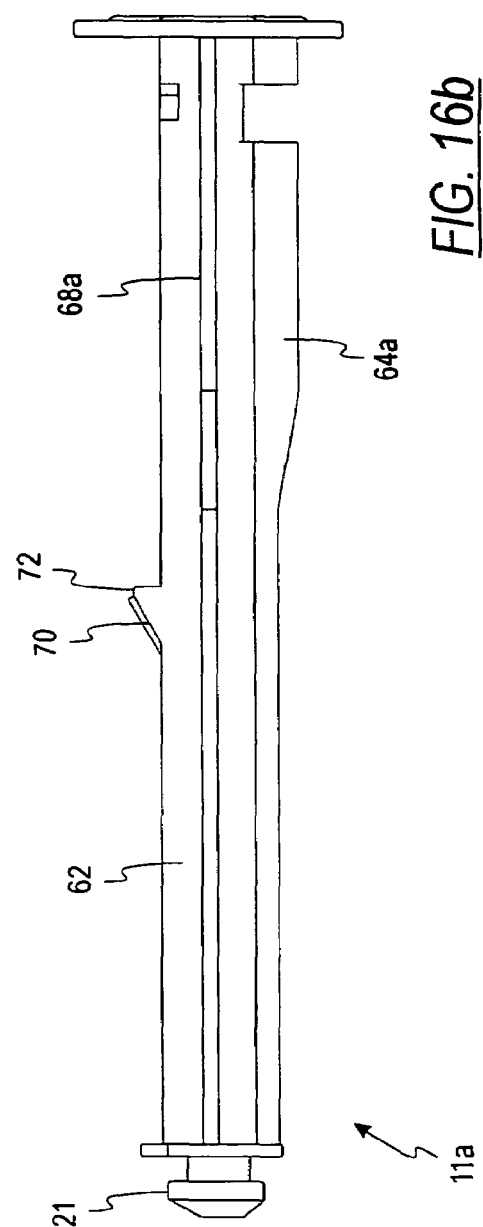

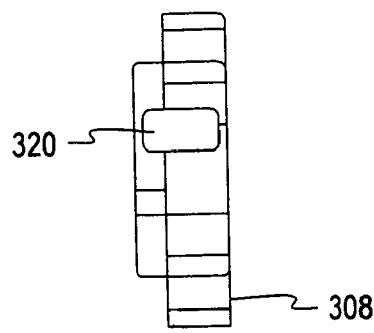
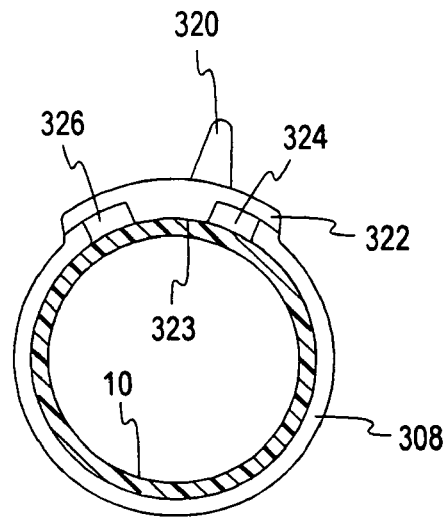
FIG. 23  FIG. 24
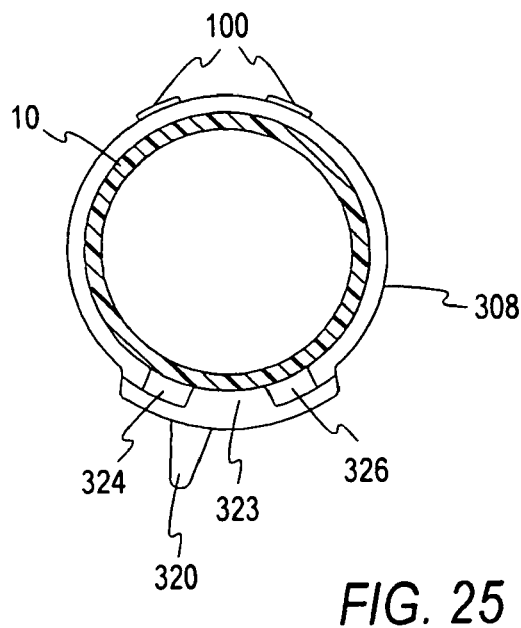
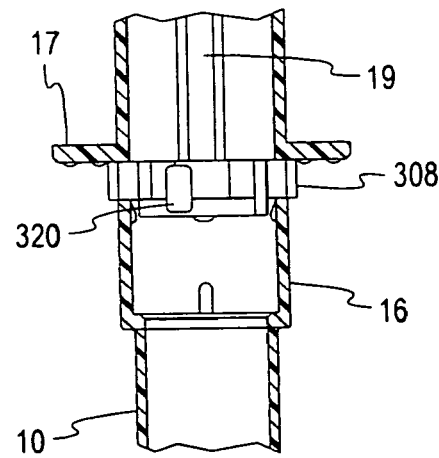
FIG. 25  FIG. 26

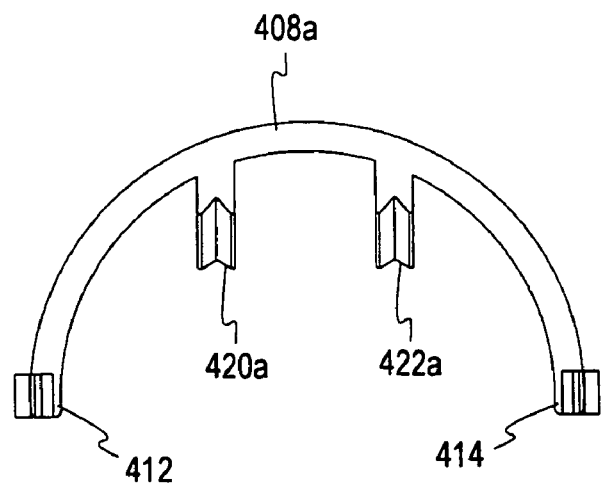
FIG. 31a
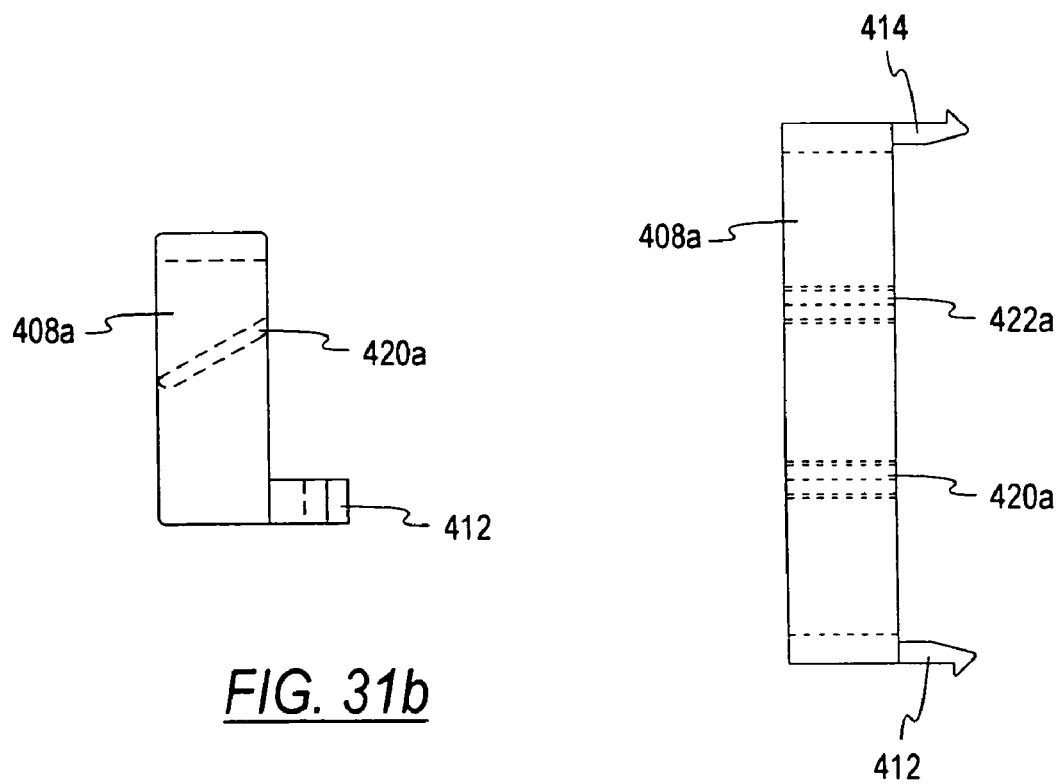
FIG. 31b
FIG. 31c

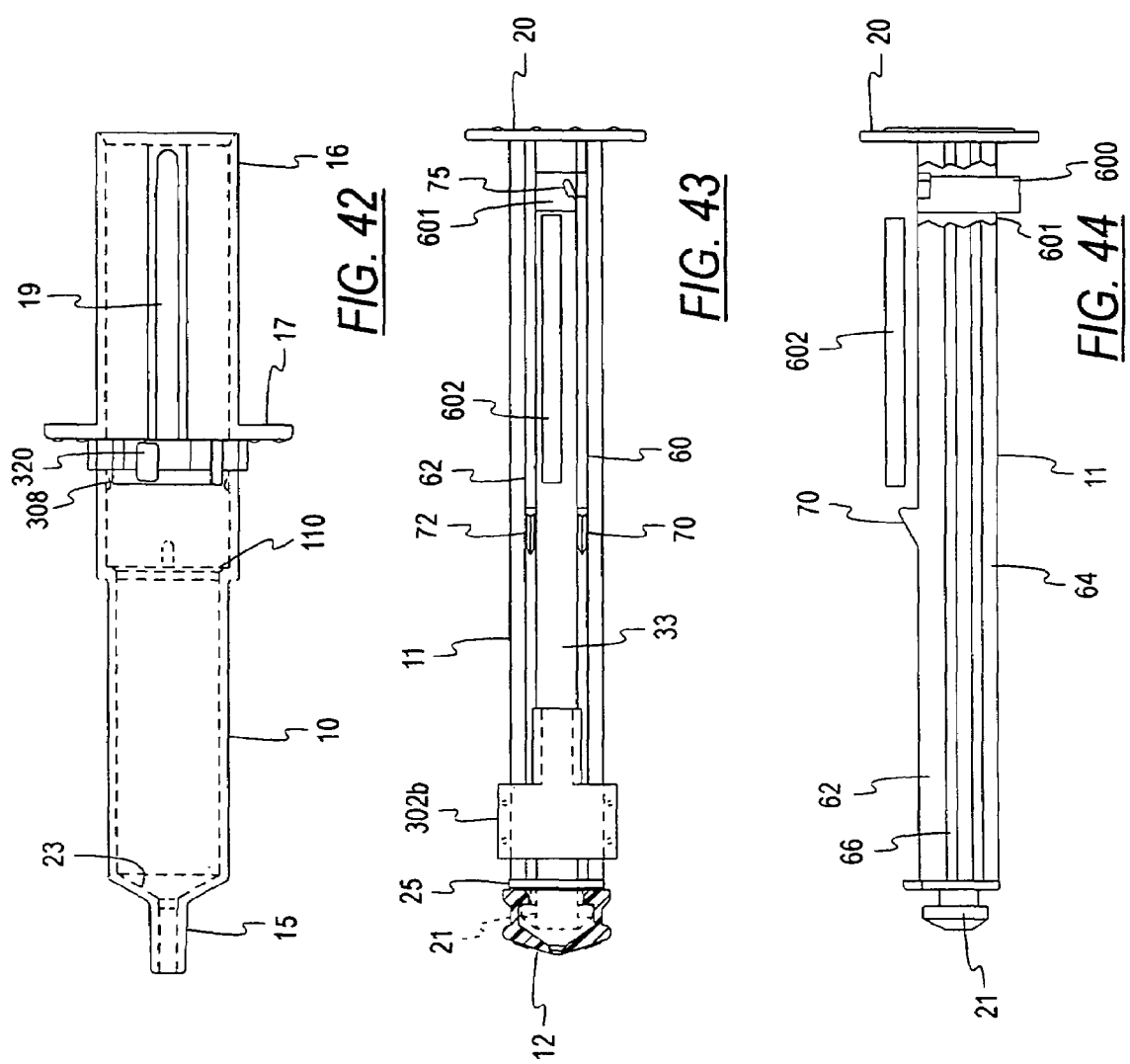

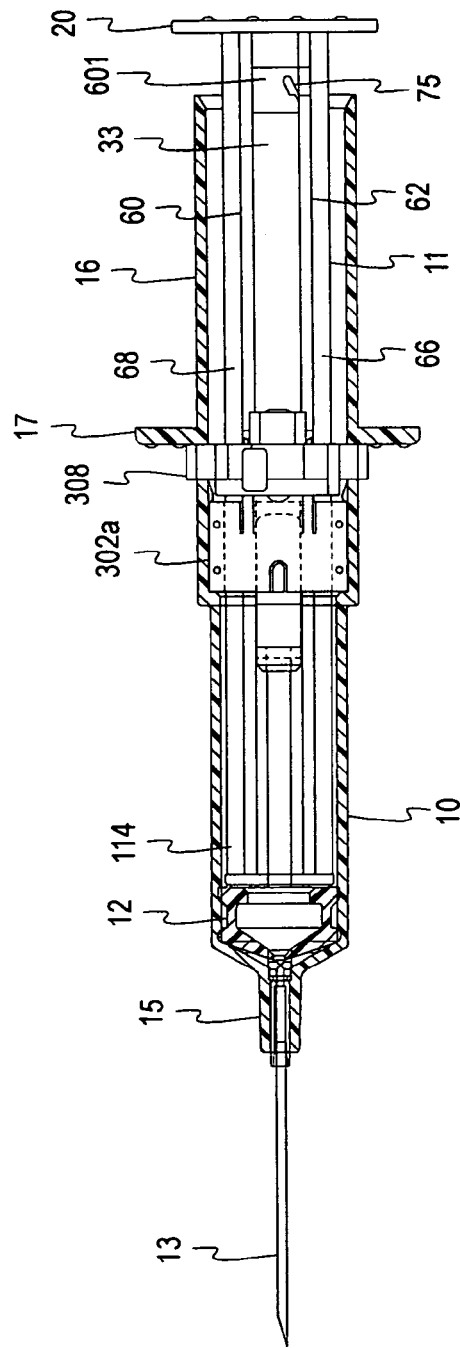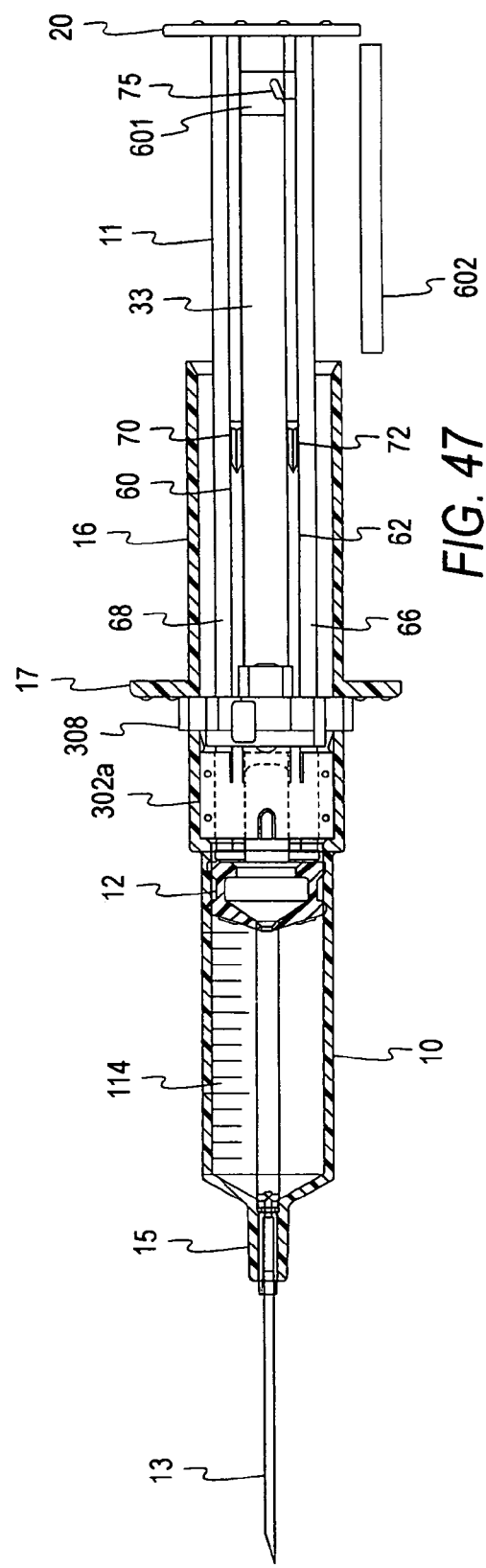

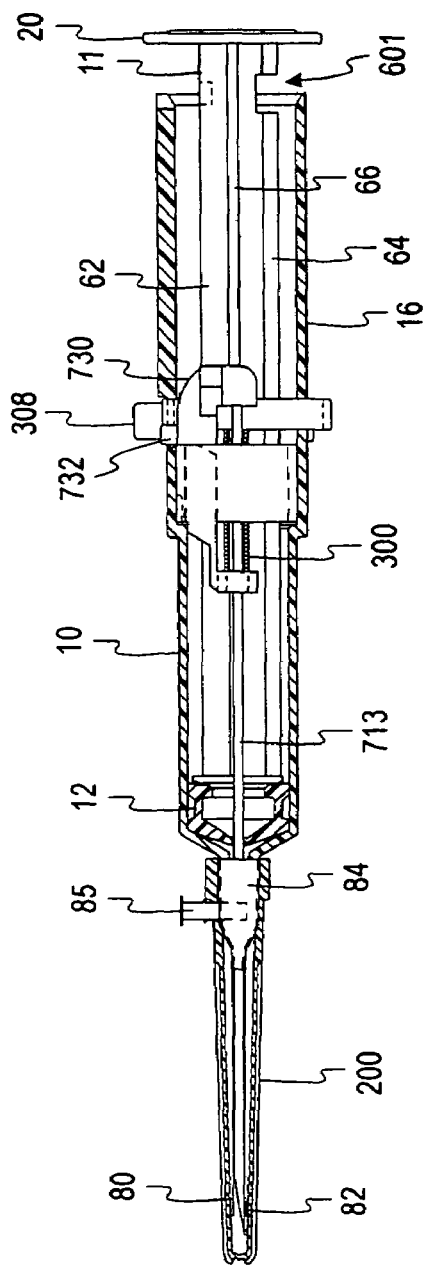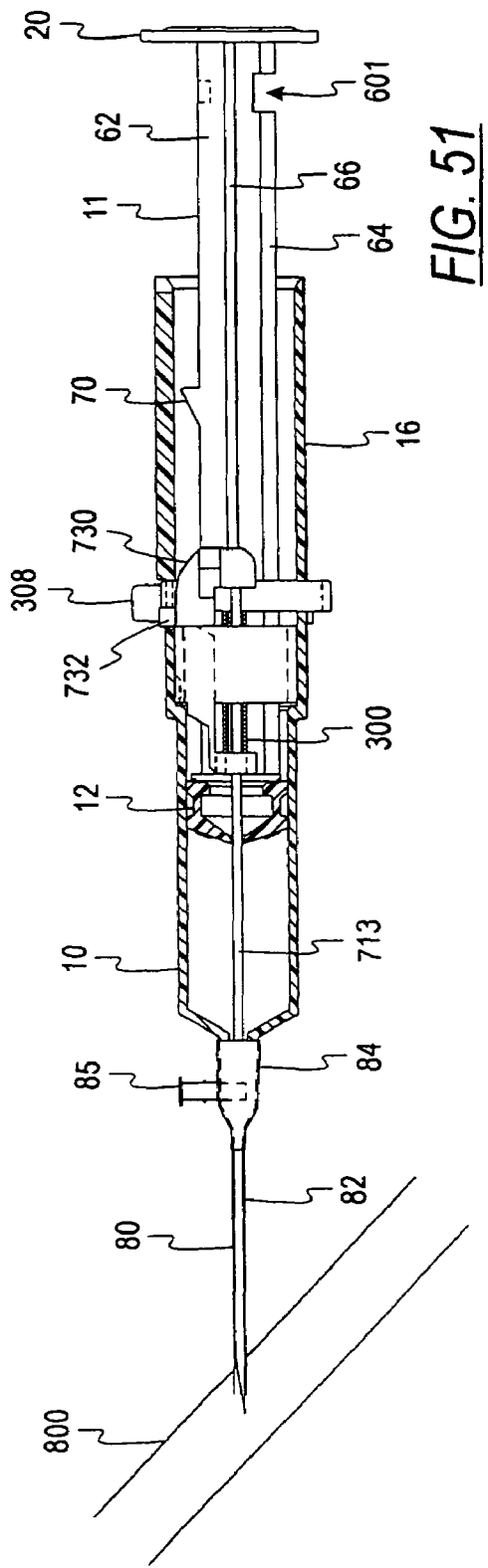

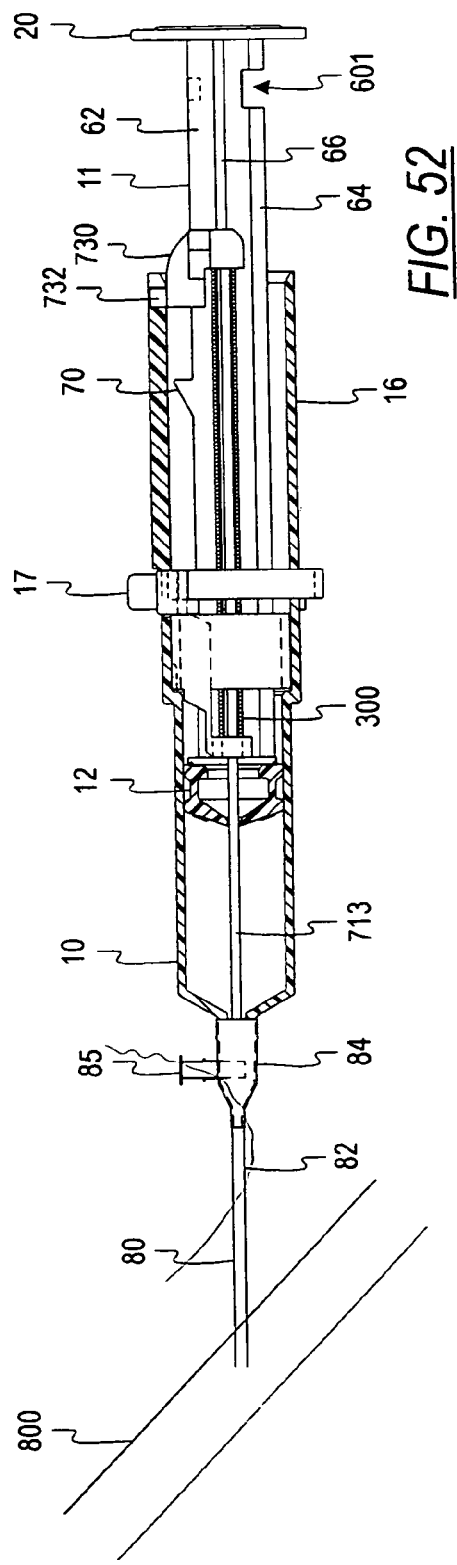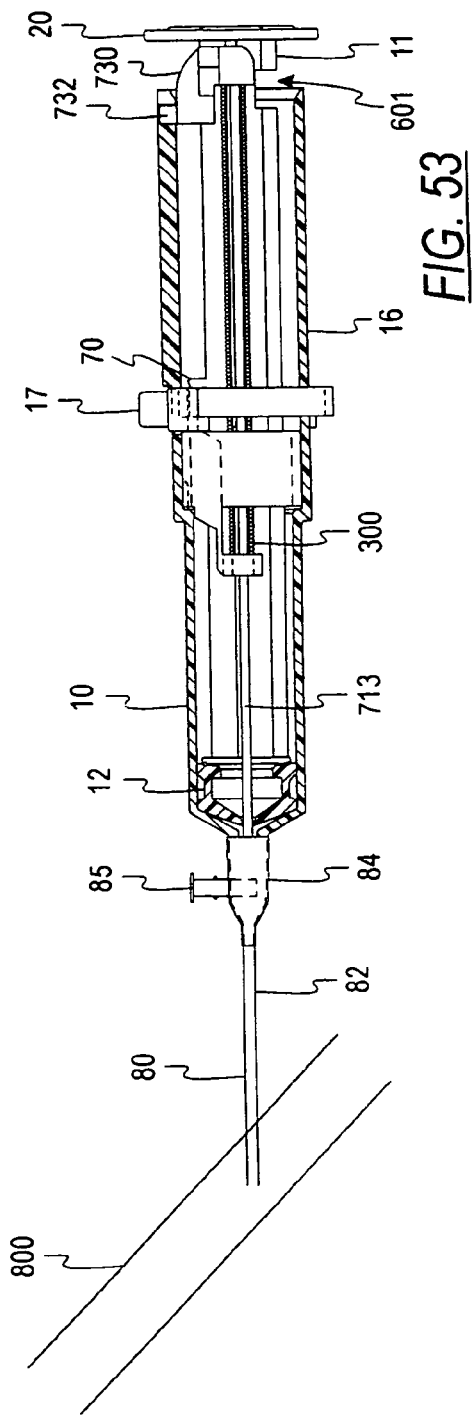

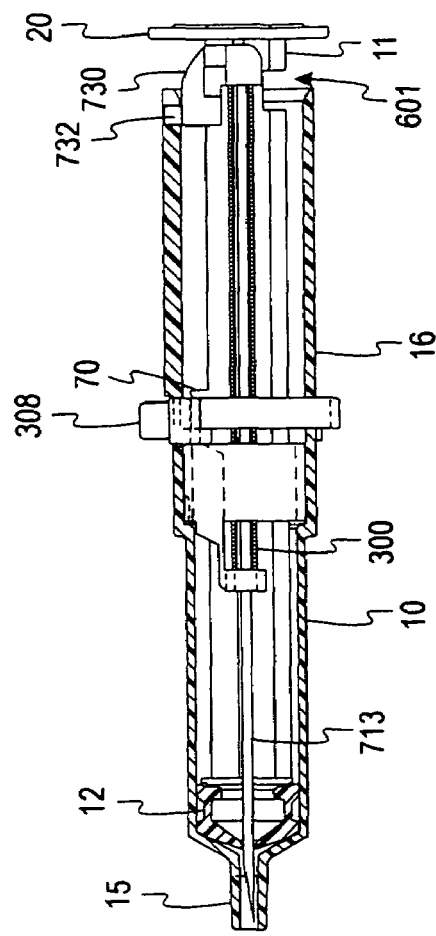
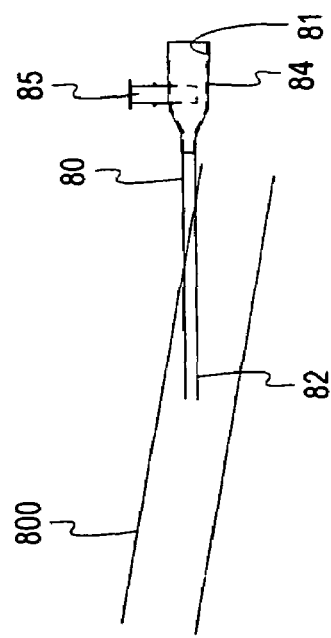
FIG. 54

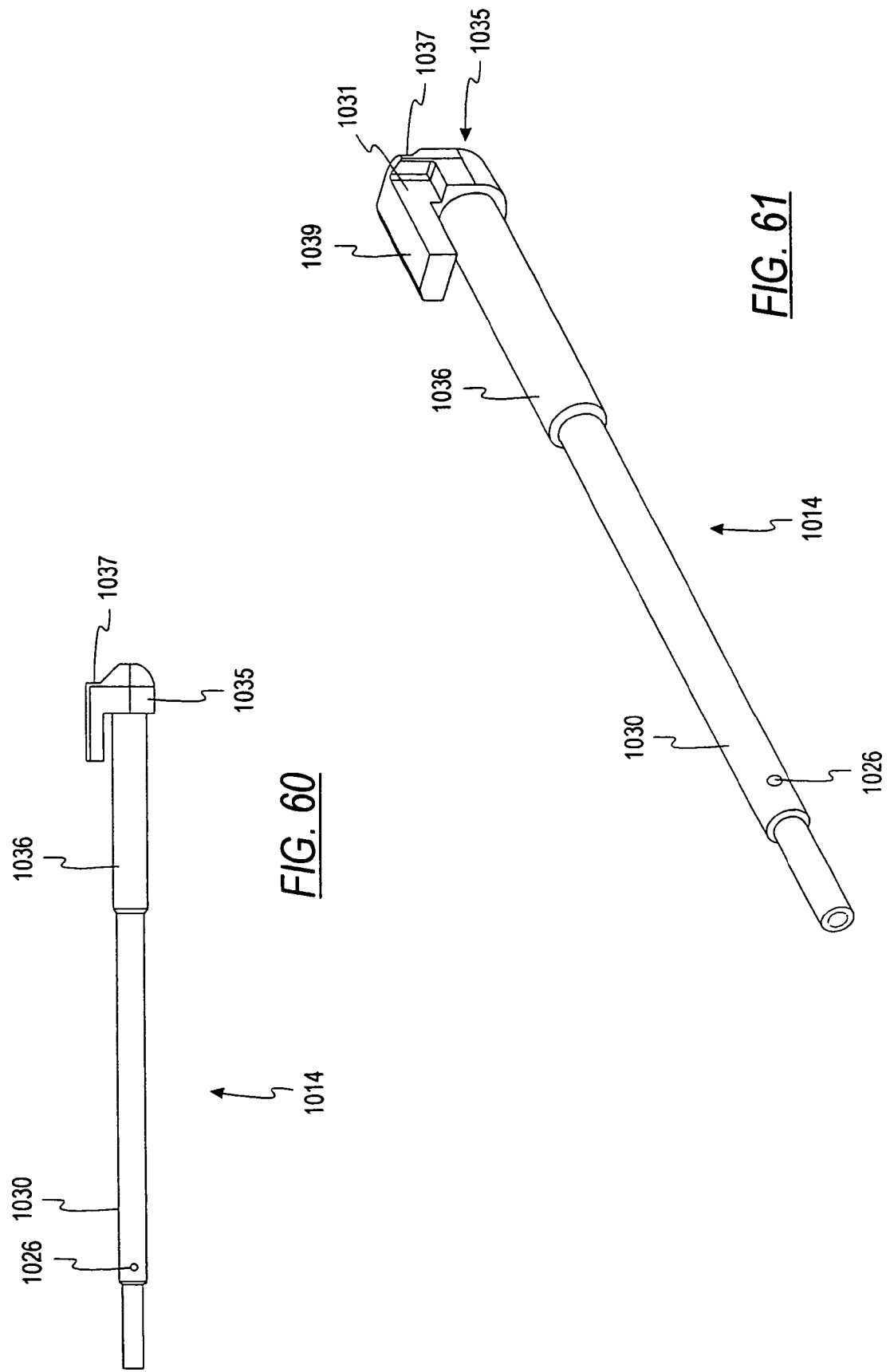

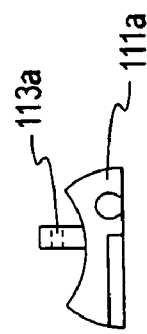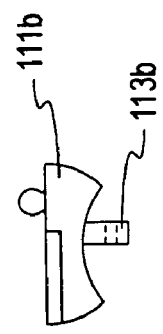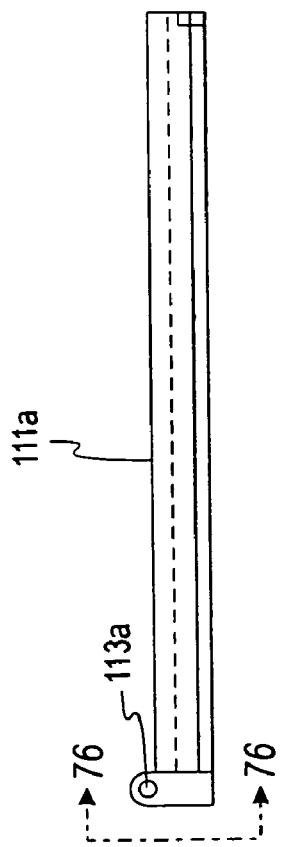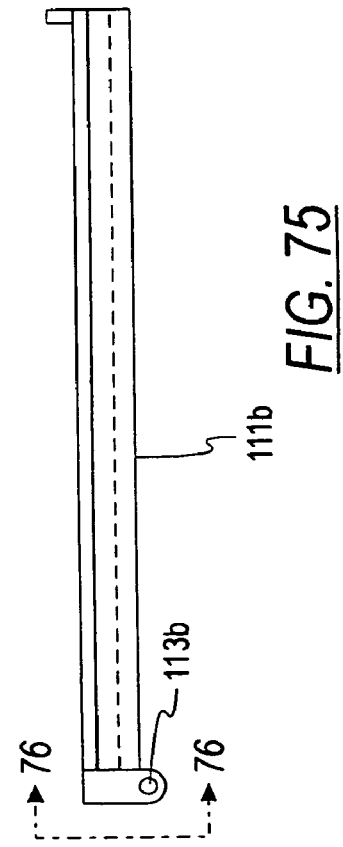
FIG. 76
FIG. 75

RETRACTABLE NEEDLE SINGLE USE SAFETY SYRINGE

CROSS-REFERENCE TO RELATED APPLICATION

This application is a continuation of U.S. patent application Ser. No. 10/051,140, filed Jan. 22, 2002, now abandoned, which claims the benefit of priority of U.S. Provisional Patent Application No. 60/333,721, filed Nov. 28, 2001.

FIELD OF THE INVENTION

The present invention generally relates to syringes for use with hypodermic needles. In particular, the present invention relates to a needle-syringe assembly which withdraws the sharp point of the hypodermic needle following, use so as to render it non-reusable. An over-the-needle (OTN) catheter may also be used with the syringe assembly of the invention.

BACKGROUND OF THE INVENTION

A hypodermic needle has many applications in modern medicine. One application is to fit the hypodermic needle onto a syringe and to then insert the needle into a person's body for intra-muscular, subcutaneous, or intravenous injection of medications. Another application of the hypodermic needle is to coaxially mount a catheter over a hypodermic needle and to puncture a vein of a person's body with the needle. Following needle puncture, the over-the-needle (OTN) catheter is advanced into and retained in the vein, the needle is removed, and the catheter is connected to an intravenous line for fluid infusions into the vein.

A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidentally puncture them. Thus, health care personnel are in constant danger of contracting infections and diseases, some of which may be deadly. Other potential victims of accidental needle punctures include sanitation workers who later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

Many existing OTN catheters suffer from penetration problems because of long length needles and unsecured needle supports. In addition, many existing OTN catheters still present the danger of causing needle pricks due to ineffective encasement of the puncturing needles following use.

The impact of needle stick injuries has shaken the healthcare industry. Several new products have been introduced and their disadvantages are now becoming apparent. An inventive improvement is required to remove these disadvantages.

The United States Congress has passed "Needle Stick Safety and Prevention Act (H.R.5178.ENR)". The President has signed the bill into law that Is effective Apr. 18, 2002. The law, FDA, OSHA, Center For Disease Control, National Institute for Occupational Safety and Health and other regulatory bodies have also mandated and/or recommend several improvements in syringes.

It will be clear from the reading of the disclosure that the present invention does possess all the improvements deemed mandatory and/or recommended by regulatory agencies.

A number of improvements required and/or recommended by health care regulatory bodies contained in the present invention are listed below.

1. The syringe as well as retraction mechanism should be single hand operable, sparing another hand of physician for additional tasks. [Improved Industry Standard]

2. The switches and functional components are inseparable from the syringe and available in any emergencies. [Improved Industry Standard]

3. Activation of the retraction mechanism must occur from proximal plunger end. [Improved Industry Standard]

4. The worker's hand must remain behind the needle as it is covered. (FDA guidance on 510(k) Submission March 1995)

5. The safety feature must be an integral part of the device. (FDA guidance on 510(k) Submission March 1995)

6. The safety feature remains activated before disassembly and disposal. (FDA guidance on 510(k) Submission March 1995)

7. The safety feature should be simple and should require as little or no user action or training to use it safely and effectively. (FDA guidance on 510(k) Submission March 1995)

8. The safety feature is an integral part of the device. National Institute of Occupational Safety and health (NIOSH) desirable characteristics DHHS (NIOSH) alert. Publication No. 2000-108, November 99

9. The device preferably works passively. DHHS (NIOSH) alert. Publication No. 2000-108, November 99

10. The user can easily tell whether the safety feature is activated. DHHS (NIOSH) alert. Publication No. 2000-108, November 99

11. The safety feature cannot be deactivated and remains protective through disposal DHHS (NIOSH) alert. Publication No. 2000-108, November 99

12. The device performs reliably. DHHS (NIOSH) alert. Publication No. 2000-108, November 99

13. The device is easy to use and practical. DHHS (NIOSH) alert. Publication No. 2000-108, November 99

14. The device is safe and effective for patient care. DHHS (NIOSH) alert. Publication No. 2000-108, November 99.

15. Cost reduction by avoiding sharp container requirement for non-safe syringes Government Regulatory Agencies mandate use of the "sharp containers" at hospitals, physician offices and clinics as well as emergency rooms. These containers are strong steel boxes with a one way window through which used non-safety syringe and needles are dropped. The sharp protection service is operated by licensed companies that pick up the contents of the "Sharp containers" and dispose them at specially run facilities. This service is expensive and impacts on the cost of health care. Two safety syringes currently on the market do retract the needles after use, however the retracted needle and spring freely floats within the plunger cavity. If by chance the plunger is pulled off by minimum efforts the potential of needle stick injury does exist. FDA requires sharp containers for these because there is a chance of the needle stick injury. It adds to the expense.

One purpose of inventing the present safety syringe is to lock the retracted needle securely within the interlocked syringe itself rather than sharp container and save the expense. It is essential that the entire syringe must be interlocked and disposed off in biological recyclable waste to avoid the expense of sharp container fees. This objective is incorporated in the present invention 16. Premature disablement of devices. Advance of plunger in the barrel is a normal function of the syringe to inject the medicine. However in two devices on market retraction of the needle and disablement of syringe results from advance of the plunger within the barrel cavity, even before physician has a chance to use the syringe for patient. The syringe is wasted. The safety mechanism incorporated in the present invention and procedure of use avoids this accidental retraction and disablement.

17. Low dead space. At the end of the injection, medicine still remains within the nozzle and the female luer end. The cost of biotechnology medicines such as Epo, and newer insulins are very high and wastage is unacceptable. The present invention avoids the female luer connector that connects hypodermic needle with the nozzle—the cause of dead space.

18. Aerosolization. In certain devices on the market, after the injection of the medicine and advance of the plunger, a spring is released and the needle and spring flies back within the air-filled plunger. When the needle shoots back the air escapes out through the open needle due to the backward momentum and causes the fluid/medicine to escape from the needle. The escaping fluid may be contaminated.

The FDA has allowed the use of such syringes only for intra-muscular and subcutaneous application. Further it requires on use of such syringes that the retraction must be initiated and completed when the needle of the syringe is still within the body of the patient.

In the present invention the proximal end of the needle is closed and glued to the needle holder. Further the exit and entry of the fluid occurs at the peripheral wall of the needle, which is a zero velocity zone during needle retraction, and heavy construction. Also, the weight of the needle holder arm dampens the retroactive velocity of the needle. A reactive aerosolization is therefore not likely to occur, i.e., the present invention avoids aerosol problems.

19. Hydraulic disablement. Robust design of the present invention prevents disablement of retractable needle syringe that could result from increased hydraulic pressure inside the barrel.

Accordingly, there exists a need for a hypodermic needle assembly which overcomes the above-noted drawbacks associated with many existing assemblies.

The problem of suffering accidental needle punctures is well recognized. As a result, enormous inventive effort has been devoted to concealing the sharp needle point of hypodermic needles. Such efforts are described in the present applicant's U.S. Pat. No. 5,338,311, issued Aug. 16, 1994 and U.S. Pat. No. 6,156,013, issued Dec. 5, 2000.

Apart from the above patents, in certain of the syringes that are in the market, the hypodermic needle is assembled within the compression spring and installed in the nozzle of the syringe by a bushing or "O" ring. After injection of the medicine the bushing is displaced forward by plunger end. The displacement of the bushing releases the spring and the needle as well as the plug in the plunger cavity. The retracted spring, hypodermic needle and plug freely float in the plunger.

In situations (1) when the plunger is pushed fast before medicine could escape, (2) When the medicine is viscous and needs higher gradient to escape through the needle, (3) when the needle is thin and offers resistance, (4) when there is partial block in needle or has been inserted in thick tissue, hydraulic force generated in barrel displaces the bushing causes retraction. This happens even though plunger is not advanced and medicine is still in the syringe. The present invention prevents this mishap because of mechanical continuity and robust design.

SUMMARY OF THE INVENTION

One aspect of this invention comprises an improved needle-syringe assembly which provides a simple and reliable mechanism to retract the needle after it has been used.

One aspect of the present invention was to identify the retraction control mechanism from the conventional hypodermic injection syringe, minimally supplement it with needed components, and systematically modify existing components of the syringe while preserving their normal function yet recruiting them to transform into a precision needle retraction syringe machine. Functional elements assembled with a spring retainer and plunger become a retraction control module to be installed in a conventional barrel. Indirect coupling of a needle holder to the barrel via a "switch" forms a retraction control system.

Another aspect of the present invention comprises an improved needle-syringe assembly which facilitates fabrication, and reduces the cost, of the assembly.

Still another aspect of the present invention comprises an improved needle-syringe assembly which facilitates the operation of the assembly, particularly when it is desired to retract the needle prior to disposing of the needle-syringe assembly.

Another aspect of the present invention comprises an improved needle-syringe assembly which improves the acceptability of the assembly by providing an external appearance which is virtually the same as that of conventional hypodermic needle assemblies which do not provide for needle retraction.

Yet another aspect of the invention comprises a needle-syringe assembly which provides for conventional operation for normal use, while needle retraction, once voluntarily activated, is automatic and complete.

Still another aspect of the invention comprises a needle-syringe assembly wherein the retracted position of the needle avoids puncture of the barrel and accidental sticking of medical staff.

Other aspects and advantages of the invention will become apparent upon reading the following detailed description and upon reference to the accompanying drawings.

In accordance with one aspect of the present invention, a syringe assembly, operable in a normal mode and convertible to a retraction mode, comprises a safety syringe assembly which includes an elongated, generally cylindrical barrel having a hollow interior forming a hollow nozzle located at a distal end of said barrel and opening into the interior of said barrel, a plunger slidably mounted in said barrel and having a longitudinal cavity, a needle holder slidably mounted in said longitudinal cavity of said plunger for movement between an advanced position in which a needle on the distal end of said needle holder projects from a distal end of said nozzle and a retracted position in which said needle is retracted within said barrel, elastic biasing means mounted inside said barrel and coupled to said needle holder for urging said needle holder toward its retracted position, and a latch releasably engageable with said needle holder and movable between a closed position in which said needle holder is latched to hold said needle holder in its advanced position against the urging of said biasing means, and an open position in which said needle holder is unlatched to allow said biasing means to move said needle holder to its retracted position.

In accordance with another aspect of the invention there is further provided an retractable needle, over-the-needle catheter and means for releasably securing the catheter to the above-mentioned safety syringe assembly, as well as modification of the present invention for a prefilled syringe.

Other improvements will be apparent after reading the appended description and claims which constitute their self supporting disclosure.

BRIEF DESCRIPTION OF THE DRAWINGS

In the drawings:

FIG. 4 is an elevation, partially in section, of a barrel portion of the syringe of FIGS. 1 and 2;

FIG. 5 is a sectional view rotated 90° from the view of FIG. 4;

FIGS. 15 and 16 are elevations rotated respectively by 90° from each other, of a plunger element of the syringe of the invention;

FIGS. 16a and 16b show an alternate embodiment of the plunger;

FIGS. 23 and 24 are a side elevation and plan view respectively of a latch or switch element in accordance with one embodiment of the invention;

FIG. 25 is a sectional view of the latch or switch element of FIGS. 23 and 24 assembled with a barrel;

FIG. 26 is a partial side elevation of a barrel showing the latch or switch element of FIGS. 23 and 24 assembled therewith;

FIGS. 31, 31a, 31b and 31c are elevation side and top views of an embodiment of a latch or switch similar to the embodiment of FIGS. 29 and 30;

FIGS. 42-47 illustrate a sequence of assembly of the syringe assembly of the invention;

FIGS. 50-54 illustrate a sequence of operation utilizing the syringe of the invention to place an over-the-needle catheter with respect to a vein of a patient;

FIG. 60 is a side elevation of another embodiment of a needle holder used in connection with the spring retainer of FIGS. 55-59;

FIG. 61 is an isometric view of the needle holder of FIG. 60;

FIGS. 73-77 show another embodiment of a plunger for a pre-filled syringe.

DETAILED DESCRIPTION OF THE ILLUSTRATED EMBODIMENT

Figure 1:
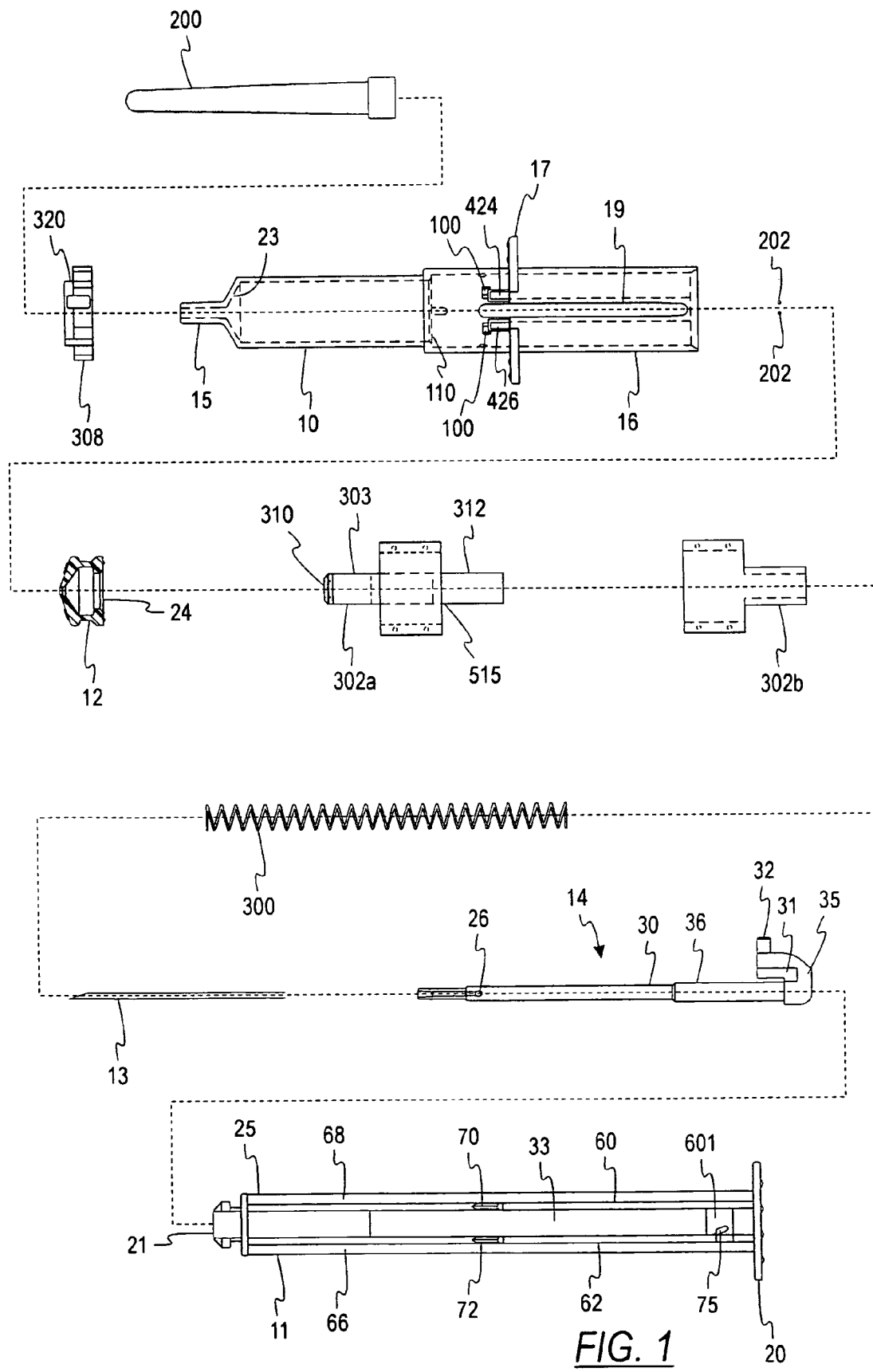
FIG. 1 is an exploded view of a safety syringe in accordance with the invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Several different embodiments of the invention, each with its own unique features and alternate embodiments, are described. Permutations and combinations of these features will, however, lead to further embodiments.

Figure 2:
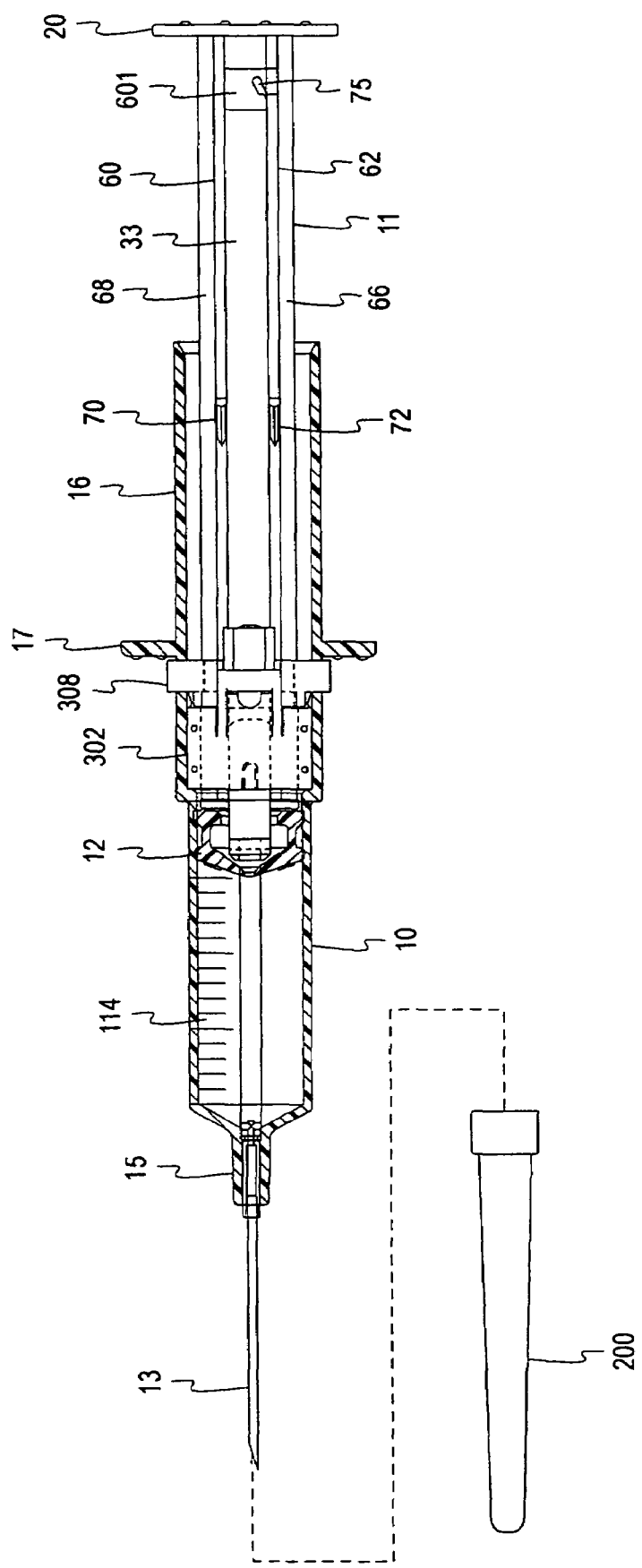
FIG. 2 is an assembled view of the syringe of FIG. 1, partially in section.

Turning now to the drawings, FIGS. 1 and 2 illustrate a needle-syringe assembly, including a barrel 10, a plunger 11, a hollow resilient (rubber) plunger cap 12, a hypodermic needle 13, and a needle holder 14. The barrel 10 is a hollow cylinder which terminates in a hollow tapered nozzle 15 at the distal end thereof, and has a slightly enlarged outer diameter portion 16 extending from about midway along its axial length to its proximal end. The interior of the nozzle 15 communicates with the hollow interior of the tubular body portion of the barrel 10. The barrel has outwardly extending flanges 17 on the proximal segment 16 of the barrel 10 which facilitate gripping of the barrel with the user's fingers when it is desired to move the plunger 11 relative to the barrel 10 linearly for normal use. The flange may be annular or oblong. A retracting means, such as an elastic or resilient biasing means, here illustrated as a compression spring 300 is mounted inside the barrel 10 and operatively contacts the needle holder 14 for urging the needle holder toward its retracted position, that is a position in which the needle 13 is retracted completely within the barrel 10 (see e.g., FIGS. 46-47).

In the embodiment illustrated in FIGS. 1 and 2, the elastic biasing means takes the form of an elongate compression spring 300 of relatively small diameter which fits about the outer circumference of the needle holder 14. This spring 300 is of such a diameter that it also inter-fits within an elongated channel or cavity 33 of the plunger 11. However, the elastic biasing means or spring may take a number of other forms without departing from the invention.

Figure 6:
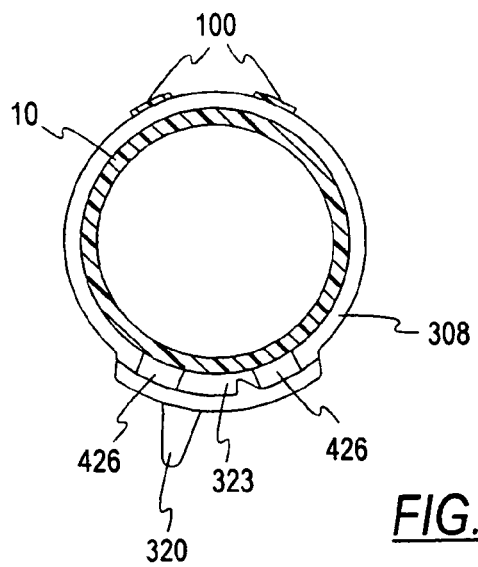
FIG. 6 is a sectional view illustrating assembly of a switch or latch element with the barrel of FIGS. 4 and 5.
Figure 7:
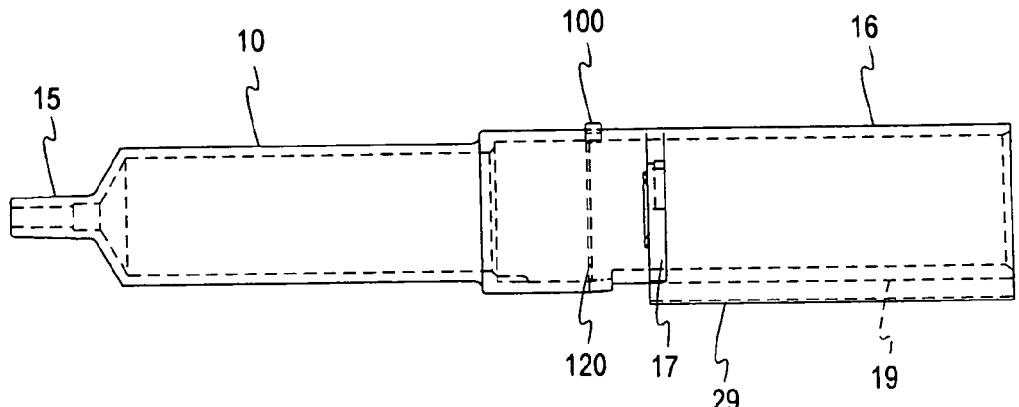
FIGS. 7 and 8 are an elevation similar to FIG. 5 and an isometric view showing an alternate embodiment of a barrel.
Figure 8:
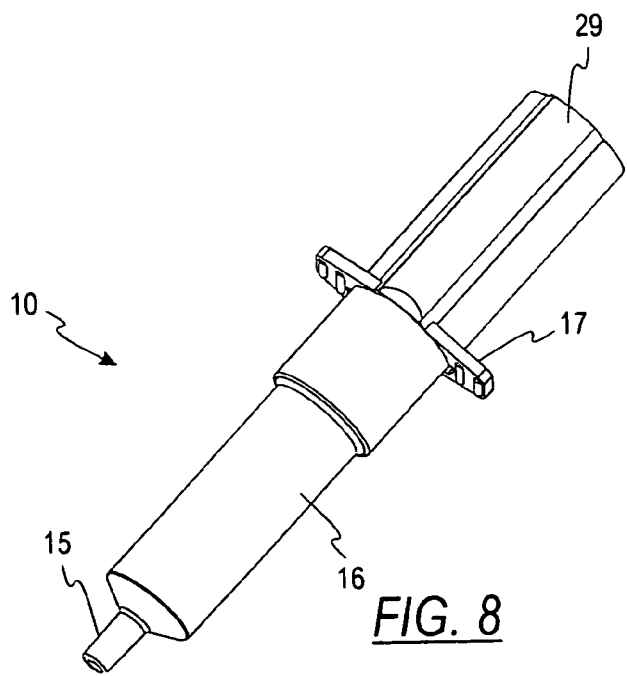
Figure 10:
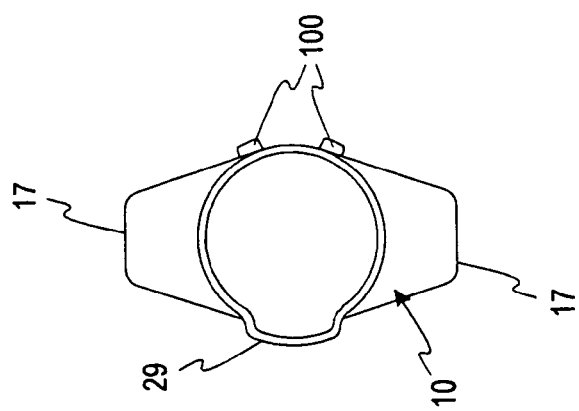
FIG. 10 is a section through the view of FIG. 9, similar to the section shown in FIG. 7.
Figure 9:
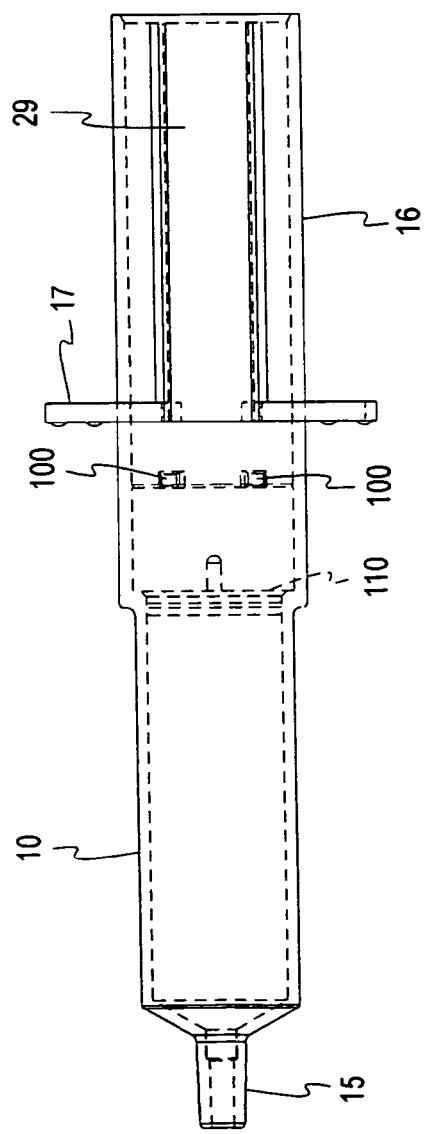
FIG. 9 is an elevation similar to FIG. 4 showing an alternate embodiment of a barrel.
Figure 11:
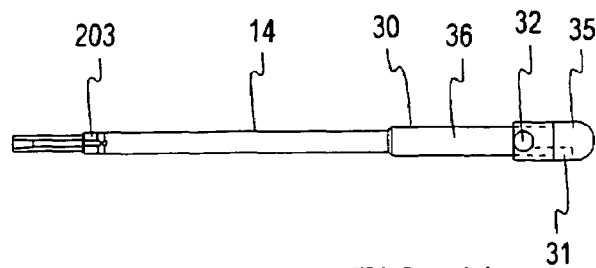
FIGS. 11 and 12 are respective elevations of a needle holder rotated respectively 90° from each other.

On one side of the barrel 10 and distal to the flanges 17, there are two square molded raised detents 100 intended to lock a cylindrical switch 308 (described later) between these detents and the flanges. During installation, recesses 426 on the switch 308 (see FIG. 6) clear the detents and the switch abuts the flange 17. A 180-degree rotation of the switch causes it to lock against the square detents. However, engagement of the needle holder arm 32 with the switch 308 prevents its rotation beyond 12-15 degrees. Once assembled, the switch is inseparable from the syringe, a safety requirement for all medical devices. As mentioned above, the proximal segment 16 of the barrel 10 beyond the flanges 17 has a somewhat larger diameter. The differential of internal diameters creates a structural shelf 110 that supports a cylindrical spring retainer 302 which can be a single piece or in two parts 302a, 302b. An elevated ring is molded within the barrel cavity to prevent proximal axial displacement of the spring retainer.

On the surface of the proximal segment 16 of barrel (see also FIGS. 4-8), opposite to the square detents 100 there is an open or closed channel or track 19 for locking the needle holder arm 32 (e.g., by switch 308) at its distal end and a serving as retracting track or guide once the needle holder 14 is released. The proximal segment 16 of the barrel 10 may be about one and one half inch in length for storing the needle holder with attached hypodermic needle in fully retracted, locked and secured in straight position within the plunger channel, in the center of the syringe. The distal part of the proximal chamber 16 also contains the spring retainer and spring. The needle holder, in turn is releasably locked to the barrel via the switch 308. The needle protector cap 200 provides an air and water tight seal at the nozzle before use, while after use it will prevent leakage of any contaminant, and the entire syringe can be disposed of in biological waste. The cap 200 and nozzle may have interlocking luer tapers or, even threads to secure the caps, for example, for a pre-filled syringe.

In an alternate barrel embodiment (see FIGS. 7-10), the slot that permits the retraction of the needle holder arm proximally is covered by an increased diameter wall segment 29, which merges with the barrel circumference at its margins. The distal end of the wall segment 29 may be open to permit engagement of the needle holder arm 32 by the latch/switch 308, or closed, for use with an internal latch/switch described later. Such a "covered" design may be advantageous because it can be molded by straight pull tooling. This reduces the cost of tool by avoiding complex side action slides (i.e., to mold the track 19), and increasing the density of the parts in the mold. The barrel without the exposed track 19 has a more esthetic appearance and is also more hygienic. Further, the distal end of the wall 29 if open, is covered by the switch 308 or 408, which provides a uniform surface to the syringe.

This alternate design (FIGS. 7-10) is otherwise similar to the above-described embodiment (FIGS. 4-8) of the barrel.

The outer surface of the barrel 10 may contain graduations 114 (FIG. 2) indicating the volume level of fluid in the barrel. These graduations take into account the volume of the internal components such as the needle holder 14.

The proximal end of the plunger 11 forms a knob 20 that can be grasped by a user to effect linear movement of the plunger 11 relative to the barrel 10. The periphery of the knob 20 can be serrated or engraved to prevent slipping of the knob during the use of the plunger. The distal end of the plunger 11 forms a head 21 to mount the hollow rubber plunger cap 12 thereto. The outside diameter of the resilient cap 12 is reduced in the central portion so that the cap engages the inside wall of the barrel 10 only at the pliable margins of the ends of the cap. The diameter of the engaging end portions of the cap 12 is slightly larger than the inside diameter of the barrel 10 so that the cap presses firmly against the inside wall of the barrel to form an air-tight and liquid-tight seal at the cap/barrel interface. The inner margins of the cap 12 make a similar tight contact with the outer surface of the needle holder 14. The distal end 22 of the cap 12 is conical to conform to the conical distal end 23 of the inside surface of the barrel 10 when the plunger 11 is fully advanced within the barrel. This reduces the dead space and assures complete emptying of medicine into the patient. The outer wall of the cap 12 may be thickened somewhat to prevent its collapse during the in barrel assembly process (described later).

The head 21 of the plunger 11 is configured to fit within the hollow plunger cap 12. With the cap 12 locked onto the head 21 of the plunger, the flat proximal end 24 of the cap abuts the flat surface of a circular disc 25 at the base of the plunger head 21. The disc 25 transmits advancing force to the rubber cap 12. Due to the air-tight and liquid-tight seal between the plunger cap 12 and the barrel 10, as well as the needle holder 14, advancing movement of the plunger 11 inside the barrel 10 creates pressure in the interior of the barrel between the plunger cap and the distal end of the barrel. Similarly, retracting movement of the plunger 11 creates a vacuum in that portion of the barrel interior.

The distal end of the plunger head 21 is flat or frustoconical while the mating inner surface of the cap 12 is conical with space for a lose fit. This mismatch is intentional and functional. The significance is described later in disclosure.

Referring to FIGS. 11-14, the hypodermic needle 13 is mounted on the distal end of the elongated needle holder 14, which is detachably interlocked to the barrel 10 (in channel or track 19). Prior to use of the needle-syringe assembly, the needle 13 is covered by a protective cap 200 mounted on the nozzle 15 which prevents needle pricks, preserves sterility prior to use, and preserves the barrel pneumatic volume. In addition, the nozzle may have an external or male luer taper that mates with an internal or female luer taper of the protective cap. When engaged they form strong locking contact to prevent accidental separation of parts during transport or handling. The luer lock also creates an air and water tight seal that prevents air from the barrel from escaping and maintaining a positive air pressure within the syringe barrel. Positive air pressure in the syringe barrel prevents intentional as well as accidental advance of the plunger in barrel. This assures that the retraction mechanism will not be activated until the user removes the protective cap from nozzle. The medicine aspirated in the syringe before expelling the air also assures that the plunger does not advance to the point of causing retraction. If these instructions are followed there is no chance of premature/accidental retraction of the hypodermic needle and disablement of the syringe.

Figure 3:
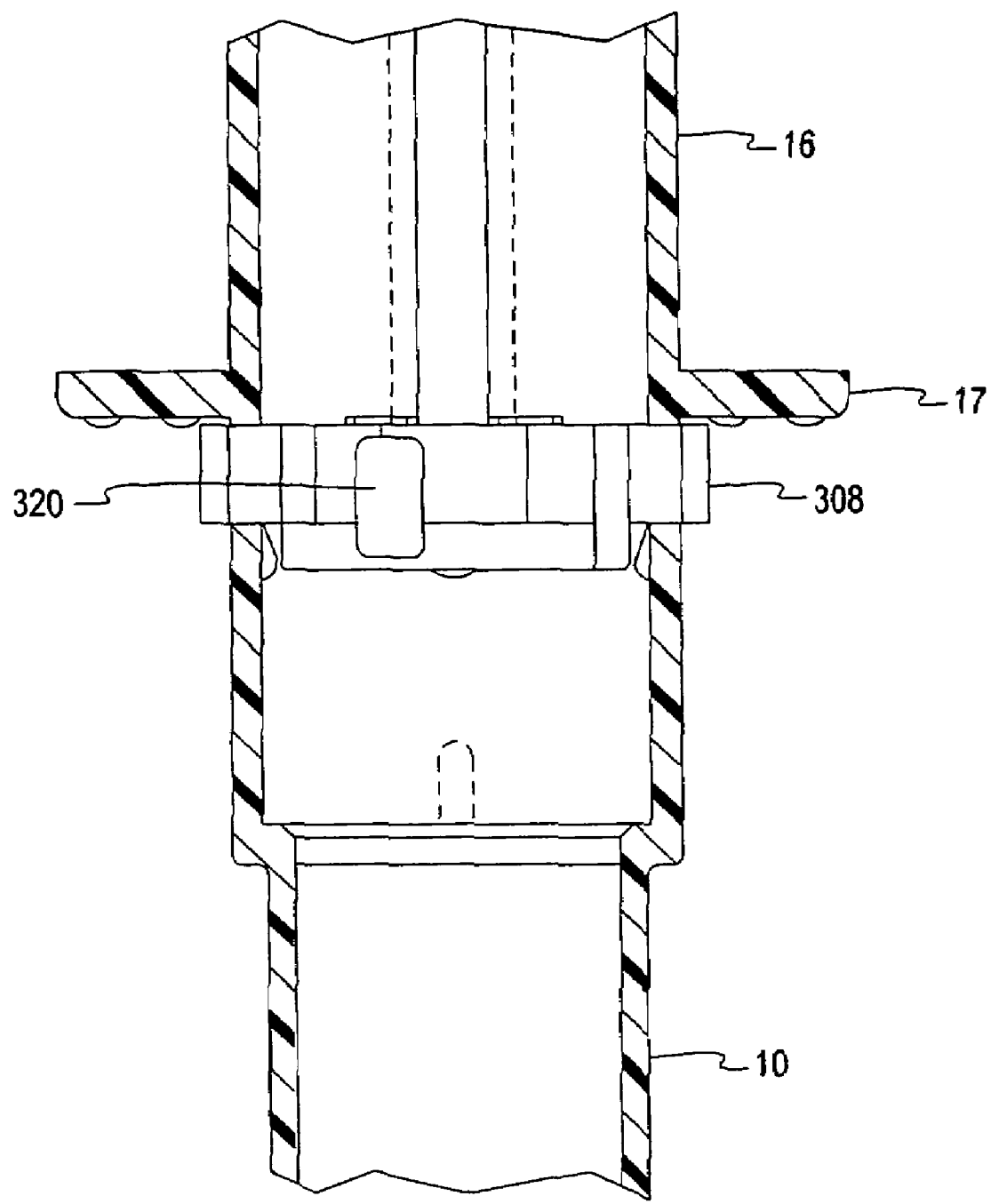
FIG. 3 is a partial elevation of the syringe of FIGS. 1 and 2.
Figure 14:
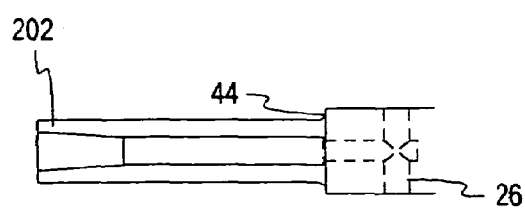

Both the needle 13 and the distal portion of the needle holder 14 are hollow, and the interior of the hollow needle 13 communicates with the interior of the hollow distal portion of the needle holder 14. The needle holder 14 further communicates with the interior of the barrel 10 through an aperture 26 which extends through the side wall of a hollow portion of the needle holder 14 at a distal end thereof (FIG. 14). Prior to and during use of the needle-syringe assembly for injection of medicine (hereafter referred to as "normal use"), the aperture 26 is positioned at the base of the barrel nozzle 15, sometimes within a small cylindrical cavity (not shown). The side aperture 26 permits medicine to enter or exit from the barrel 10 via the needle holder 14 and the needle 13. The proximal end of needle 13 is not directly open to air and therefore the needle does not have an "open" end on retraction, as in some prior art arrangements. Instead it is glued within the cavity of the needle holder, and fluid transport occurs through the side hole 26 at a boundary zone. A small rubber O-ring 202 is located against a distal shoulder 27 of the barrel interior (see FIGS. 3-4) to promote sealing engagement with a distal end 41 of the needle holder 14 when the distal end 41 is stepped down as shown in FIG. 14 to provide a shoulder. A set of luer tapers may be used as an alternate form of sealing.

During normal use of the needle-syringe assembly, the needle holder 14 is directly or indirectly locked to the barrel 10 (in track 19), and the plunger 11 with its cap 12 is free to slide longitudinally back and forth along the needle holder within the barrel. In one embodiment, (see FIGS. 11-13) the needle holder 14 includes a generally L-shaped rod having a longitudinal body portion 30 extending to the aperture 26 and hollow from the aperture 26 to its distal end, and a lateral arm 32, supported on an enlarged, shaped end part 35 of the needle holder 14, for extending radially across the barrel 10 and through the track 19, at a proximal end of the body 30.

The lateral arm 32 of the needle holder 14 may also include an enlarged diameter circumferential shoulder surface 35 for engagement with outermost surfaces of plunger ribs 60, 62 (described below) which form the channel 33, so as to position the needle holder 14 at the proper depth with respect to the channel 33.

A proximal part 36 of the straight portion 30 of the needle holder has a larger diameter for supporting the compressed length of the spring 300 within a spring retainer 302 (described below). The lateral arm 32 is also heavier to resist the vertical force of the spring 300 as well as to dampen the peak velocity of the retraction when released.

Figure 12:
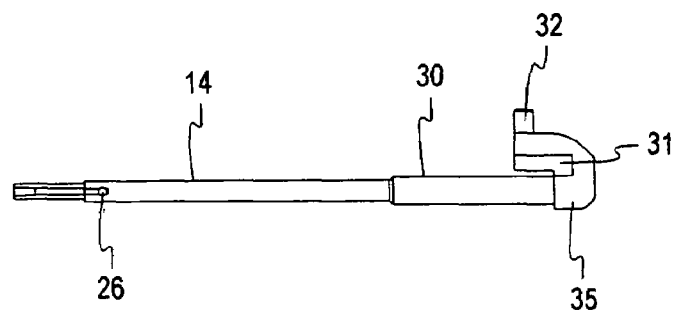
Figure 13:
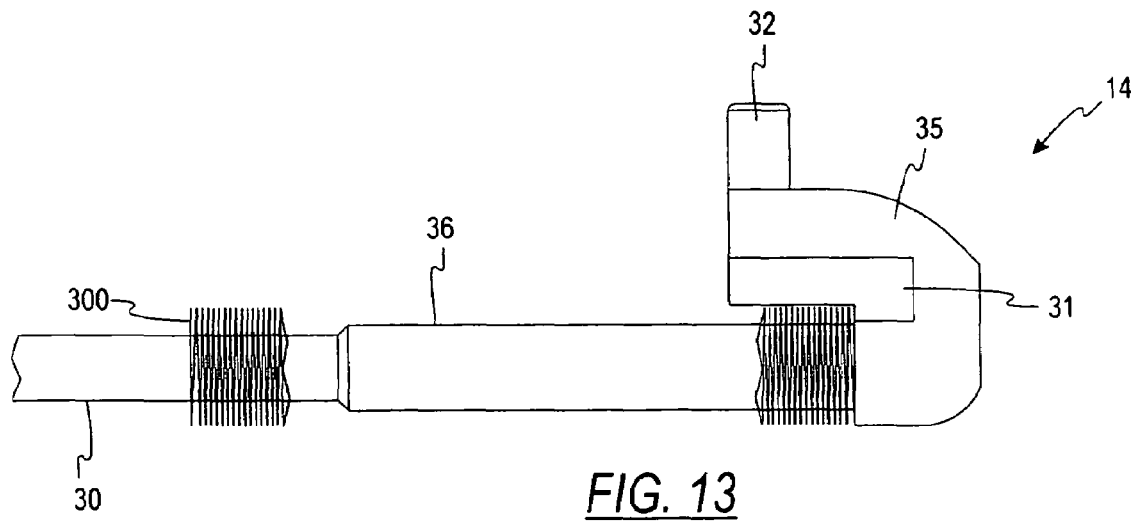
FIGS. 13 and 14 are enlarged views of portions of the needle holder of FIGS. 11 and 12.

The end portion 35 of the needle holder 14 has a rectangular recess 31 on the side as shown in FIGS. 12 and 13. This recess 31 locks with a detent 75 within the plunger channel 33 (see FIGS. 14 and 17) when the needle holder is retracted. This interlocks the syringe assembly in a safe position. In addition, the expansion of the spring also maintains the needle holder at this location.

Referring also to FIGS. 15-19, to permit relative sliding movement between the plunger 11 and the needle holder 14 in the longitudinal direction, the needle holder is mounted in a longitudinal cavity or channel 33 formed as an integral part of the plunger 11. Multiple pairs of resilient retaining elements or detents (not shown) project toward each other from the opposed walls of the channel 33 to retain the needle holder 14 within the channel.

Figure 19:
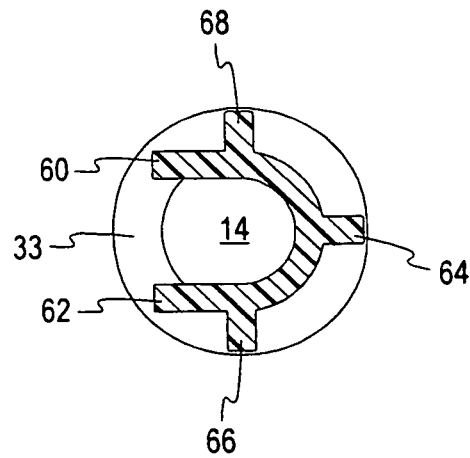
Figure 20:
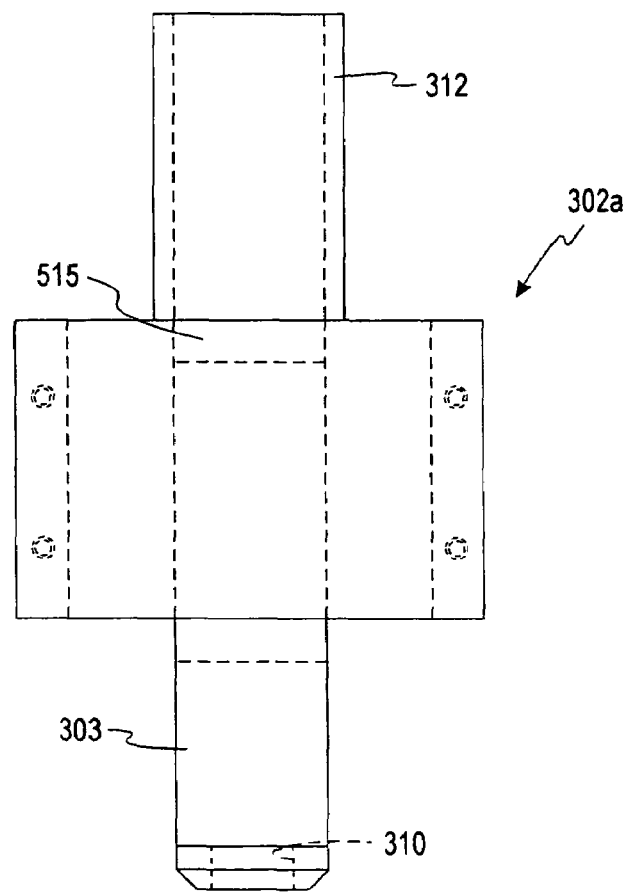
FIGS. 20, 21 and 22 are respectively a front elevation, an end or top view and a side elevation of a spring retainer element of the syringe assembly of the invention.
Figure 21:
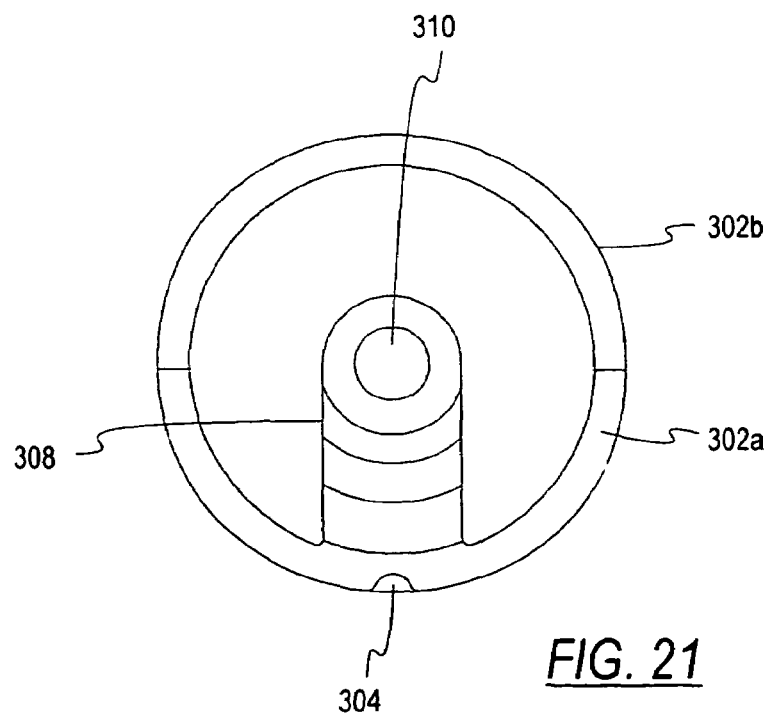
Figure 22:
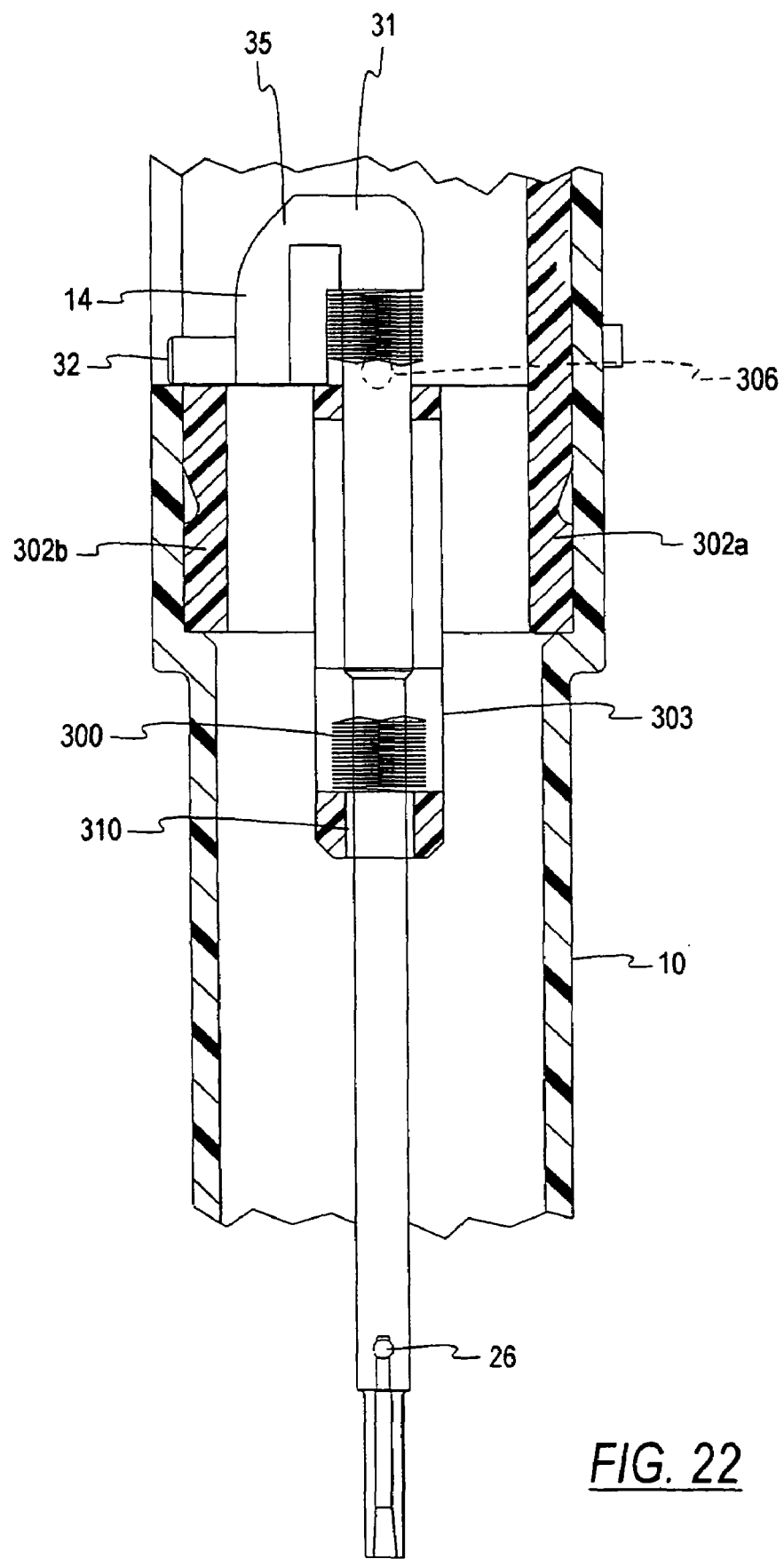
Figure 27:
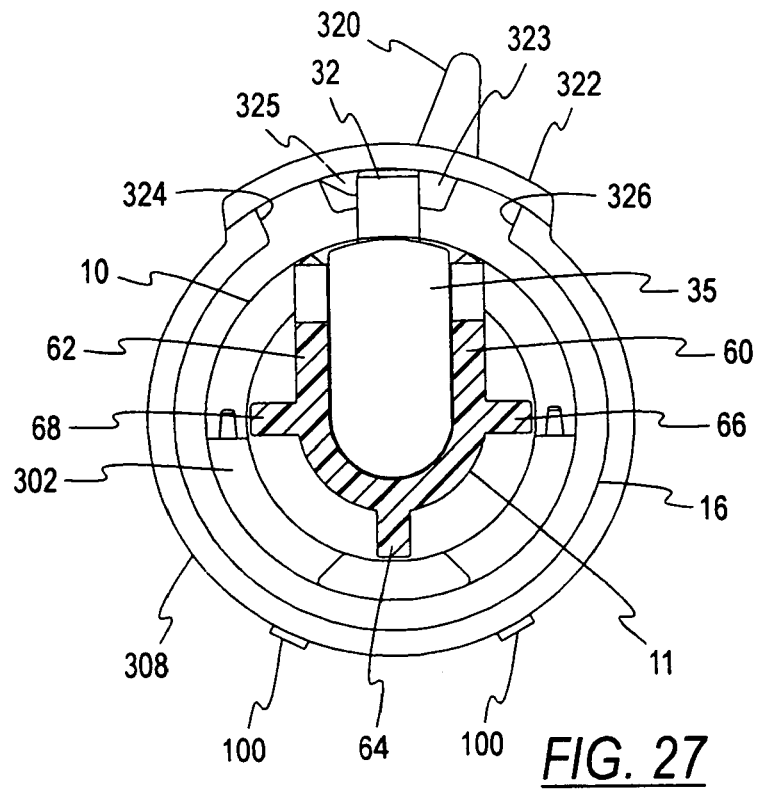
FIGS. 27 and 28 are respective sectional views, similar to FIG. 25 showing the assembled syringe assembly with the latch or switch element respectively in a locked and unlocked positions.
Figure 28:
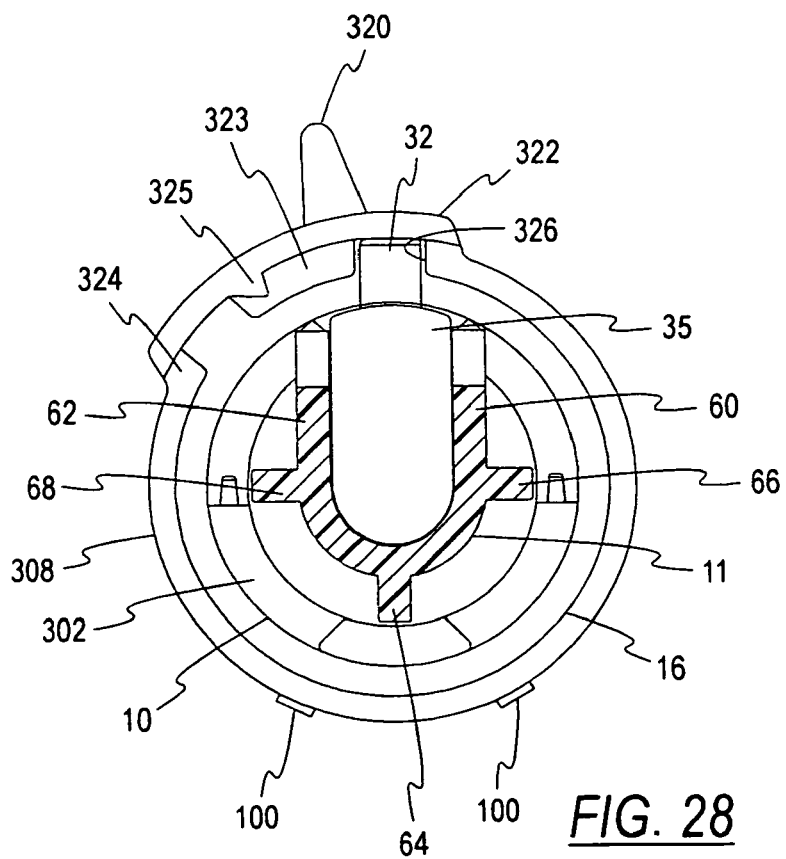
Figure 31:
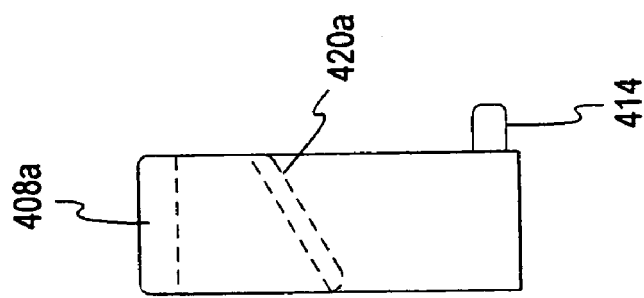
Figure 30:
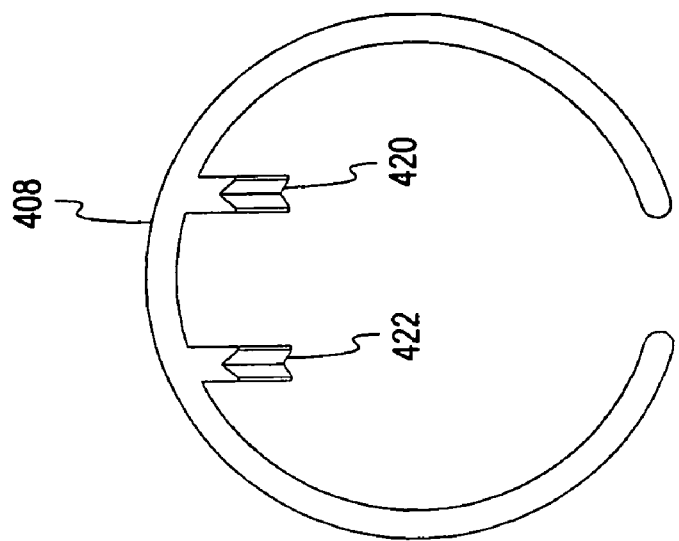
FIGS. 29 and 30 are respective elevation and plan views of a latch or switch element in accordance with another embodiment of the invention.
Figure 29:
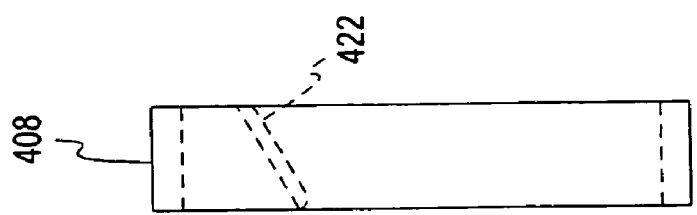
Figure 32:
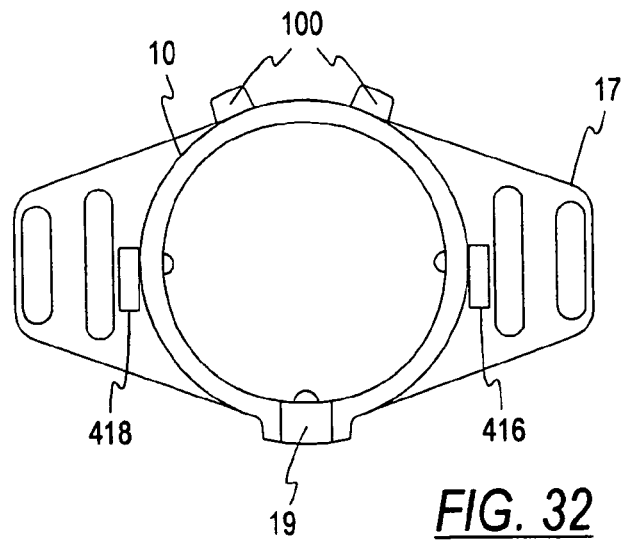
FIG. 32 is a partial sectional view showing assembly of the switch element of FIGS. 29-31 with a barrel.
Figure 33:
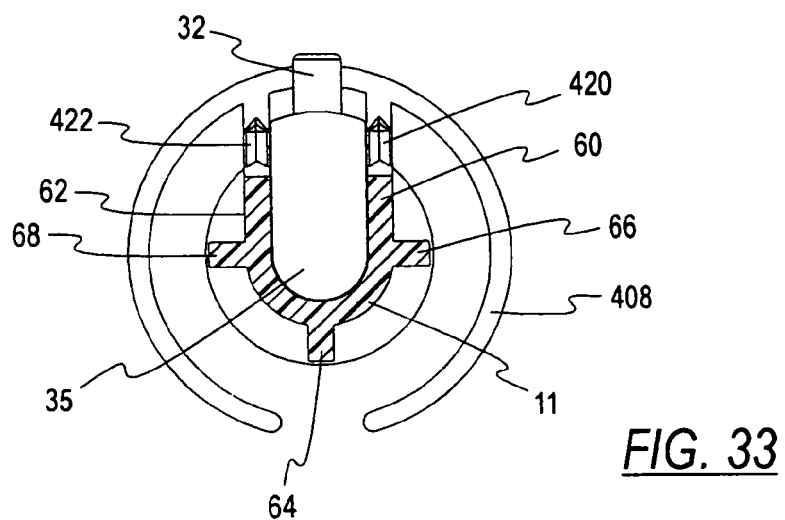
FIGS. 33 and 34 are partial sectional views illustrating locking and unlocking positions of the switch or latch of FIGS. 29-31 with respect to activating or unlocking elements on a plunger of the type shown in FIGS. 15 and 16.
Figure 34:
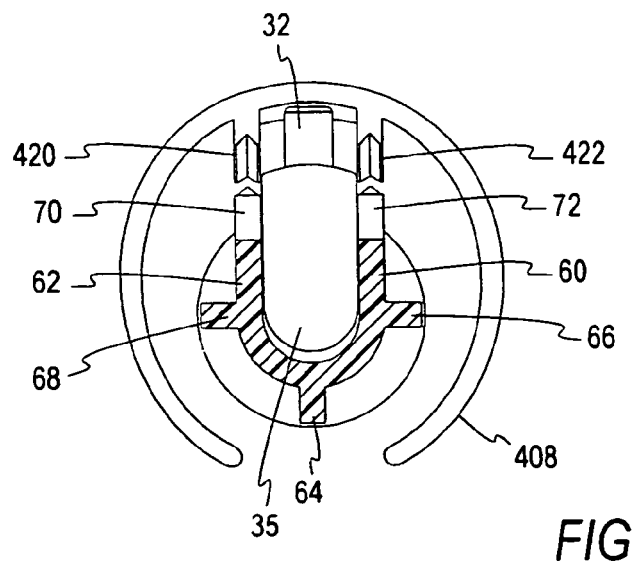
Figure 37:
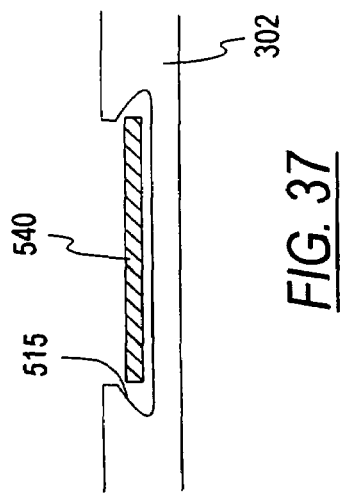
FIG. 37 is a partial sectional view showing a portion of the latch element of FIGS. 35 and 36 assembled with a spring retainer element of the type shown in FIG. 20.
Figure 36:
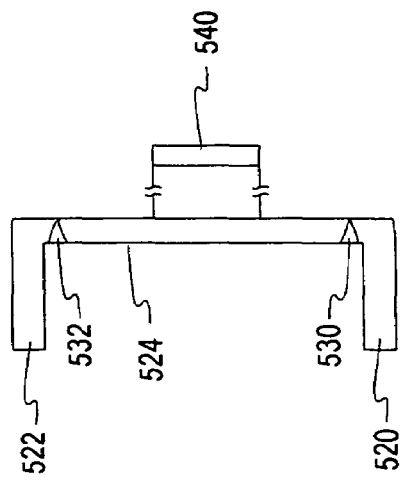
FIGS. 35 and 36 are respective side and top views showing a switch or latch element in accordance with yet another embodiment.
Figure 35:
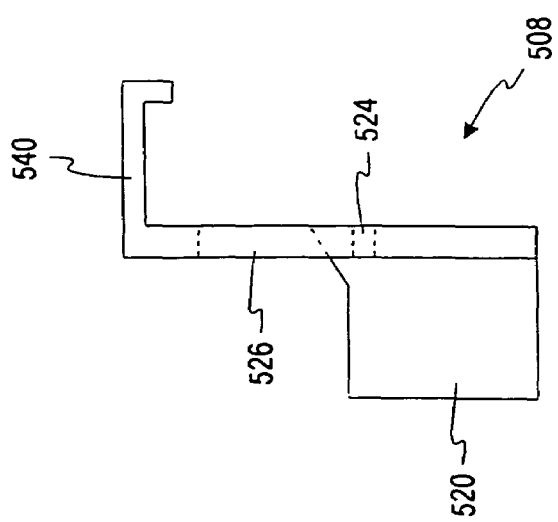
Figure 38:
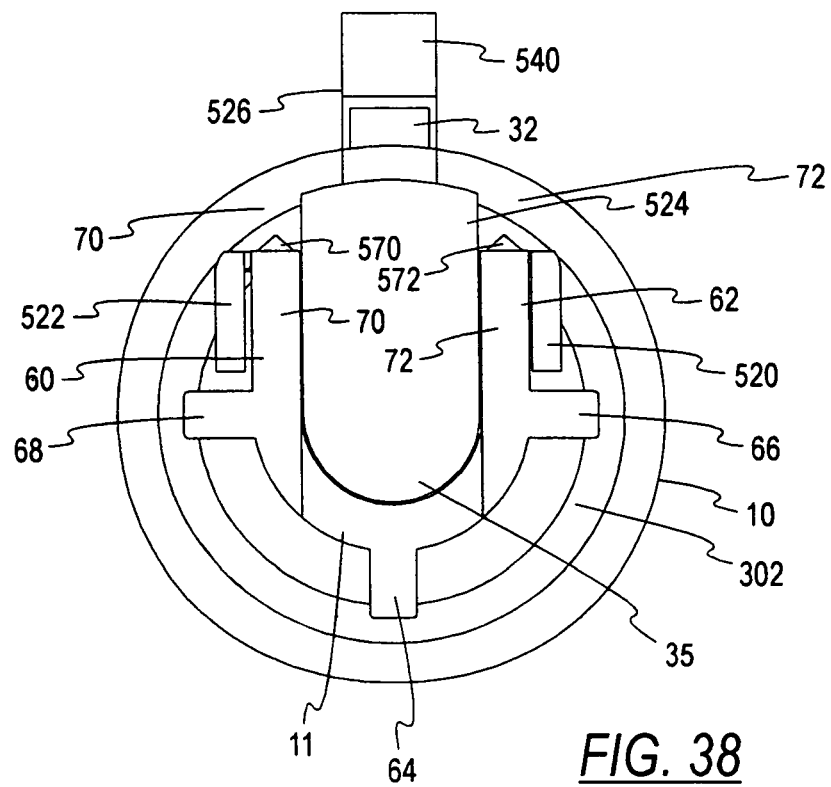
FIGS. 38 and 39 are respective sectional views showing the latch or switch element of FIGS. 35 and 36 assembled with a syringe assembly and respectively in latched and unlatched positions.
Figure 39:
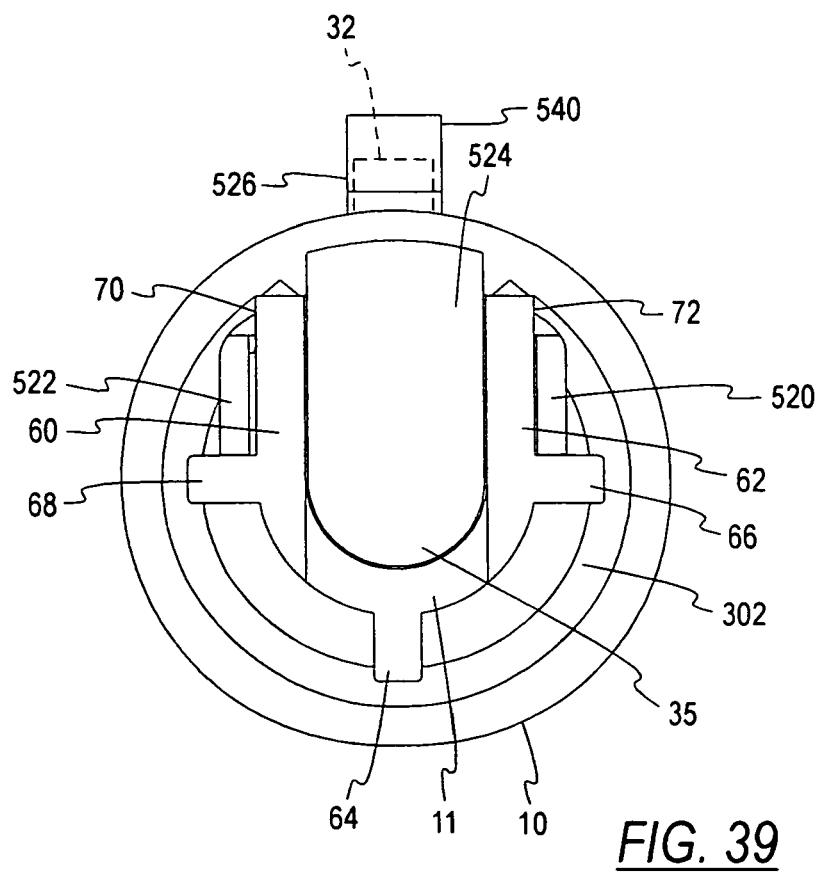

Referring also to FIG. 19, the plunger 11 will be seen to have a plurality of ribs. A first pair of these ribs 60, 62 define the longitudinal channel 33 for receiving the needle holder 14 as described above. A single rib 64 projects diametrically oppositely of these ribs 60 and 62, it forces the needle holder arm 32 through the track 19 and assures stable engagement and retraction. A further pair of diametrically oppositely extending ribs 66 and 68 are formed in a plane at right angles to the ribs 60, 62 and 64. In the embodiment of FIGS. 16a-16b, in the proximal one and one half portion of the plunger, the three ribs 64a, 66a, 68a, collectively extend transversely across the interior of the barrel 10 so as to help maintain the circular configuration of the barrel, for example, to counteract any weakness caused by the track 19. This also helps to ensure the locking engagement of the lateral arm 32 with the track 19.

The plunger 11 is the sole moving part of the syringe in normal operation, and makes contact with the fluid chamber defined in the barrel via the rubber stopper 12. The linear movements of the plunger within the barrel determine the amount of the fluid taken in and injected into the patient. These movements and location of the plunger can therefore be mechanically indexed to the functional outcome of the syringe, retraction of the needle holder as well as disablement of the syringe. Two triangular projections 70 and 72 on the margins of flanges 60 and 62 are designed and located to interact with a switching mechanism or "instant switch" as explained later.

In the illustrated embodiment, the opposed walls or ribs 60, 62 of the channel 33 extend toward the inside wall of the barrel 10 (see FIG. 19), thereby constraining the lateral arm 32 of the needle holder against any angular or rotational displacement relative to the plunger 11. That is, the plunger 11 and the needle holder 14 can rotate if ever only in unison with each other, although they may move freely independently of each other in the longitudinal direction to permit needle restriction after normal use. At the proximal end of the channel 33, a locking detent 75 locks the end portion 35 of the needle holder and plunger together to prevent relative longitudinal movement after retraction of the needle holder 14 is complete.

In the illustrated embodiment, the proximal end of the needle holder 14 is directly or indirectly, locked to the barrel 10, via the lateral arm 32. This arm 32 extends radially beyond the plunger channel 33 and fits into the track 19 in the barrel 10. The arm 32 can be locked to the barrel 10 at the distal end of the track 19 and, when so locked, permits only reciprocal linear movement of the plunger 11, to create vacuum to withdraw medication and pressure to deliver medication to the patient via the hypodermic needle 13. When the needle holder recess 31 is locked in the plunger detent 75, following use, the entire assembly is interlocked and inoperative. During normal use, the needle holder holds the needle completely advanced or projecting from the nozzle 15 of the barrel 10.

When fully expanded, the compression spring 300 guarantees full retraction of the hypodermic needle 13 and needle holder 14 as well as subsequent maintenance of the needle holder 14 in the retracted state. The retraction force interlocks the needle holder detent 31 with the plunger detent 75 (FIG. 7) as well as plunger arm 32 with the barrel track 19. This renders the syringe components totally interlocked and inoperative.

The spring 300 is supported on a robust foundation provided by a spring retainer 302 shown in FIGS. 1 and 20-22. The spring retainer, which may be either unitary 302 or two parts (302a and 302b), is installed in the barrel at the shelf like projection 110 defined by the proximal segment 16 of the barrel 10. Mating detents 304, 306 provided on the contacting surfaces of barrel 10 and spring retainer 302 restricts rotary movements of spring retainer 302 inside the barrel 10. Proximally, an elevated ring 120 (see FIG. 5) molded within the barrel just above the margins of the spring retainer 302 securely locks it in place, once the spring retainer 302 has been axially advanced past the ring 120 during assembly. A distal axial extension 303 of the spring retainer 302 holds the spring 300 at the margins at one end thereof while permitting the needle holder 14 to pass through a central hole 310. The spring 300 is retained in compressed state by releasably locking the needle holder arm 32, via the switch (e.g., 308) to the barrel 10. The opening 310 of the spring retainer 302, the spring 300 and the needle holder 14 are concentric with the plunger channel 33 and with the axis of the barrel cavity.

Additional features of spring retainer 302 include a proximal projection 312 which extends along the inner surface of the barrel 10 and provides mechanical support. This minimizes the play with the barrel and holds the needle holder tightly locked within the barrel.

As mentioned above, a switch or latching means or mechanism 308 controls the position of the needle holder 14 relative to the barrel 10 for presenting the needle either fully advanced or fully retracted with respect to the barrel. In the embodiment shown in FIGS. 1, 2 and 6, the latching mechanism 308 takes one form. However, other equivalent forms may be used without departing from the invention, some of which are further described hereinbelow. In the embodiment shown in FIGS. 1 and 2, the latching means or switch comprises a needle holder locking element 308, having an aperture 310 which inter-fits about a free end portion of the radially projecting arm 32 of the needle holder 14 which projects outwardly of the track 19 in the barrel 10, as described above.

A number of regulatory bodies require or recommend that in the safety syringe devices, the switch is inseparable from the syringe. In general, these requirements or recommendations state that the functional attachments of a medical device which alters the functions of the device such as clamps, switches etc. should be inseparable from the device. These switches or other attachments must move and work, but they should not be removable. In the present invention, the ring switch as well as the barrel where the switch is installed were designed to comply with these medical device standards and regulations.

Referring also to FIGS. 23-28, the switch 308 comprises a closed cylindrical ring with an internal diameter which inter-fits about the outer diameter of the proximal portion 16 of the barrel. A small lock-release lever 320 is molded on the outer surface of an outwardly projecting portion 322 which has an inward projection 323 to engage and lock the needle holder arm 32 that projects out from the track 19. Needle holder arm 32 has only linear mobility in the track 19 along the axis of the syringe. The switch holds the needle holder arm 32 in position with the spring in a compressed state. Further, the switch 308 can not be displaced or rotated because it is engaged with needle holder arm 32 exiting from the slot on the barrel. The switch lever 320 can rotate to disengage the needle holder by the flip of the thumb of the same hand that is also holding the syringe. The switch completely encircles the barrel between the flanges 17 and the switch retainers-square detents 100 so as to lock the linear movement of the switch on barrel. When engaged It can only rotate one way 15-20 degrees to release the needle holder. It has no other mobility and can't go anywhere. The switch 308 is inseparable from the syringe until the syringe itself is disabled.

The installation of the switch is as follows. Two slots or recesses 324 and 326 axially slide over the square detents 100 molded on barrel wall for assembly. The switch is inserted on the barrel from the nozzle side (distal end) so that the square switch detents 100 on the barrel are negotiated through the recesses 324 and 326 of the ring switch. Once the recesses are negotiated, the switch makes a contact with the flange 17. At this time the switch 308 is rotated 180 degrees to engage and lock with the arm 32 of the needle holder and therefore with the barrel (FIG. 24). A small detent 325 of the switch 308 engages the lateral arm 32 and limits switch rotation to one direction. The square detents 100 are now locked against switch 308, locking the switch 308 in place between these detents 100 and flange 17, since the recesses 324, 326 are now moved to a diametrically opposite location (see FIG. 25). Now, only the user can voluntarily rotate the switch lever 320, 15-20 degrees of rotation one way to retract and disable the syringe by just a flip of thumb of the same hand that is also holding the syringe. This causes retraction of needle holder, by aligning one of the slots 324, 326 (326 in the illustrated embodiments in FIG. 28) with the lateral arm 32 and disables the syringe.

The ring switch 308 is, therefore, actuated only upon a conscious decision and voluntary effort on the part of the user to engage and rotate lever 320. This avoids accidents, and reduces chance factors in retraction and disablement of the syringe.

Two other embodiments (FIGS. 29-34 and 35-38) of the invention are provided with an improved "instant" switch. Operation of this switch requires that contents of barrel are completely injected and that a slight additional push is given on the plunger to release needle holder and initiate retraction, and thereupon to interlock and disable the syringe. This requires some action of operator, but can be called "involuntary," in that it does not require the operator to engage or manipulate any additional elements but only to press the plunger a bit further after completing the injection and withdrawing the needle from the patient.

Figure 17:
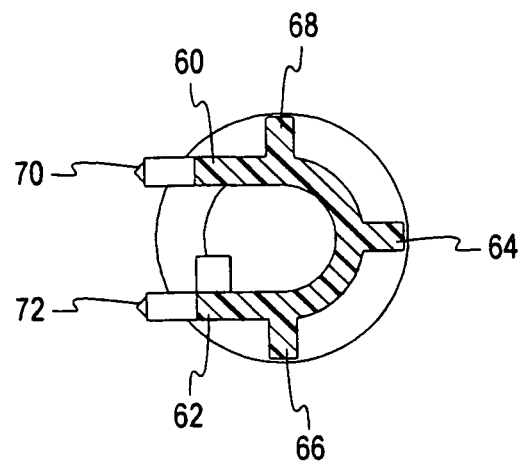
FIGS. 17 and 19 are two sections through the plunger of FIGS. 15 and 16.
Figure 18:
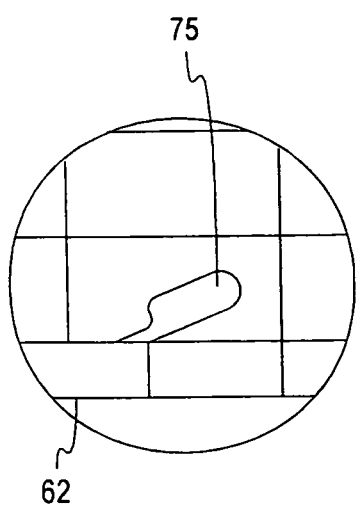
FIG. 18 is an enlarged view of a portion of the plunger shown in FIG. 15.

During injection, the plunger 11 is the sole moving part of the syringe and makes contact with the fluid chamber 27 via the rubber stopper 12. The linear movements of the plunger within the barrel determine the amount of the fluid taken in and injected into the patient. These movements and location of the plunger can therefore be mechanically indexed to the retraction of the needle holder as well as disablement of the syringe. The two projections 70 and 72 on the margins of flanges 60 and 62 as shown in FIGS. 15-17 are precisely designed and located. They interact with the switching mechanism of the "instant" switch as explained below.

The principle of the instant switch is based on the linear indexing of the plunger advance within the barrel that is proportioned with the force applied to the plunger head by the operator's thumb. At a normal fluid injection force of a fraction of PSI the distal circular plate 25 pushes the rubber piston to the end of the barrel and injects the contained medicine via needle and one limit of the plunger advance is reached at this force. The barrel is completely emptied but it does nothing to the switching mechanism. The design of the present invention includes a flat surface 21 of the plunger end that is placed within the conical cavity 24 of the rubber piston 12 creating an empty or mismatched space. It also selects a situation specific compressible resilient rubber piston. These elements together provide an additional range for the plunger to advance within the barrel at a higher compression force-PSI. This additional travel of the plunger within the barrel creates a contact between the plunger ramps 70, 72 with corresponding parts of the switch resulting in the release of the instant switch and release of the needle holder and retraction of the hypodermic needle inside the barrel. This mechanism can be further fine tuned by adjusting the internal diameter of the distal end of the barrel, which will increase the force required to advance the plunger, or incorporating an internal ring or another stop or detent surface (not shown) in the barrel that will alert the operator of the peak force and imminent retraction moment. In addition placing a spring between the plunger plate and the cavity of the resilient cap will also predictably alter the linear length of plunger advance and improve the efficacy of the switch.

Referring to FIGS. 29-34, the "instant" switch 408 comprises a cylindrical ring, having an open circumferential portion, that partially encircles the barrel 10 just distal to the flanges 17 and proximal to the square detents 100 and holds the arm 32 of the needle holder in place in the distal end of the track 19, anchored to the barrel 10 under its distal margin. This location axially locks the switch to the barrel 10 and prevents its linear movement along the axis of the barrel 10. The only movement that is possible is the radial displacement of the switch away from the barrel 10, solely because the switch has an opening 410 in its circumference. However the resilient material or memory of the switch 408 normally keeps it in contact with the barrel. In a modified form (FIGS. 31a-c), the switch 408a may be semi-cylindrical and have inwardly projecting detents 412 and 414 that engage slots 416, 418 on the flanges 17 of the barrel 10. This prevents rotation and helps to retain the switch on the barrel.

The switch 408 (408a) has two ramp-like projections 420 (420a) and 422 (422a) which extend from its inner surface and enter the barrel 10 through two windows 424 and 426 in barrel outer wall. The windows also permits projections 420, 422 (420a, 422a) of the instant switch 408 (408a) to make a contact with the ramps 70-72, located on the plunger flanges 60 62. The windows are ultimately and totally covered by the switches installed on the barrel at this location as is the open channel underneath. The projections 420, 422 (420a, 422a) have angled edges and juxtapose against the identical angular ramps 70 and 72 projecting from the plunger plates 60-62 when the plunger is fully advanced. The angles on the two sets of projections/ramps are identical but face in opposite in direction. During normal operation, these parts 420, 422 (420a, 422a) and 70,72 have no contact with each other. It is only when the medicine is fully injected in the patient and the plunger is further advanced, that the parts 420, 422 and 70, 72 start making contact. Further distal linear movement of the plunger results in a radial outward movement of the switch 408 (408a) that results in the release of the needle holder arm 32 that it was locking under its distal margin (see FIGS. 33 and 34).

Summarizing the above, movement of the switch 408 (408a) away from barrel 10 releases the needle holder 32 instantly and effects the retraction of the needle. The linear advance of the plunger in the barrel causes the linear movement of the plunger to be transformed into the radial movement of the switch 408 (408a) for releasing the needle holder (see FIG. 34). A normal advance of plunger 11 causes the plate 25 to push the rubber stopper 12 distally to make contact with the barrel cone 23 and the entire medicine is injected in the patient. An additional push on the plunger head 20 further advances the flat plunger end into the conical cavity of the rubber piston. The pressure squeezes the elastic rubber piston 12 and permits the further advance of plunger and consequently the ramps or plates 70, 72 contact the switch and actuate the "instant" switch 408 (408a) for retraction and release of needle holder as well as disablement of the syringe as described above.

In one example, with a 3 cc syringe constructed as described above and with an "instant" switch 408 a terminal 6.5 PSI force on the plunger head caused displacement of plunger head within the rubber stopper as well as some compression of rubber stopper to generate 0.040 inch distal displacement of the plunger ramps 70 and 72. This displacement in turn radially displaces the "instant" switch by 0.040 inch and releases the needle holder arms to retract the needle holder as well as lock it to barrel and disable the syringe. These results depend on the size and length of the syringe, elasticity and durometer of the rubber piston, durometer of the plastic polymers and amount of the force exerted on the plunger knob as well as environmental/temperature variations which affect rigidity of polymers.

Figure 40:
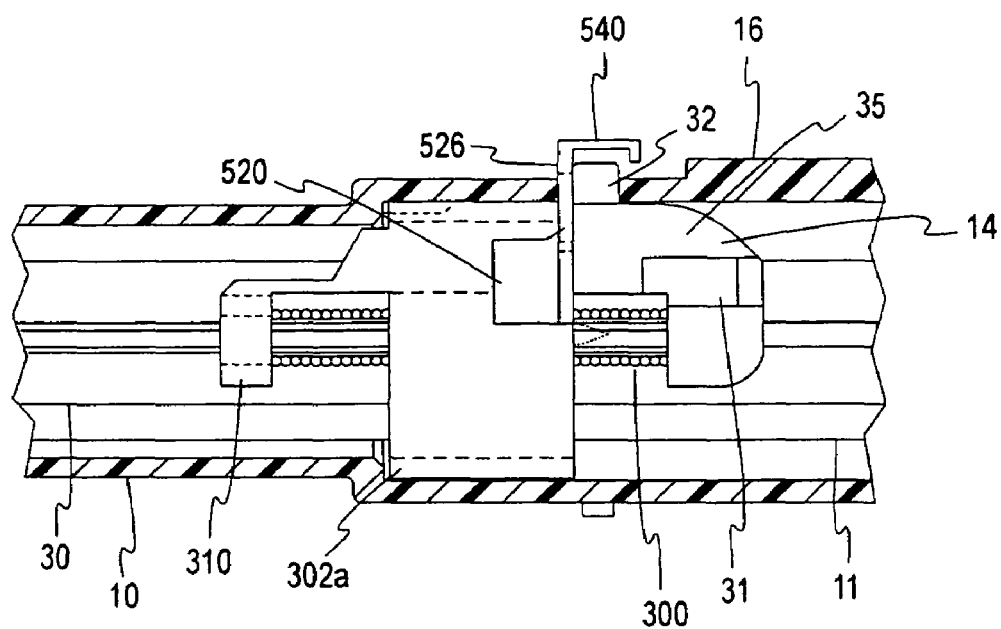
FIGS. 40 and 41 are partial side views, partially in section, illustrating further the operation of the latch element of FIGS. 35 and 36.
Figure 41:
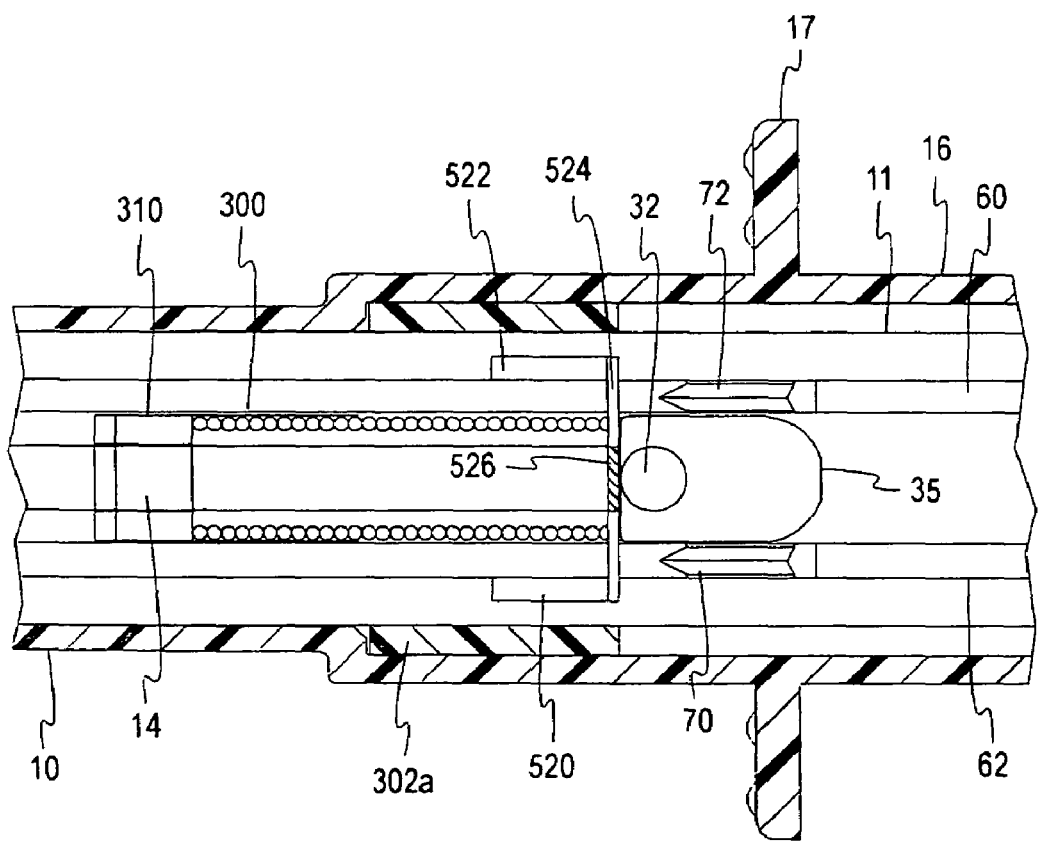

Referring to FIGS. 35-39, another embodiment of an "instant switch" 508 comprises two thin flat plates 520, 522 which are connected by a bridge 524. A flat projection 526 extends from the bridge in a direction opposite plates 520, 522 and terminates in a hook-like extension 540 which projects out through a slot 515 (see FIG. 20) molded in the margin of the spring retainer 302 (FIG. 27) inside the barrel 10. The flat projection 56 can move only in the radial direction. The flat plates 520, 522 connected by the bridge 524 are assembled on the outside of the plunger plates 60-62. The bridge 524 has triangular recesses 530, 532 that come in contact with the triangular projections 70 and 72 on the plunger flanges 60 and 62. The plunger moves freely linearly between these flat plates. The flat projection 526 from the bridge passes under the needle holder arm 32, exits out of the barrel 10 and the hook-like extension or L-shaped lip 540 extending from the projection 526 turns back to engage the needle holder arm 32 at the distal end of the track 19 (FIG. 40). An additional slot (not shown) in the barrel 10 is provided for this purpose. This essentially locks the needle holder arm to the barrel via the spring retainer.

A displacement of the flat plate 524 out of the barrel track 19 by linear movement of plunger distally, releases the needle holder arm 32 and retracts the hypodermic needle 13 (and needle holder 14) in plunger channel 33. In the normal operating position, the plunger moves within the switch. When the entire medicine is injected and a final push is given to the plunger which advances the resilient cap 12 as well as compresses it. Triangular projections 70 & 72 of the plunger engage the recesses 530, 532 and causes movement of the switch 508 so as to release the needle holder arm 32 and cause retraction of hypodermic needle by the spring 300. A formed wire can replace the projecting flat plate 526 and lip 540. All that is required is a structure that can hold the needle holder against the spring force and anchor it to the barrel and be actuated by the plunger movement as described above.

Since the switch 508 is located inside the syringe there is no question of its separation from the device and therefore complies with regulatory requirements and/or recommendations. Those skilled in the art may device other specific switch constructions for accomplishing their goals without departing from the invention.

Each of the above-described switch arrangements accomplishes the above-stated objectives, as well as being non-removable. In this regard, when the latch or ring 308 is used to retract the needle holder, the plunger can be in any desired longitudinal position. For example, the plunger can be fully advanced, fully retracted, or at any intermediate position. This is advantageous because it might be desired to retract the needle after only a portion of a dose of medication has been injected into the patient, or it might be desired to retain all or a portion of a blood sample withdrawn from a patient within the syringe. With respect to the instant switches the plunger must be fully advanced to empty the syringe before the retraction mechanism is activated. To prevent the leakage of any fluid contained within the syringe at the time the needle is retracted, a latex seal (not shown) may be provided at the end of the nozzle 15. Also, the plunger cap 12 may be provided with a slit valve that engages the needle and prevents leakage. The nozzle also can be capped because the hypodermic needle is locked within the syringe. This retractable needle safety syringe is supplied sterile and ready to use.

During normal use of the needle-syringe assembly, the barrel 10 and the needle holder 14 are held stationary, and the plunger 11 is free to move axially relative to both the barrel 10 and the needle holder 14. Advancing movement of the plunger 11 is limited by contact of the plunger cap 12 with the end wall 23 of the barrel 10. The needle holder 14 is releasably locked to the barrel 10 by the locking engagement of the lateral arm 32 to the wall of the barrel by a latch such as the latch 308. Also, when used, the locking luer taper releasably locks the needle holder 14 to the barrel 10. The plunger 11 is also free to move longitudinally relative to the needle holder 14, because the needle holder is not locked to the plunger in that direction. However, the locking of the lateral arm 32 by the latch mechanism at the barrel wall, prevents rotation of the plunger. As long as the lateral arm 32 of the needle holder is locked to the barrel wall, the needle-syringe assembly is in its normal operating mode.

Following normal use of the needle-syringe assembly, the needle 13 can be retracted into the plunger 11 and the barrel 10. This requires axial movement of the needle holder 14 within the barrel 10 toward the proximal end thereof, which in turn requires that the needle holder 14 be unlocked for movement, under the influence of the biasing or retracting means such as spring 300, within the channel. Thus, to initiate retraction of the needle holder 14, the arm 32 is unlocked by releasing the latching mechanism 308, 408 or 508.

The illustrative syringe need not be any longer than a conventional syringe because conventional syringes are made longer than required to provide more than the desired fluid volume, so as to avoid inadvertent withdrawal of the plunger and the resultant spillage of the syringe contents. The extra plunger barrel length to accommodate the user's fingers in the space between the plunger knob and the finger flanges contributes to excess length in conventional syringes. In the present invention, the extended barrel length is used to lock and store the retracted needle holder and the entire needle.

FIG. 2 illustrates the assembled syringe and needle assembly with the cap 200 as it might be provided for use.

To operate the needle-syringe assembly, the protective cap 200 is removed from the needle 13, and the required amount of medication is aspirated into the barrel 10 without advancing the plunger. Air bubbles if any are removed and quantity of medicine is adjusted. Next, the injection site on the body of a patient is determined and the skin is cleaned with an antiseptic solution. Following percutaneous entry of the needle into the patient, location of the needle tip in the vein is confirmed by aspirating a small amount of blood into the transparent barrel 10. The plunger 11 is then advanced to inject the medication from the barrel 10 into the vein. After the medication is administered, the needle 13 is withdrawn from the patient, the latch mechanism 308 (408, 508) is released and the spring 300 or other retracting means retracts the needle holder 14 and the needle 13 and locks the needle holder in the plunger detent 75. With the needle 13 completely retracted inside the barrel 10, all the components of the syringe are automatically interlocked and non-reusable, and the needle-syringe assembly can be safely discarded in its entirety. The cap 200 can be replaced to prevent leakage of any remaining fluid within the barrel 10.

It can be seen from the foregoing description that the needle-syringe assembly performs all the conventional functions of injection syringes and yet, upon completion of injection, the hypodermic needle 13 is concealed within the barrel 10. The needle-syringe assembly with switch 308 can receive and dispense medications any number of times for a given patient by reciprocal longitudinal movement of the plunger 11 within the barrel 10. However, once the latch is released it cannot be reused.

The needle-syringe assembly of this invention is easy to manufacture, cost effective, and easy to use in the field. The parts can all be made by conventional plastic molding and using readily available medical grade stainless steel needles and compression springs. The plastic parts are made by injection molding of medical grade, gamma stable polymers such as polypropylene. The needle holder and spring retainer that require higher strength are molded from polycarbonate. The plunger seal or cap and "O" ring can be molded from non latex thermoplastics synthetic elastomers or silicones. The switches that require smooth friction free movements is made from HDPE. Of course the material selection is guided by the strength and functional requirement of components. The disclosed materials can be substituted by alternate or improved compounds that may or may not be presently available. The needle is glued by using ultraviolet cured adhesives. Syringes are assembled and packaged in a clean room and sterilized by gamma radiation.

While the drawings of components and description, for simplicity, show a syringe with central nozzle, the axis of all the components can be shifted to generate a syringe with an eccentric nozzle without altering the concepts or components. Likewise, the cross-sectional shape of syringe components can also be modified without deviating from inventive description.

Because of the unique features of this invention the method of assembly is modified from the conventional syringe assembly. The method is illustrated in FIGS. 42-49. The pre-capped plunger is oriented with open channel 33 facing up, is placed on a peg passing through the proximal window of the plunger while spring retainer half 302a is placed under the plunger. Since the proximal part of the plunger channel has a detent 75 that interlocks with the retracted needle holder, their contact is prevented by placing a spacer 602 between the components to prevent interlocking (FIGS. 43-44). The spacer is placed in the plunger channel and is taken out only after the assembly, by pulling the plunger out of the barrel. A sub-assembly consisting of the needle holder surrounded by the compression spring and spring retainer is then placed in plunger channel 33. Insertion of the plunger containing the foregoing assembled components in the barrel completes the assembly by rearranging each component because of the localized restrictions and structural geometry of the barrel.

Figure 45:
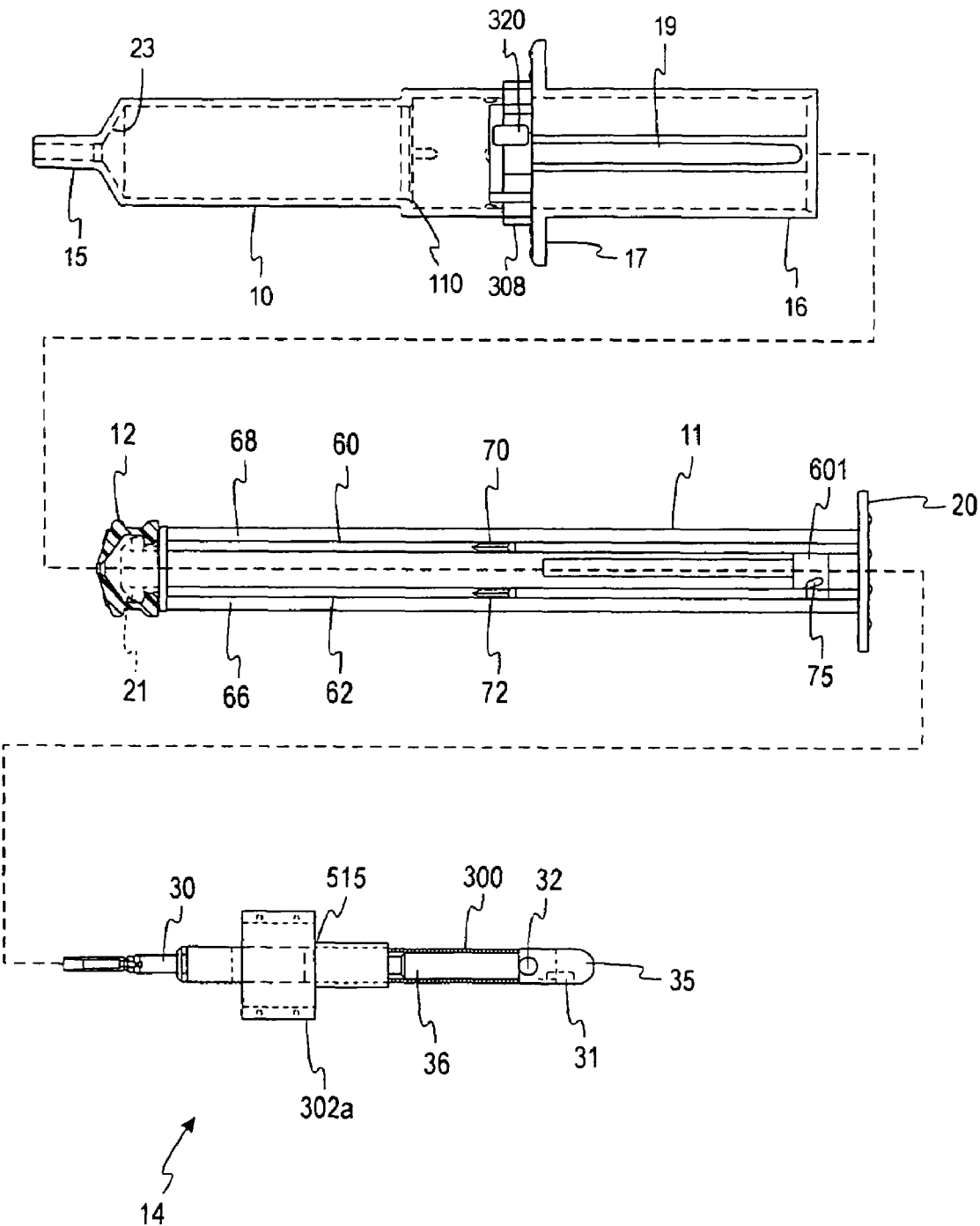
Figure 48:
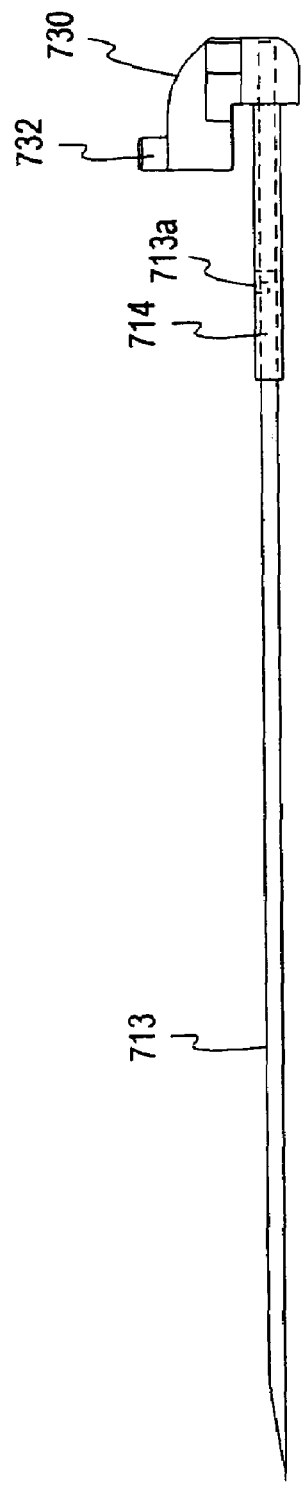
FIGS. 48 and 49 illustrate a needle and over-the-needle catheter for use in an alternate embodiment of the syringe of the invention for placement of an over-the needle (OTN) catheter.
Figure 49:
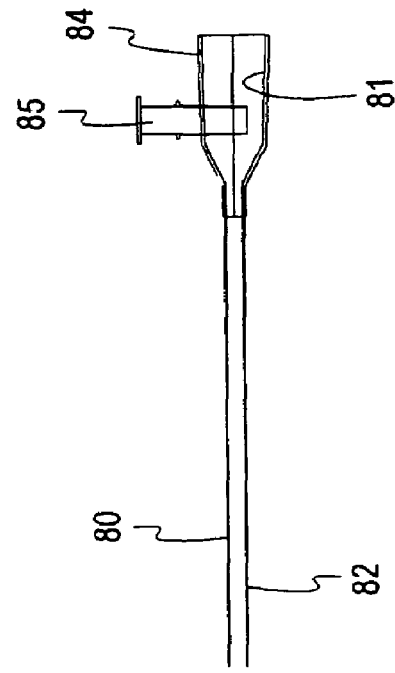

In FIG. 42, the switch 308 is inserted on the barrel 10 from the nozzle 15 side past the detent 100, and rotated 160 degrees, ready to receive and lock the Needle Holder Arm. In FIG. 43, the rubber cap 12 is aligned and pressed on the plunger 11. Spring retainer 302 is aligned under the plunger 11 adjacent to the distal plunger plate 25. In FIG. 44, the plunger with open channel 33 is placed on a square indexing pin 600 passing through a detent window or opening 601 in the plunger provided for this purpose. It blocks the detent 75 and keeps plunger channel open for assembly of parts. Also, a spacer rod 602 is placed in plunger channel adjacent to the square indexing pin. In FIG. 45, a sub-assembly including the needle holder and spring 300 inserted into the spring retainer 302 is placed in the plunger channel next to the spacer rod 602, and the spring retainer parts 302a, 302b are snapped together. In FIGS. 45-46, the plunger assembly is inserted in the barrel 10 and switch 308 is rotated to lock the needle holder arm. All the components are now properly re-arranged, aligned and assembled automatically. In FIG. 47, the plunger 11 is pulled out to discard the spacer rod 602.

Because the needle holder 14 is retracted directly into the plunger 11 itself, the rather than into the barrel cavity, the plunger 11 need not be fully extended out of the barrel for needle retraction to occur. Thus, when discarded following use, the needle-syringe assembly contributes minimally to the bulk of refuse. Since retraction of the needle 13 is effected by the spring or other elastic biasing means, upon releasing the latch, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, etc. to conceal the needle following use.

Intravenous Catheter Insertion Syringe.

Intravenous access is a lifeline of critically ill patients as a primary avenue of administration of fluids and medicines, yet it can be a difficult procedure. There is therefore a need to place a catheter consisting of a non-traumatic flexible polymeric tube in a patient's vein. Since polymeric catheters, although non-traumatic to veins, can not penetrate the skin and vein, a hypodermic needle has to be used first to create an initial puncture and guide the catheter by sliding over it. This over-the-needle (OTN) catheter placement syringe is disclosed in FIGS. 48-54 and has essentially the same components of the retractable needle syringe as shown and described above. However, the needle holder 14 is replaced by an integral needle 713 which also functions as needle holder 714 and has all the functional features of the above-described needle holder 14 including a side hole 713a located in barrel cavity close to the nozzle. The remaining proximal part of the needle 714a is blocked beyond the side hole 713a. It has an insert-molded head 730 to support the spring 300 as well as side arm 732 to engage to the barrel via a switch. The "O" ring 202 is replaced by a synthetic elastomeric gasket 702 press fit in the nozzle 15 of the syringe. A step between the needle and needle holder is avoided to prevent back flow of the fluids when the plunger is advanced over the retracted needle that has a smaller diameter than the opening in the rubber stopper.

Veins are mobile and slippery structures. They are also tortuous. Hence a straight hypodermic needle cannot be pushed too far because of the danger of double puncture. A soft and non-traumatic catheter, once in vein can however be advanced for longer length. However, it is also essential to confirm that the fluid path is continuous, and that the catheter is in vein. A free flow of the heparinized saline indicates that the catheter is located in the vein and that it is open. Heparinized saline also prevents the clotting of blood in catheter as well as the vein. Infusion of heparinised saline as soon as venous access is obtained to prevent clotting of the vein by blood is a good strategy and is universally followed. Saline filled syringe to obtain venous access is good practice, and will be clear from the method of use depicted in FIGS. 50-54.

In FIGS. 48-54, over-the-needle ("OTN") catheter assembly includes an OTN catheter 80 and the above-described syringe assembly with a hypodermic needle 13 modified as noted above mounted therein. The catheter 80 is a polymeric catheter having an elongated tip 82. Prior to use of the OTN catheter assembly, a proximal end female connector 84 of the OTN catheter 80 is coaxially mounted over the nozzle 15 and the hypodermic needle 713 protrudes through both the nozzle 15 and the OTN catheter 80. Prior to and during normal use of the OTN catheter assembly, the OTN catheter 80 is held engaged over the nozzle 15 of the syringe assembly by suitable means, such as locking luer tapers on the outer surface of the nozzle 15 and the inner surface 81 of the end 84 of the catheter 80. The elongated tip 82 of the catheter 80 follows the beveled tip of hypodermic needle 713. Prior to use, i.e., prior to inserting the needle 713 and catheter tip 82 into a vein, the needle 713 and catheter tip 80 are enclosed by a removable cap similar to the cap 200.

The illustrated embodiment of the catheter 80 includes an internal valve 85 that normally closes the cavity of the female luer end 84 of the catheter to prevent back flow of blood when disconnected from syringe or fluid line. The valve 85 opens to permit the entry of the nozzle end of the syringe and permits fluid communication. It again stops the back flow of fluids when the syringe nozzle is withdrawn from the catheter. When another fluid line that also has a male luer end is subsequently connected to the luer end 84, the valve 85 may be opened to permits fluid communication.

The purpose of the locking means, such as luer tapers, is to assure mechanical unity of the syringe with the OTN catheter so that insertion force applied to the syringe barrel is directly transmitted to the hypodermic needle 713 and catheter 80. Release of the locking luer taper disassociates this mechanical unity, permitting the syringe (with the retracted needle 713) to be removed from the catheter 80.

To use the OTN catheter-syringe assembly, as shown in FIGS. 50-54, the skin of a patient is first prepared and a peripheral vein 800 is made prominent and cleaned with antiseptics.

Under aseptic precautions, the OTN syringe cap 200 is removed and syringe is partially filled with heparinised saline. The vein is punctured with the needle 713 projecting at the catheter tip 82 (FIG. 51), and the location of the needle tip is judged by the change in color under the catheter or by the appearance of blood in the catheter and/or the flashback or aspiration of blood in the syringe.

Once the location of the needle tip in the vein is confirmed, by aspiration of blood and injection of saline in the vein, the needle holder is retracted by release of the switch as described above (FIG. 52). At this stage the plastic catheter can be advanced in the vein without fear of trauma since the sharp needle is already retracted, in the manner described above.

Continuity of catheter and its location and, confirmation that the needle 713 and catheter tip 82 are located in the vein can be made by viewing blood entering the catheter 80 by capillary action. It, however, is also possible to confirm a flashback within the syringe barrel by partially retracting the plunger 11 relative to the barrel 10 to assure that continuity between the barrel nozzle 15 and the vein is still established. In this regard, the side aperture of the needle holder 714 opens into the syringe. Confirmation of proper insertion in the vein therefore is indicated by blood entering the barrel chamber via the side aperture in the needle holder 714.

When fluid path is continuous, the entire heparinised saline in the syringe is infused in the vein to fill the vein with anticoagulants to prevent clotting.

While securing and retaining the OTN catheter 82 in the vein, and blocking the female end of OTN by the valve 85 the syringe assembly is removed (FIG. 54) and an intravenous line is connected to the catheter 80, as conventional. Finally, the catheter 80 is secured to the skin of the patient by adhesive tape. The syringe with the retracted and locked needle is then disposed of as biological waste. In order to prevent leakage of the fluid the syringe may be capped.

Without the improvements recited herein it was not possible to ascertain with certainty [1] the catheter is in fact in vein after the puncturing needle is withdrawn [2] that there is no false passage [3] that the vein is filled with anti-coagulant saline and that it is open—not clotted.

The various novel and improved syringe assemblies as described above offer a number of advantageous features, including but not limited to various combinations of the following:

The plunger channel 33 adds precision to the needle holder movement. For example, straight axial retraction of the needle in the plunger channel 33 avoids angulation of the needle and puncture of the barrel cavity. It does not require extending the overall length of the syringe as a result of the plunger being pulled out, and avoids the need for special measures such as breaking the plunger to prevent re-use. The linear movements of the plunger in the barrel are mechanically indexed to actuate retraction of the needle after the medicine is injected in the patient.

The number of the components in the present invention is not significantly different from a conventional syringe to keep it cost effective.

Use of the sliding needle holder eliminates the usual female needle holder on the barrel nozzle, which eliminates the associated dead-space and quantity of wasted medications left over in the syringe nozzle and the conventional needle holder.

The operation of the syringe is one-way so that accidental misuse is minimized, i.e., once retracted the needle holder is locked in place, so the needle cannot be re-extended.

Operation of the syringe is particularly safe because all the required manipulations of the various parts of the syringe are performed at or near the proximal end of the syringe, well away of the needle, during both the normal and retracting modes of operation.

In the rare event when only a partial dose of medicine is given to the patient, the syringe with leftover medicine can be rendered safe by retraction of the needle holder, while capping of the nozzle will prevent spillage.

It should be noted that the syringe assembly as described may be used to dispense medication or as a blood collection device. It may also be used to place an over-the-needle catheter, as described above.

With a few innovative modifications, present invention can be converted into a pre-filled retractable needle, single use safety syringe. These syringes are used in the pharmaceutical industry. Instead of packaging the injectable medications in vials or ampoules the sterile medications are filled in the syringe itself. It saves the entire packaging cost of ampoules and vials, as well as cost of professionals, who transfer the medication from the vials to the syringes in sterile atmosphere, before it is injected in the patients. With a pre-filled syringe, it is just inject the medicine and dispose of the syringe. One of the major problems involved in the pre-filled syringe technology is the compatibility of the syringe components with the medications stored in syringe for long shelf life. Newer plastics that can be used in this invention are sufficiently neutral, non-reactive and address that problem. A second consideration is that the medicine filled in a syringe should not leak, either from nozzle end or from rubber piston end. Further, the sterility of medicine must be preserved, and an accidental discharge of medicine must be avoided, until use. In addition, the syringe used to inject the medicine in patient must comply with the "needle stick" prevention regulations mentioned above.

Prevention of fluid leak is an important function of the syringe. The problem is that of maintaining a seal at either end over a long period of time. The nozzle of the present syringe invention can be provided with male (external) luer taper to install a tight fitting cap 200 with female (internal) luer taper for protection of needle point, as well as preventing accidental needle stick, because the hypodermic needle emerges from within the nozzle. The luer taper lock requires an intentional compound roto-linear movement to disengage. It therefore resists vibratory as well as other forces ordinarily tending to separate the components.

A luer lock when re-enforced with a screw thread molded on contacting surfaces of the nozzle 15 as well as inside cap 200, is further assurance that cap would not separate once installed to maintain the seal. The protective cap 200, intended for the pre-filled syringe, is in addition partially filled with a nontoxic, tissue-compatible, inert, elastic non coring, material such as silicone to an appropriate length sufficient to enclose the tip portion part of the hypodermic needle of the retractable needle syringe. When such a needle protector is installed on the nozzle of the retractable needle syringe, it assures a perfect seal both to prevent the leak of air as well as any fluid contained within the pre-filled barrel despite a modest in-advertent push on the plunger.

The rubber piston 12, installed on the plunger head 21, seals the needle holder in its center and seals with the barrel along its periphery. When the syringe is pre-filled with medicine, the rubber piston is supported by the spring retainer 302. Further, the needle holder anchors it to the barrel of the syringe. Accordingly, the plunger and the rubber cap cannot be pulled out beyond this pre-filled location, unless this locking mechanism is intentionally and voluntarily disabled, so there is no chance of a leak from the proximal end.

The effective sealing at the nozzle as well as the above-mentioned mechanical anchoring of the rubber piston is not likely to permit movement of the plunger to effect a fluid leak. However, another barrel-plunger lock mechanism consisting of a clip that anchors to the barrel and a 90 degrees angled plate that engages with the linear slots on the proximal part of the plunger flange 64 immobilizes the plunger in relation to the barrel. This prevents any inadvertent pull or push to be transmitted to the medicine chamber and assures additional security against advancement of plunger within the barrel.

Since prefilled medicine obligates that the plunger be pulled out, and since the pulled out plunger is unprotected because it is out of the barrel, this assembly is further fortified. Referring to FIGS. 73-77, the plunger portion 111 projecting out of barrel 10 is split in two halves 111a, 111b. Each half is provided with a hinge 113a, 113b that permits each half to be folded by the side of the barrel (see FIG. 77). The hinge mechanism is such that in normal use the hinge gets pushed within the barrel and can not come out nor can it be unfolded unless pulled out of the barrel. This mechanical arrangement offers ultimate security to the operation of the prefilled syringe.

The mechanical structures of the present invention described herein assure that the retraction mechanism cannot be disabled by the hydraulic pressure generated inside the barrel. Operation of a pre-filled syringe is simple in that everyone removes the protective cap before injection, and plunger lock invariably reminds one to rotate the locking ring to initiate the injection of medicine under aseptic precautions.

FIGS. 55-64 and FIGS. 65-71 illustrate two further embodiments of a retractable needle, single use safety syringe in accordance with the invention. These two additional embodiments differ from the embodiments heretofore described, in that the latch or switch arrangement is entirely internal to the barrel 10 of the syringe. The barrel therefore has no need for and therefore omits the slot or guide track 19 shown in the previous figures of drawing. In this regard, the barrel for use with the embodiment of FIGS. 55-64 is generally cylindrical and circular in cross-section without any breaks in the outer wall, as indicated generally by FIG. 63, while the barrel for use with the embodiment of FIGS. 65-70 is of the type shown in FIG. 68, with an enlarged wall portion 29 along one side thereof, similar to the barrel shown in FIGS. 8 and 9 described above, however, without the detent elements 100, such that the external surface is relatively smooth, having one enlarged diameter segment at the extended or radially outwardly extending wall portion 29.

Referring initially to FIGS. 55-58, an alternate embodiment of a two-piece spring retainer element 1302a, 1302b is illustrated. The elements 1302a and 1302b become one structure when snapped together. They can also be molded as a single piece with an identical function. The spring retainer element 1302a is similar to the spring retainer shown in FIGS. 20 and 21, in that it includes a generally semi-cylindrical body portion 812 having connector members 814 which mate with similar or complementary connectors on the second spring retainer element 1302b. The spring retainer element 1302a also includes an extension 1303 which terminates in a spring support or retaining element 1310 with a through opening for receiving the needle holder axially movable therethrough. An oppositely projecting extension 1312 functions to engage the needle holder within the plunger channel in fixed position in normal operative state. It retracts the needle holder at the point of plunger advance when the ramps deflect the plate radially. This structure eliminates the requirement of a switch for causing retraction and can be used with a conventional barrel.

Figure 62:
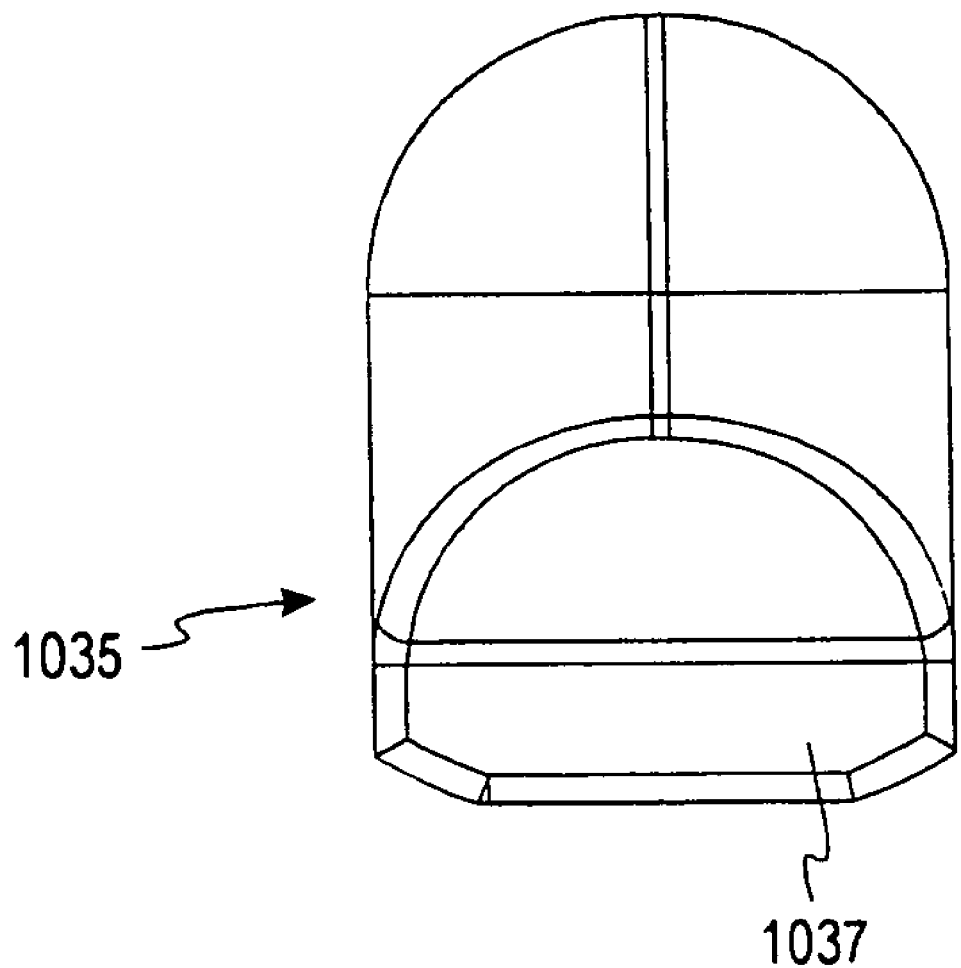
FIG. 62 is an enlarged top view of the spring retainer of FIGS. 60 and 61.
Figure 63:
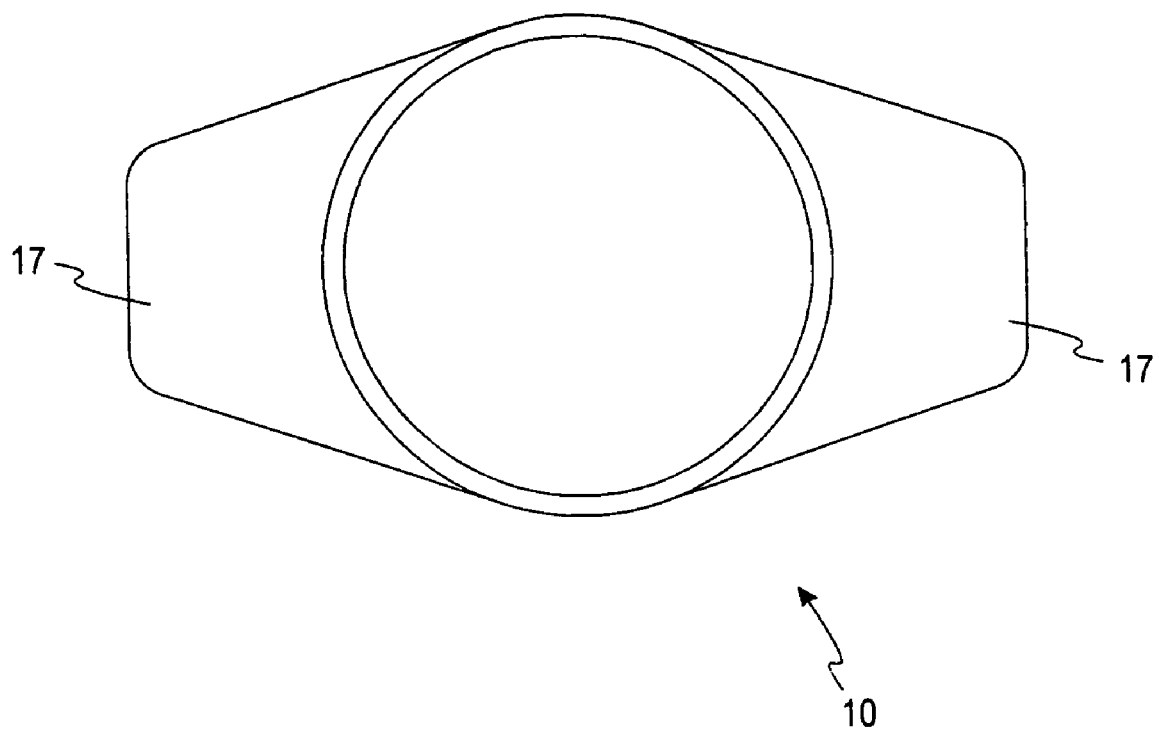
FIG. 63 is a top view of another embodiment of a barrel.

In this regard, the extension 1312 terminates in a gripping lip or flange 804 which has a right angle 805 (that is, at right angles to the extension plate 1312) for overlying a complementary flat surface portion 1037 at a top surface of a needle holder element 1014 shown in FIGS. 60-62, and further described below. The retaining lip 804 also has a leading beveled surface 806 to facilitate initial passage of the enlarged head 1035 of the needle holder 1014 thereby for engagement with the flat top portion 1037 of the top surface of the enlarged head 1035 of the needle holder 1014 (see FIGS. 60-62).

The extension 1303 has a semi-cylindrical channel 810 for receiving and holding in place the compression spring 300 described above.

The proximal extension plate or wall 1312 has opposing side surfaces 802 located and sized so as to span over the walls 60, 62 of the channel 33 of the plunger 11. An upper edge surface of the plate 1312 to either side of the retaining lip 806 has a generally V-shaped, ramped groove 808 which is of complementary form for gaging the upper ramped and V-shaped surfaces of the projections 70 and 72 of the plunger 11.

Figure 55:
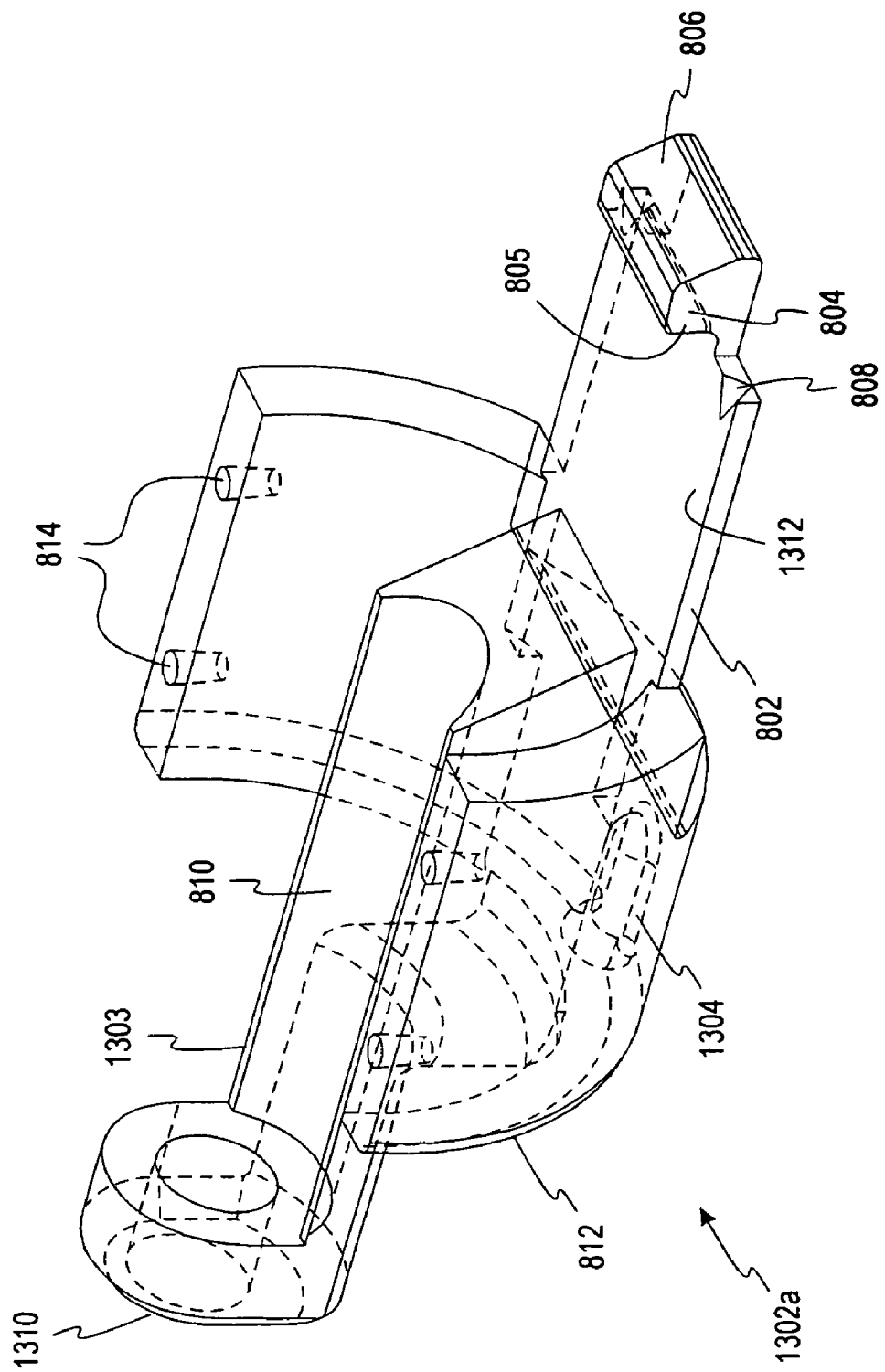
FIG. 55 is an isometric view of another embodiment of a spring retainer.
Figure 56:
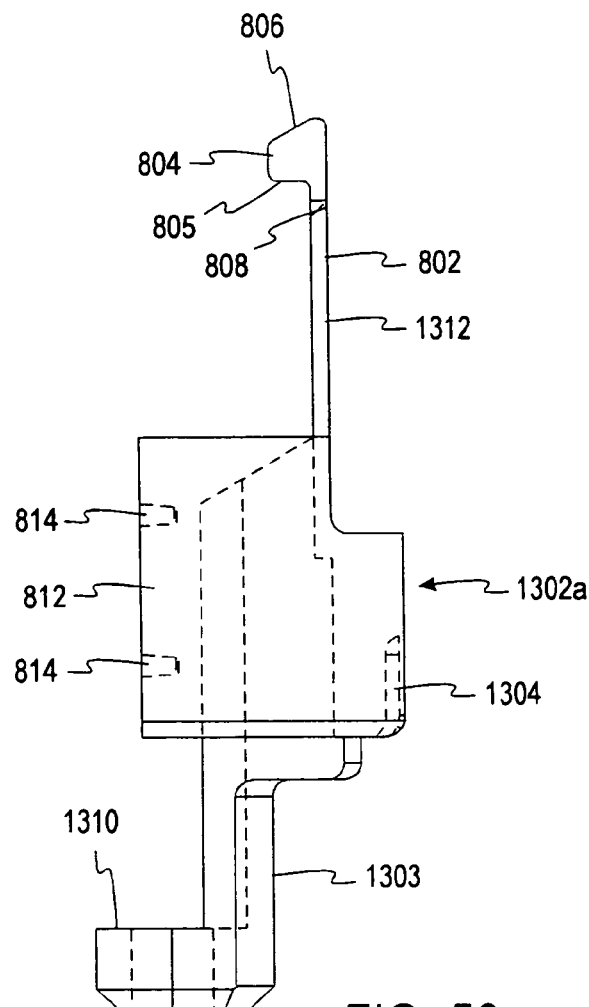
FIG. 56 is a side elevation of the spring retainer of FIG. 55.
Figure 57:
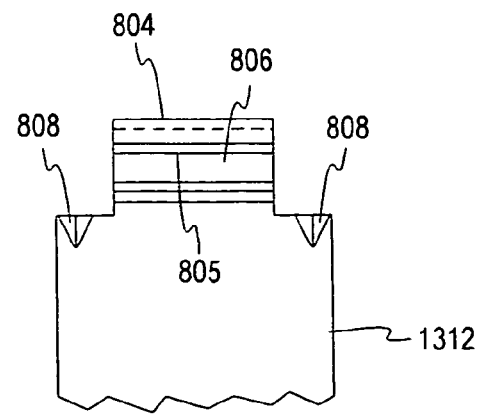
FIG. 57 is a partial front elevation of the spring retainer of FIG. 55.
Figure 58:
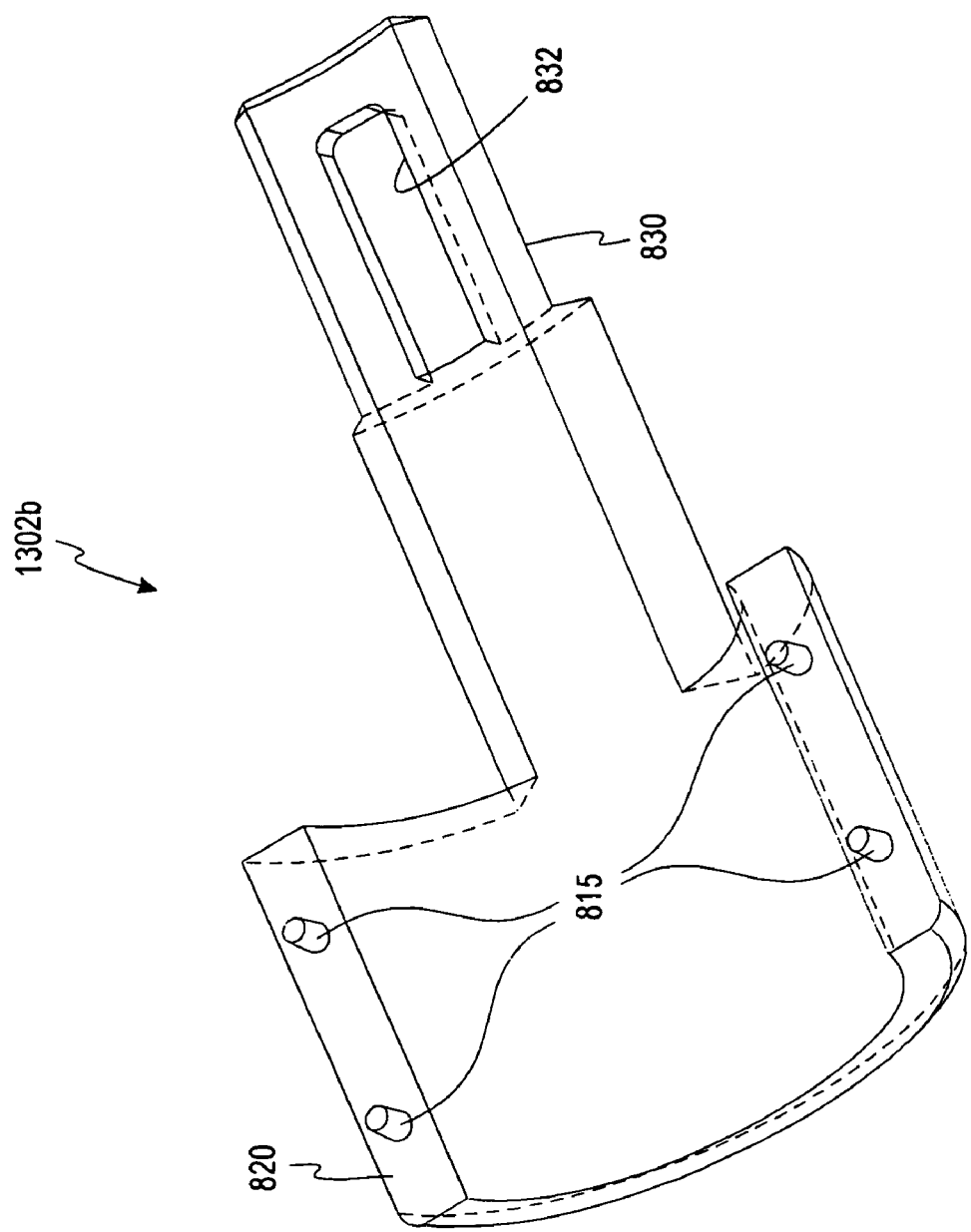
FIG. 58 is an isometric view of a second piece of the spring retainer of FIGS. 55-57.
Figure 59:
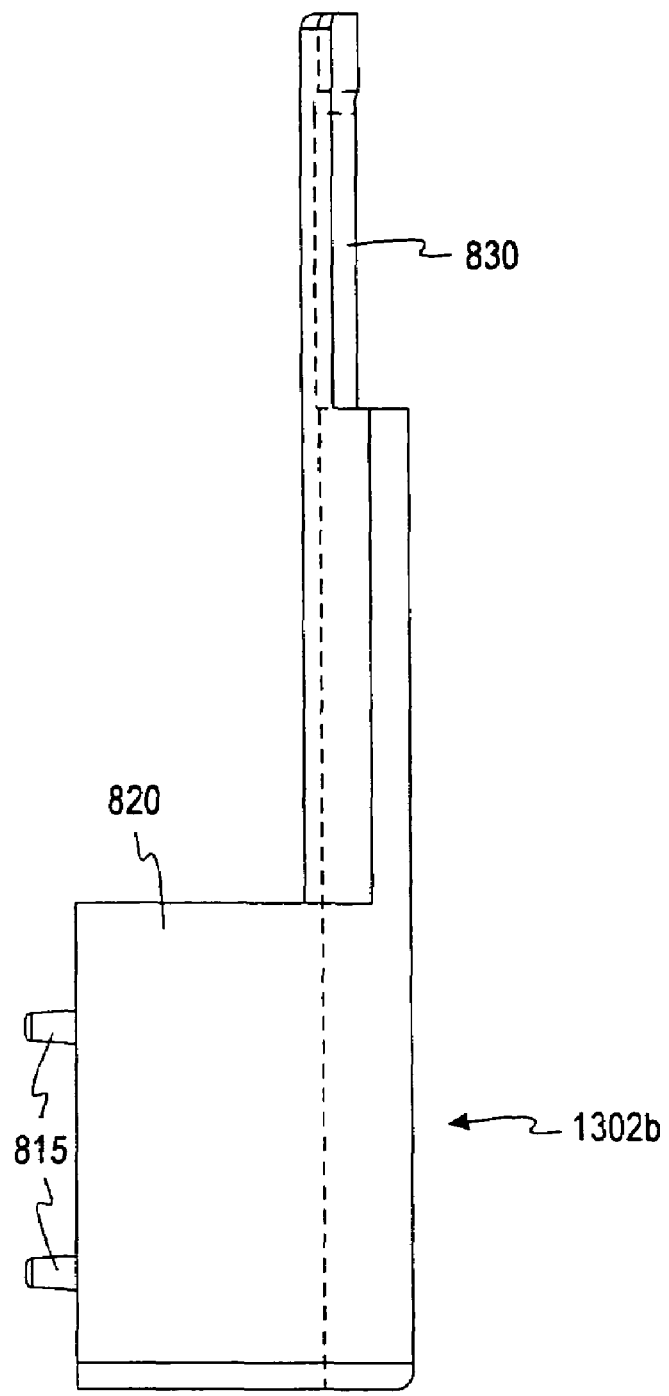
FIG. 59 is a side elevation of the spring retainer portion of FIG. 58.

Referring briefly to FIGS. 58 and 59, the second segment or portion of the spring retainers indicated by reference numeral 1302b and has a semi-cylindrical portion 820 which has mating projections 815 for engaging with the apertures 814 in the portion 1302a shown in FIG. 55 to assemble the two portions of the spring retainer together. In other respects, the spring retainer 1302b is substantially identical to the spring retainer element or portion 302b. However, the spring retainer portion 1302b has an additional axially extending reduced thickness portion 830 which has an elongated window 832 for interfitting with a detent 842 formed in a bottom rib 64a of a modified plunger 11b (see FIG. 72) which includes a ramp 840 which leads into a recess 842, such that the ramp 840 will pass into and engage the window 832 upon the over-extension or over-advancement of the plunger for retraction of the needle as described above. The reduction in the thickness of extension plate 830 offers a spring-like action for positive engagement of the detent 842 on the rib 64 of the plunger.

Figure 64:
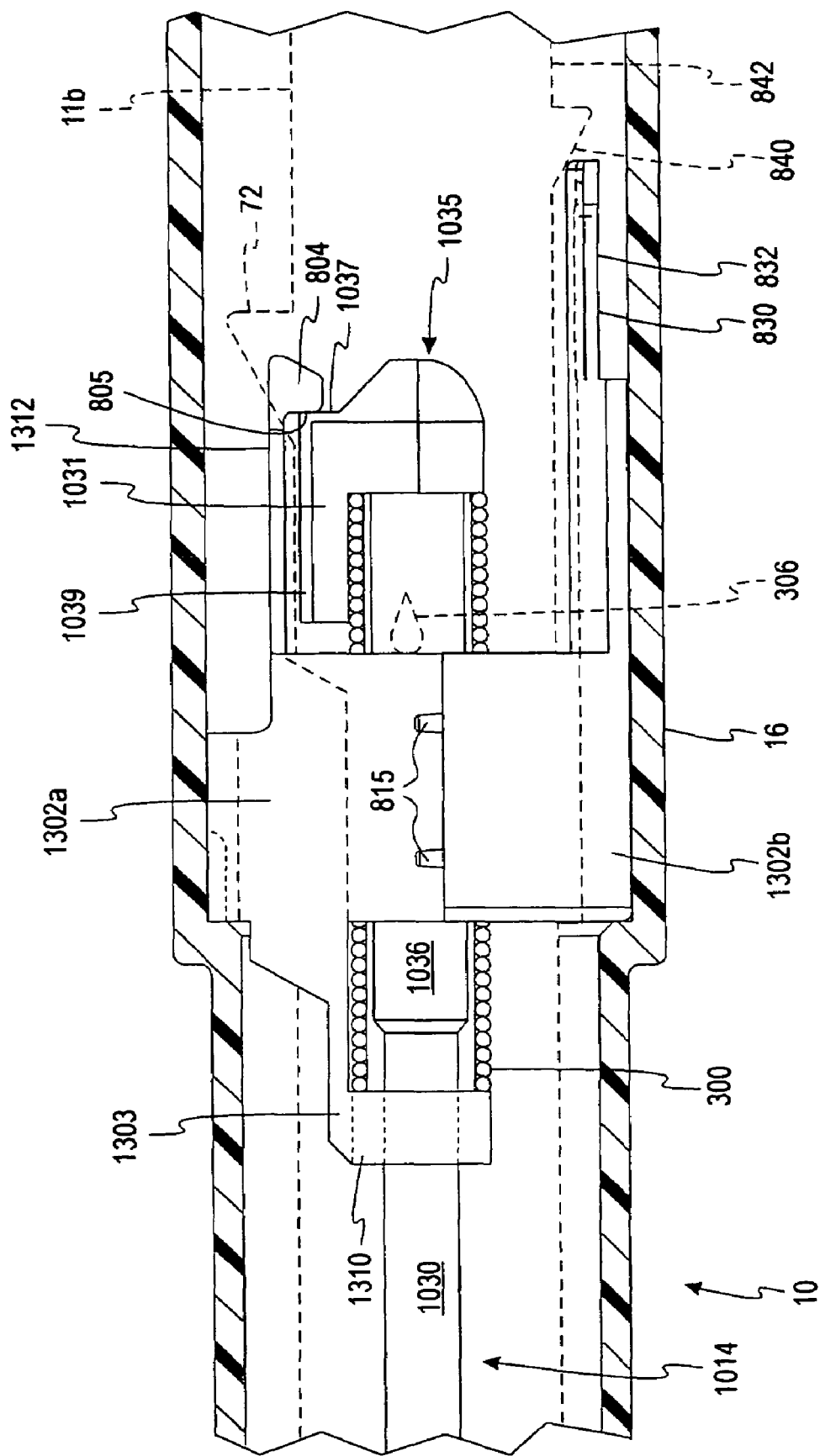
FIG. 64 is a partial view of an assembled syringe, partially broken away, illustrating assembly of the components of FIGS. 55-63 therewith.

Referring briefly to FIG. 64, the elements of FIGS. 55-63 are shown in assembled condition. Upon the above-described over-advancement of the plunger 11, the projections 70 and 72 engage the grooved edges 808 of the extension 1312, resiliently bending back the top portion of the plate so as to release engagement of the retaining lip 806 from the flat area 1037 on the top 1035 of the needle holder 1014, thereby allowing the spring 300 to expand and retract the needle holder and needle. As also shown in FIG. 64, when this occurs, the detent comprising the ramp 840 and recess 842 engages the window 832 to hold the assembly in a locked condition so as to render it completely locked and nonreusable and prevent retraction of the plunger, as well.

Figure 66:
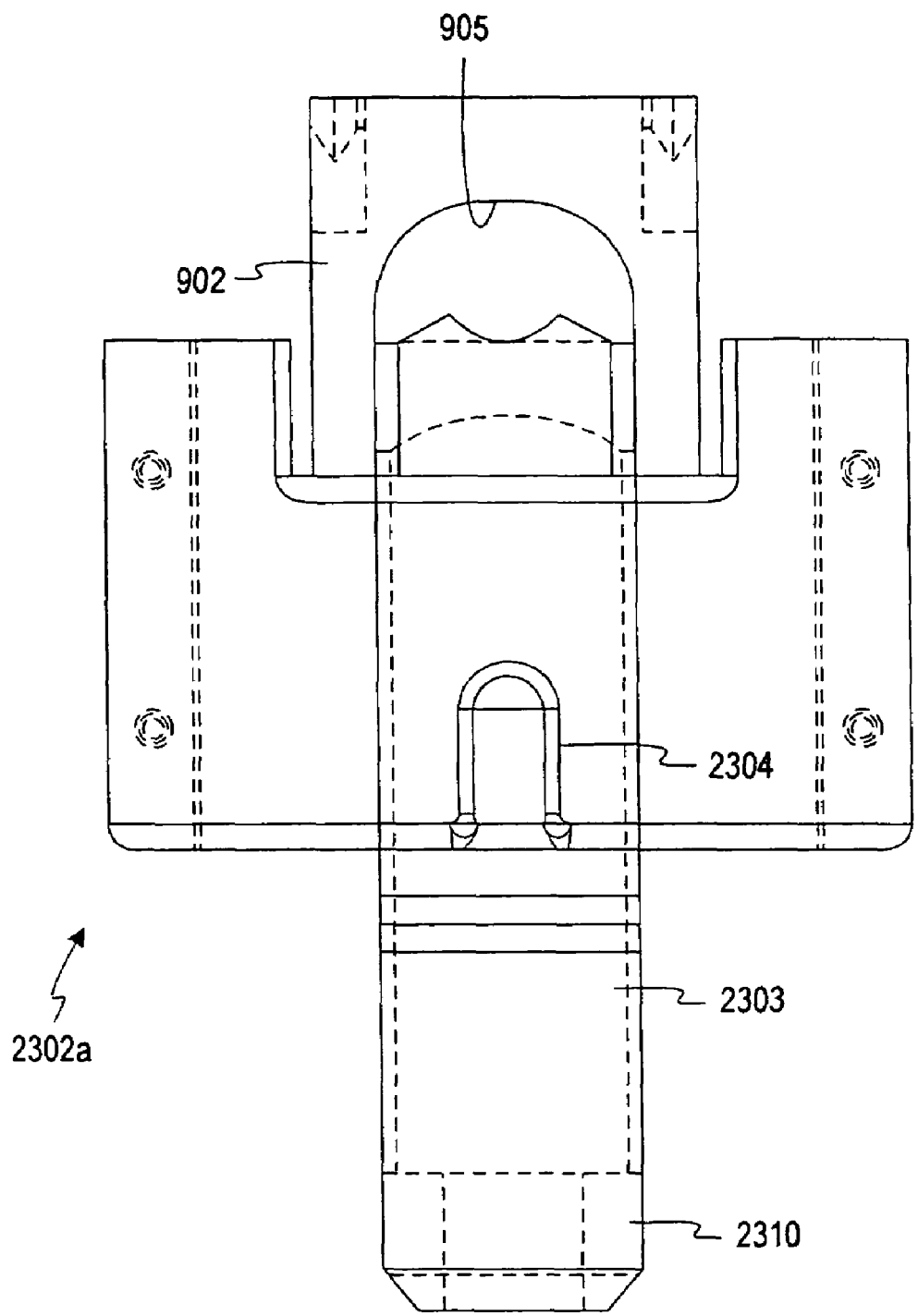
FIG. 66 is a rear elevation of the spring retainer element of FIG. 65.
Figure 67:
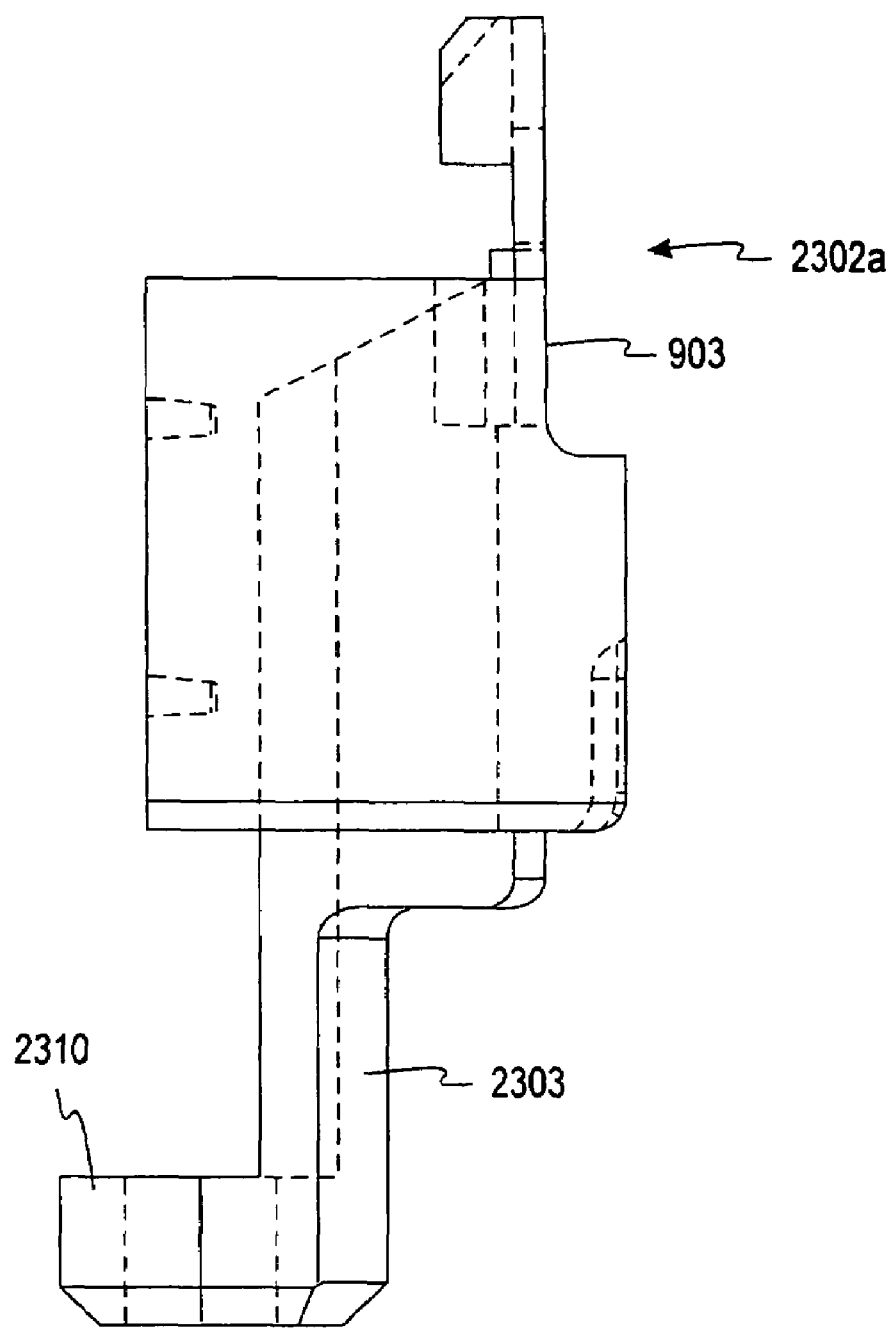
FIG. 67 is a side elevation of the spring retainer element of FIGS. 65 and 66.
Figure 68:
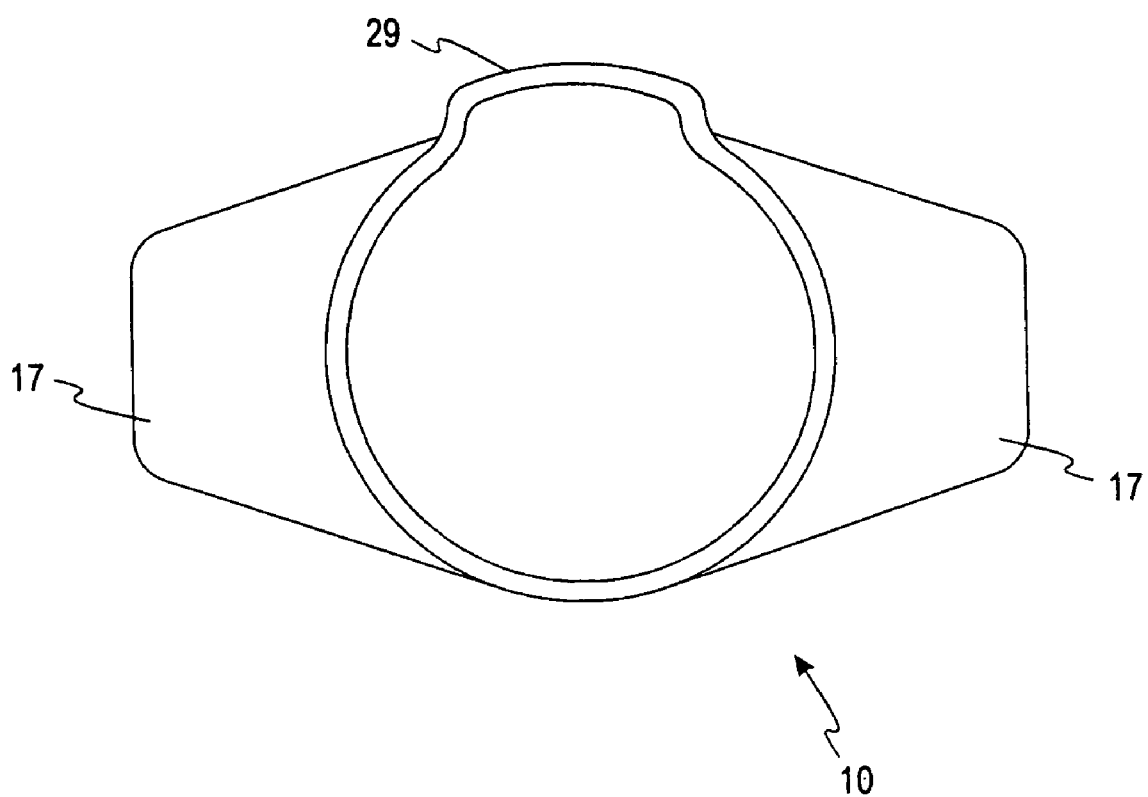
FIG. 68 is a top view of another embodiment of a barrel.

Referring next to FIGS. 65-70, another embodiment of a spring retainer 2302a, needle holder 2014 and barrel 10 for achieving for "instant" retraction entirely internally of the barrel, is shown. This embodiment, as also shown in the assembled view of FIG. 71, operates for releasing the needle holder to retract the needle and locking the components, including the plunger, in place in similar fashion to the embodiment of FIGS. 55-64 described above. That is, all of the mechanisms are carried internally of the barrel whereby no channel, slot, track or other opening in the barrel is needed or provided. In order to accommodate the mechanism of this embodiment, however, the barrel has a radially narrow increased diameter portion 29 as shown in FIG. 68, and mentioned above.

Figure 65:
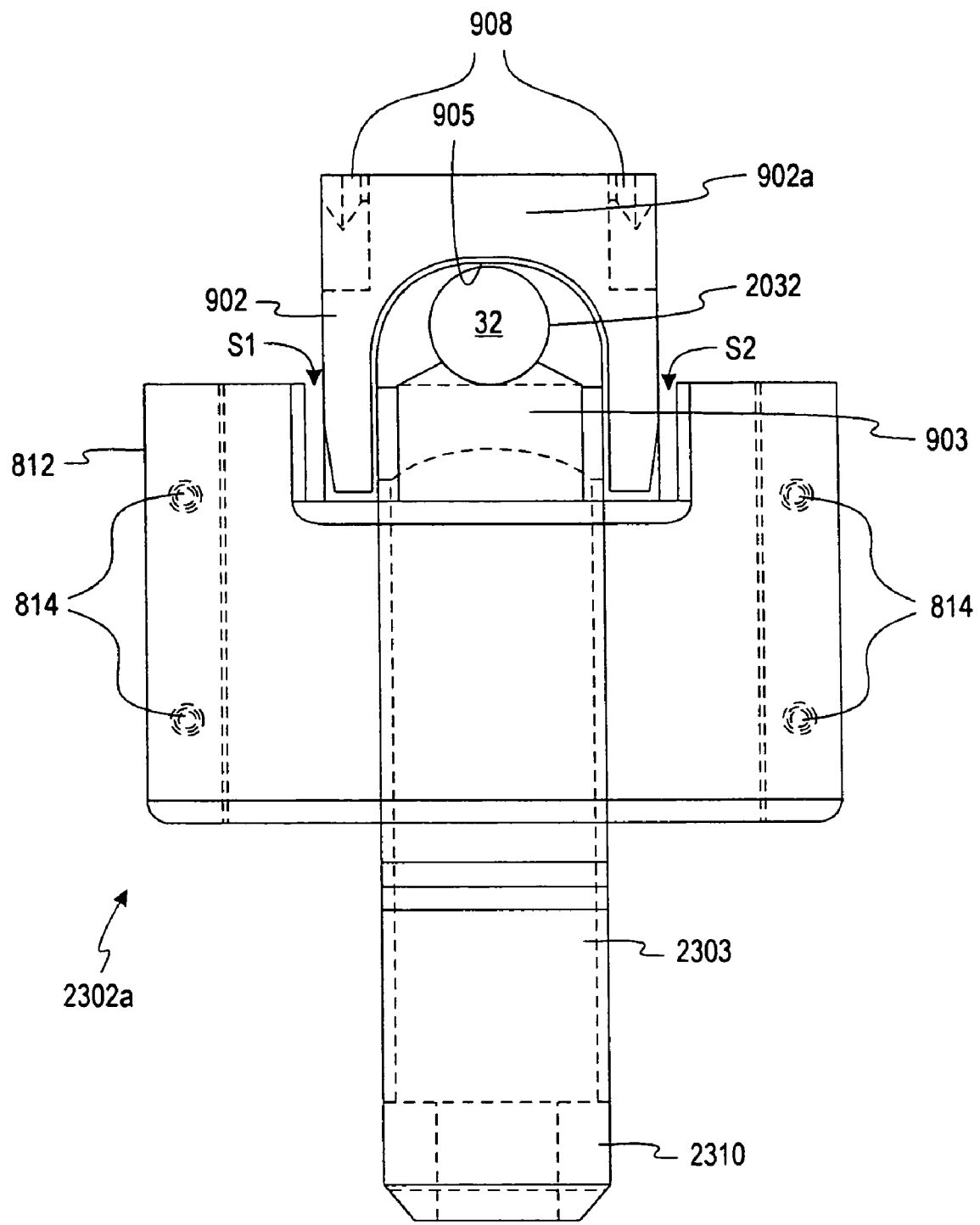
FIG. 65 is a front elevation of another embodiment of a spring retainer element portion which may be coupled with the second retainer portion shown in FIGS. 58 and 59 to form a spring retainer element in accordance with another embodiment of the invention.
Figure 71:
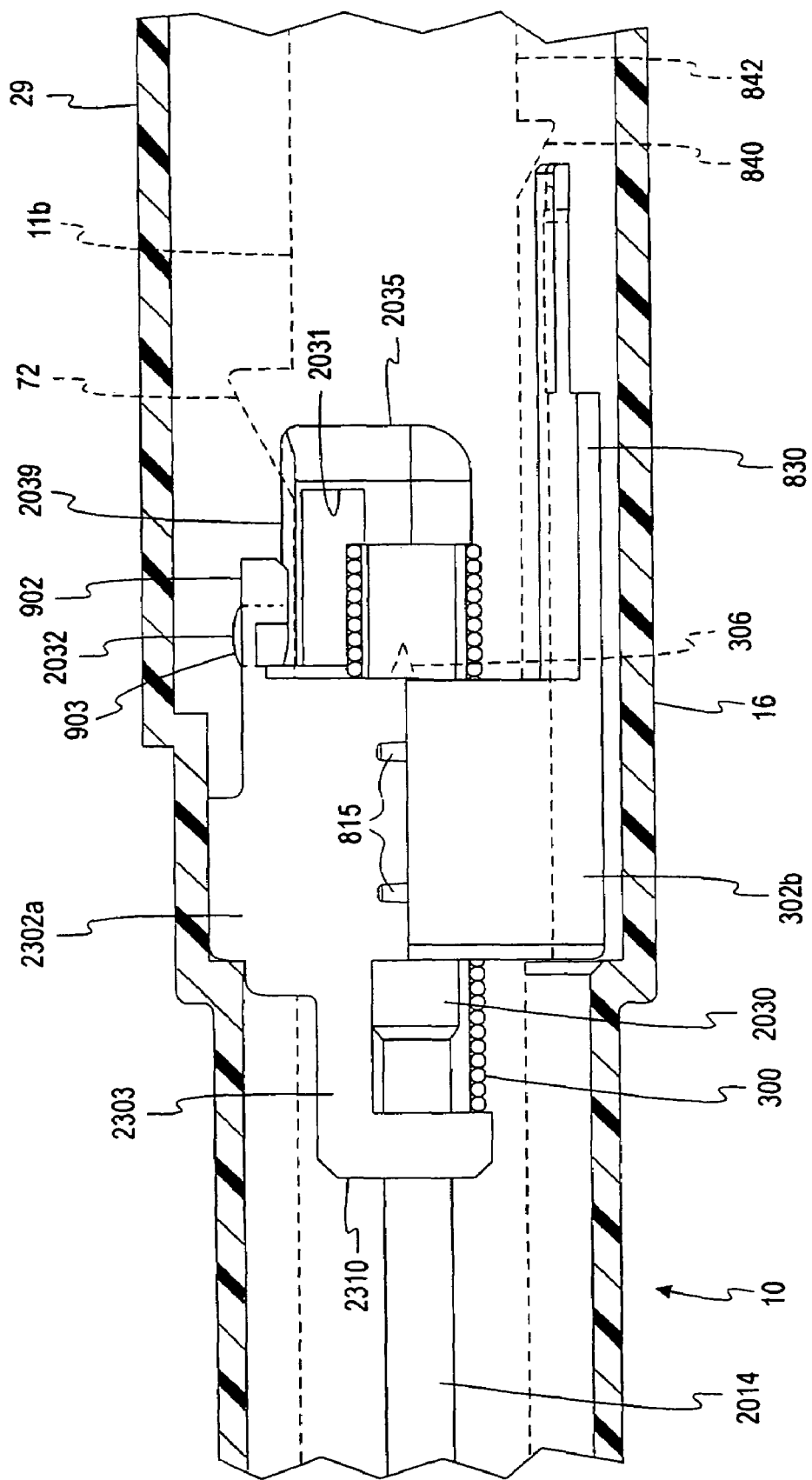
FIG. 71 is a partial view of an assembled syringe, similar to FIG. 64 showing the spring retainer and needle holder components illustrated in FIGS. 65-70.

Referring initially to FIGS. 65-67, the spring retainer portion 2302a interfits with the spring retainer portion 1302b as shown in FIGS. 58 and 59. In this regard, the window 832 in the spring retainer element 1302b interlocks in the same fashion as described above with respect to the detent portion 840, 842 of the plunger 11b of FIG. 72, as also illustrated in FIG. 71. In this regard, the spring retainer portion 2302a includes a semi-cylindrical portion 812 which interfits snugly within the interior wall of the barrel 10 and is retained in place by a raised ring 120 as mentioned hereinabove. An extension 2303 and spring supporting portion 2310 with through aperture for receiving the needle holder are the same as in the above described embodiments. Also, as in the above described embodiments, a small slot or groove 2304 interfits with a mating projection within the barrel to properly index or position the spring holder and prevent rotation thereof with respect to the barrel 10.

Figure 72:
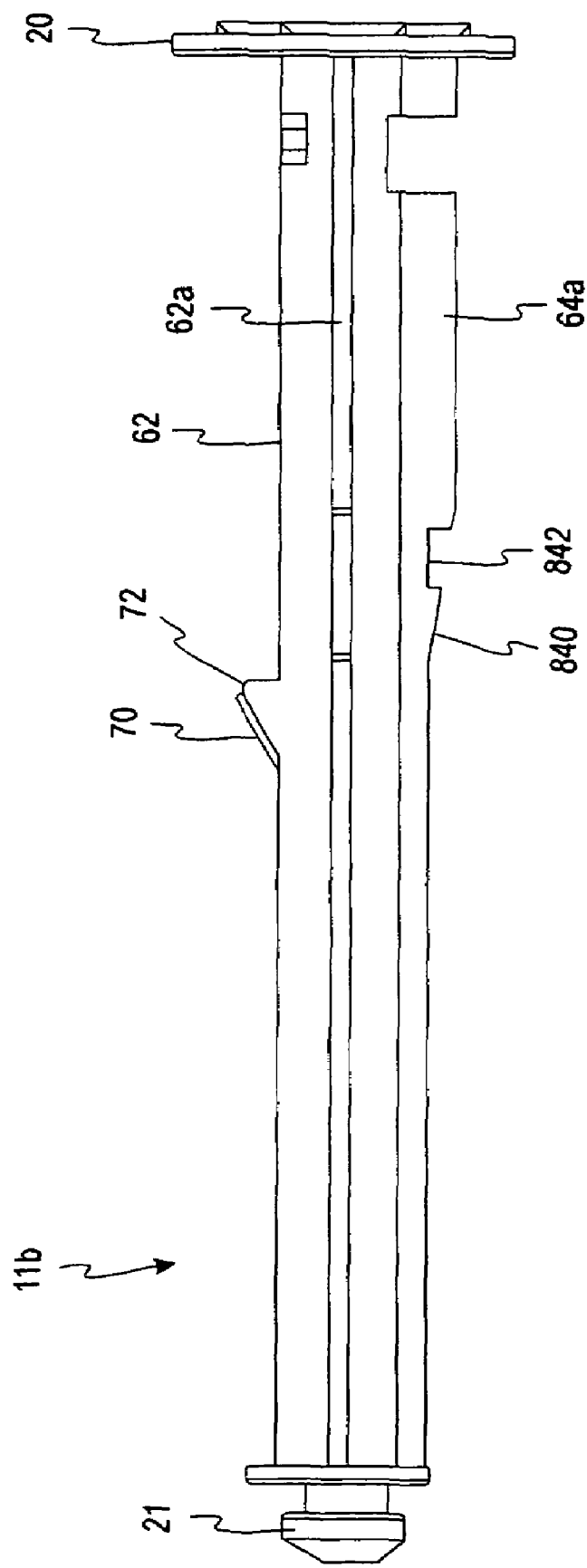
FIG. 72 shows another embodiment of a plunger.
Figure 74:
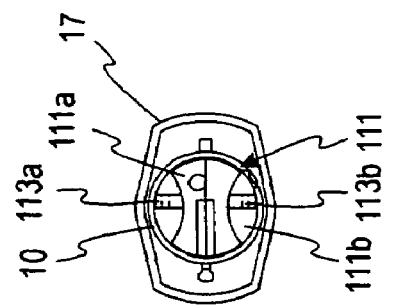
Figure 73:
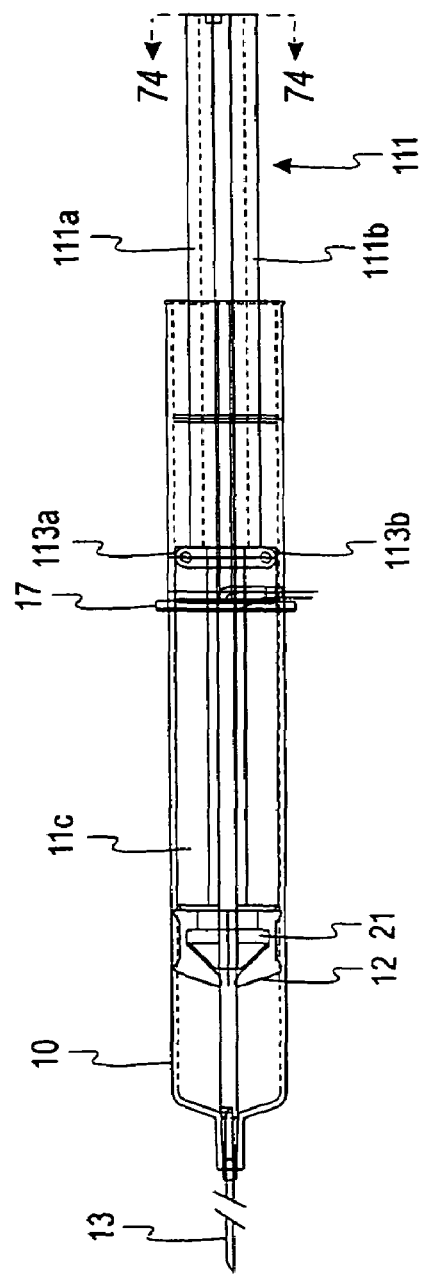
Figure 77:
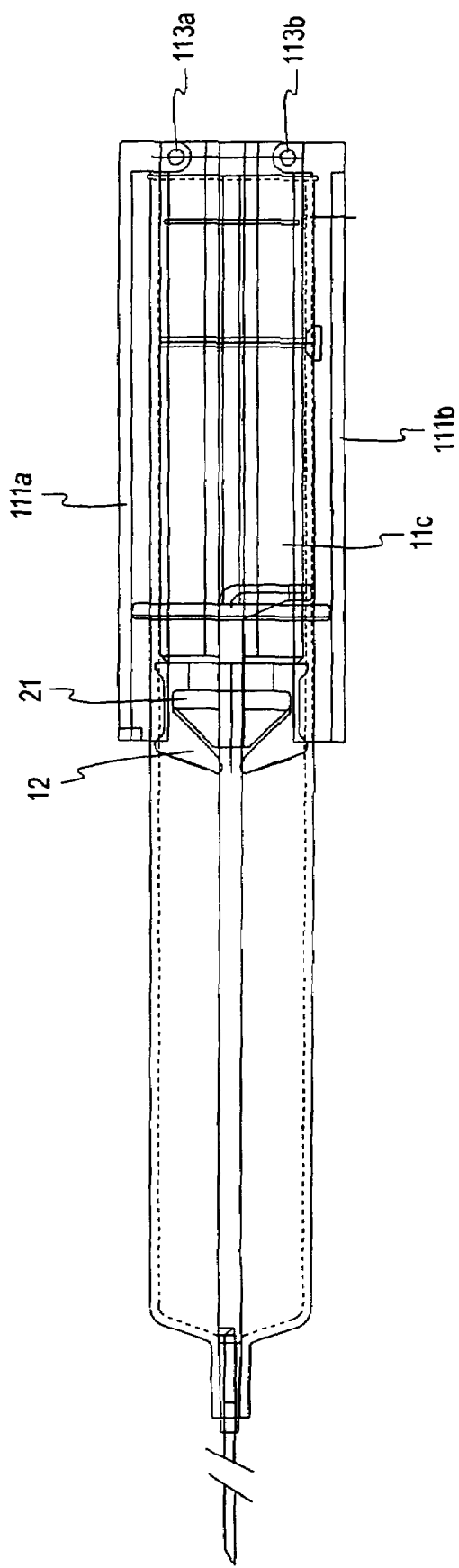

In the embodiment of FIGS. 65 and 66, a proximal flexible extension plate 902 similar to the plate 802 is provided and also is of a width to span and slidably engage the two walls or ribs 60, 62 which form the channel 33 in the plunger 11. In this regard, the plunger 11b of FIG. 72 is utilized in connection with this spring retainer. In the same fashion as the embodiment of FIG. 55, the spring retainer 2302a has at an end of the plate or projection 902 a pair of shaped recesses or grooves 908 which are of complementary shape for engaging the upper edge portions of the spring release projections 70 and 72 of the plunger 11b.

Finally, in order to releasably retain the needle holder, a through opening or window 905 is defined between flexible plate 902 and a support plate 903. The flexible plate 902 has an arch 902a and is rendered flexible by two slots s1 and s2. The slots separate the plate 902 and offer flexibility so that it can flex radially outwardly in response to a mechanical push of the projections 70 and 72 located on the plunger. With the deflexion of the arch 902a, the needle holder locked underneath is released. The support plate 903 is fixed to the spring retainer 2302a and extends proximally to form a concave margin to accommodate the needle holder which is locked under the plate 902.

Figure 69:
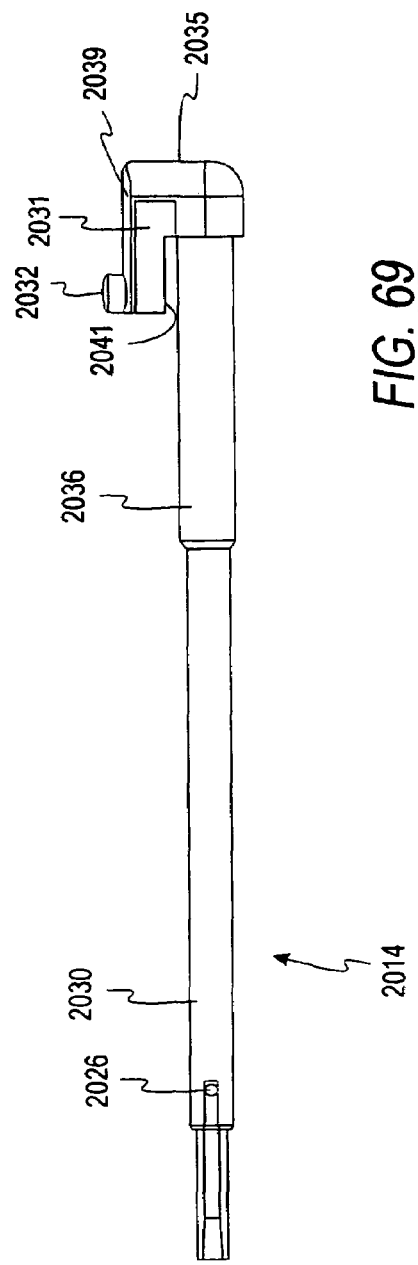
FIG. 69 is a side elevation of another embodiment of a needle holder used in connection with the spring retainer element of FIGS. 65-67.
Figure 70:
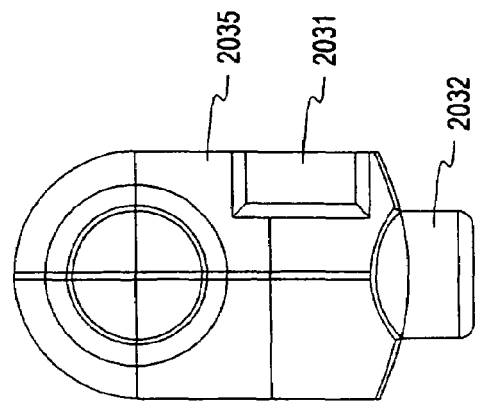
FIG. 70 is an enlarged top view of the needle holder of FIG. 68.

As best viewed in FIG. 71, the opening 905 releasably engages a radially projecting, relatively short arm 2032 of the needle holder 2014 shown in FIGS. 69 and 70. This needle holder is substantially similar in all other respects to the needle holders 14 and 1014, having a recess or slot 2041 formed by an elongate L-shaped extension 2039. This extension 2039 mounts the lateral arm 2032 at its distal end. The slot or opening 2041 receives and guides one end of the compression spring 300. The slot 2031 performs the same function as the slot 31 of the needle holder 11 described above, and the parts 2026, 2030, 2036 are also substantially the same as the parts 26, 30 and 36 of the needle holder described hereinabove. The top surface of the enlarged head 2035 of the needle holder 2014 does not require, and is therefore shown without, the flat surface portion 1017 of the embodiment of FIGS. 50, 60-62. It will be noted that the enlarged portion 29 of the barrel is aligned, upon assembly and during operation, with the lateral arm 32 of the needle holder, and with the plate 902 of the spring retainer to provide a relief space for the plate to flex back sufficiently to release the radially extending arm 2032 upon overadvancement of the plunger in the manner described hereinabove for release of the needle holder assembly. This results in retraction of the needle and locking of the parts in a retracted and nonreusable condition, including locking the plunger in an advanced position, as described above.

While particular embodiments and applications of the present invention have been illustrated and described, it is to be understood that the invention is not limited to the

What is claimed is:

1. A safety syringe assembly, comprising:
   an elongated, generally cylindrical barrel having a hollow interior forming a hollow nozzle located at a distal end of said barrel and opening into the interior of said barrel;
   a plunger slidably mounted in said barrel and having a longitudinal open channel;
   a needle;
   a needle holder mounting said needle at a distal end thereof and slidably mounted in said longitudinal open channel of said plunger for movement between an advanced position in which said needle on the distal end of said needle holder projects from a distal end of said nozzle, and a retracted position in which said needle is retracted within said barrel;
   a compression spring mounted inside of said barrel, and a spring retainer element located in and locked to said barrel and having a stabilizing surface extending along and about a portion of the internal wall of said barrel, and a spring support portion extending from said stabilizing surface interiorly of said barrel and supporting a distal end portion of said spring against expansion, said spring retainer also having a through opening for freely receiving said needle holder therethrough; said spring urging said needle holder toward its retracted position; and
   a latch having an engaged position in which said needle holder is latched relative to said barrel to hold said needle holder in its advanced position against the urging of said spring, and a disengaged position in which said needle holder is unlatched relative to said barrel to allow said spring to expand in a proximal direction to move said needle holder to its retracted position.

2. A retraction control unit for the safety syringe assembly of claim 1, wherein:
   said spring retainer element has a distal axial cantilever extension, inserted co-axially and locked within said barrel;
   said plunger has a compressibly engaged resilient cap, and one or more radial projections, is capable of reciprocal linear movements, and is inserted within said spring retainer clearing the cantilever;
   said needle holder is slidably mounted in said open channel of said plunger for movement between an advanced position in which a needle on the distal end of said needle holder projects from a distal end of said nozzle, and a retracted position in which said needle is retracted within said barrel;
   said spring retainer element forms a distal axial cantilever extension retaining a compression spring wrapped around said needle holder, such that said needle holder passes distally through an opening in the said axial extension; and
   a proximal surface of said spring retainer element has a stabilizer plate to support the needle holder and a deflectable anchoring plate that releasably holds the needle holder against an expansion force of the spring until it is radially deflected by the projections of said plunger, in response to a force that exceeds a fluid injection force.

3. The safety syringe assembly of claim 1 in which said barrel includes an expanded proximal segment, and said spring retainer element is located in and locked to said expanded proximal segment of said barrel.

4. A retraction control module for a retractable needle safety syringe having a barrel with a hollow interior, said module comprising:
   a hollow cylindrical tube with a distal axial extension forming a central cantilever with a central through opening, and a proximal eccentric anchoring plate forming an engagement geometry to engage and anchor a needle holder to the module, said hollow cylindrical tube being anchored to the proximal end of said barrel;
   said needle holder having an advanced position in which a needle on the distal end of said needle holder projects from a distal end of said syringe, and a retracted position in which said needle is retracted within said syringe;

a helical compressed spring encircling the needle holder and supported by said axial extension and the central cantilever with the needle holder and an attached needle passing through the central through opening of said cantilever, and within the tube; and a plunger compressibly engaged with a resilient cap passing through said cylindrical tube and having two parallel walls defining a central open channel that contact with the eccentric anchoring plate without deflecting said anchoring plate;

said plunger having a distally advanced position and ramps on said parallel walls which deflect the anchoring plate radially to disengage the needle holder and cause retraction of the needle when the plunger is advanced to said distally advanced position;

said needle holder being slidably mounted in said central open channel of said plunger;

said anchoring plate with extension arising from the opposite surface of the hollow cylinder from said distal axial extension and engaging with a proximal part of the needle holder preventing the expansion of said spring.

5. The retraction control module of claim 4 which, when engaged to a syringe barrel, converts a conventional syringe into a retractable needle safety syringe.

6. A retraction control module as set forth in claim 4, wherein retraction as a result of deflection and release of the needle holder from the anchoring plate by the plunger ramps is responsive to the advance of the plunger in the cylindrical tube to complete an injection.

7. A retractable needle safety syringe with said retraction control unit as set forth in claim 4, further comprising a closed needle protector, wherein a nozzle formed by said cylindrical tube has a male luer taper on its outer surface that mates with a female luer taper interior of said needle protector creating a taper lock to form an air and water tight seal between said nozzle and said needle protector, whereby air or fluids residing in the sealed cylindrical tube prevent advance of the plunger to the distal end of the cylindrical tube, avoiding retraction before the use of the syringe.

8. A retractable needle safety syringe comprising said retraction control module as set forth in claim 4 and an over-the-needle catheter located on and inserted synchronously with said needle into a vein, said catheter remaining in the vein while said needle is retracted.

9. The retraction control module as set forth in claim 4 wherein the plunger has linear axial mobility independent of movements of the spring and needle holder, and wherein, upon retraction of the needle, every component of the syringe is directly or indirectly locked with every other component of the syringe, such that the entire assembly is interlocked whereby the syringe is non-reusable.

10. The retraction control module as set forth in claim 4, wherein a proximal open end of said needle faces said distal end of said needle holder and communicates with said cylindrical tube by a side opening.

11. A retraction control unit for a retractable needle syringe comprising:

a spring retainer with a distal axial cantilever extension, inserted co-axially and locked within a barrel of a syringe;

a plunger with a compressibly engaged resilient cap, one or more radial projections and a central channel and capable of reciprocal linear movements, and engaged with said spring retainer clearing the cantilever;

a needle holder slidably mounted in said central open channel of said plunger for movement between an advanced position in which a needle on the distal end of said needle holder projects from a distal end of a nozzle, and a retracted position in which said needle is retracted within said barrel; and a seal between said needle holder and an inside surface of said nozzle to retain liquid within said barrel, the distal axial cantilever extension of the said spring retainer retaining a compression spring wrapped around said needle holder, such that said needle holder passes distally through an opening in the said axial extension, a proximal surface of said spring retainer having a deflectable anchoring plate that releasably holds the needle holder against an expansion force of the spring until it is radially deflected by the projections of said plunger, in response to a force that exceeds a fluid injection force, the deflection of said anchoring plate allowing said spring to retract said needle holder.

12. A retraction control unit for a retractable needle syringe as set forth in claim 11, wherein said plunger includes a detent on a plunger flange for engaging a latch, so as to interlock said syringe.

13. A retraction control unit for a retractable needle syringe as set forth in claim 11, further comprising a closed needle protector, wherein said nozzle of said barrel has a male luer taper on its outer surface that mates with a female luer taper interior of said needle protector creating a taper lock to form an air and water tight seal between said nozzle and said needle protector, whereby air or fluids residing in the sealed barrel prevent advance of the plunger to the distal end of the barrel, avoiding retraction before the use of the syringe.

14. A retraction control unit for a retractable needle syringe as set forth in claim 11, further comprising an over-the-needle catheter, said catheter being located on and inserted synchronously with said needle into a vein, said catheter remaining in the vein while said needle is retracted.

15. A retraction control unit for a retractable needle syringe as set forth in claim 11, wherein a proximal open end of said needle faces said distal end of said needle holder and communicates with said barrel by a side opening.

16. A retraction control unit for a retractable needle syringe as set forth in claim 11, wherein the retraction of said needle holder as a result of deflection of said anchoring plate is responsive to the advance of said plunger in said barrel to complete an injection.

17. A retraction control unit for a retractable needle syringe as set forth in claim 11, wherein said spring retainer is engaged to the barrel by one of a mechanical fit, a chemical bond and an ultrasonic bond.

18. A retraction control unit for a retractable needle safety syringe having a barrel with a hollow interior, said module comprising:

a needle holder having an advanced position in which a needle on the distal end of said needle holder projects from a distal end of said syringe, and a retracted position in which said needle is retracted within said syringe, a hollow spring retainer with a distal axial extension forming a central cantilever with a central through opening, and a proximal eccentric anchoring plate forming an engagement geometry to engage and anchor said needle holder to the control unit, said hollow spring retainer being anchored to the proximal end of said barrel;

a helical compressed spring within said spring retainer and encircling said needle holder and supported by said axial extension and said central cantilever, with said needle holder and an attached needle passing through said central through-opening of said cantilever;

a plunger compressibly engaged with a resilient cap having a through-opening communicating with said spring retainer and having two parallel walls defining a central open channel that contacts said eccentric anchoring plate without deflecting said anchoring plate said plunger having a distally advanced position and ramps on said parallel walls which deflect the anchoring plate radially to disengage the needle holder and cause retraction of the needle when the plunger is advanced to said distally advanced position; and a seal between said needle holder and an inside surface of said nozzle to retain liquid within said barrel, said needle holder being slidably mounted in said central open channel of said plunger, and said anchoring plate with extension arising from said opposite surface of said spring retainer from said distal axial extension and engaging a proximal part of said needle holder to prevent the expansion of said spring.

19. The retraction control unit of claim 18 wherein said spring retainer is engaged to said barrel by one of a mechanical fit, a chemical bond and an ultrasonic bond.

20. The retraction control unit of claim 18 wherein when said anchoring plate is engaged with said needle holder, said needle holder is urged distally through said seal for normal use, and when disengaged the expanded spring of the control unit urges the needle and the needle holder inside the barrel.

21. The retraction control unit of claim 18 wherein hydraulic forces in the syringe do not affect the retraction control unit because said unit is outside a fluid chamber defined in the syringe.

22. Retraction control unit as claimed in claim 18, wherein retraction as a result of deflection and release of the needle holder from the anchoring plate by the plunger ramps is responsive to the advance of the plunger in the barrel to complete an injection.

23. A retractable needle safety syringe with said retraction control unit as set forth in claim 18, further comprising a closed needle protector, wherein said nozzle of said barrel has a male luer taper on its outer surface that mates with a female luer taper interior of said needle protector creating a taper lock to form an air and water tight seal between said nozzle and said needle protector, whereby air or fluids residing in the sealed barrel prevent advance of the plunger to the distal end of the barrel, avoiding retraction before the use of the syringe.

24. A retractable needle safety syringe as set forth in claim 18 further comprising an over-the-needle catheter, said catheter being located on and inserted synchronously with said needle into a vein, said catheter remaining in the vein while said needle is retracted.

* * * * *